US008168860B2

(12) United States Patent
Rosichan et al.

(10) Patent No.: US 8,168,860 B2
(45) Date of Patent: May 1, 2012

(54) COMPOSITIONS AND METHODS FOR THE MODIFICATION OF PHYSIOLOGICAL RESPONSES IN PLANTS

(75) Inventors: Jeffrey L. Rosichan, Ambler, PA (US); Daniel R. Gallie, Riverside, CA (US)

(73) Assignee: Rohm and Haas Company, Philadelphia, PA (US)

( * ) Notice: Subject to any disclaimer, the term of this patent is extended or adjusted under 35 U.S.C. 154(b) by 524 days.

(21) Appl. No.: 12/209,501

(22) Filed: Sep. 12, 2008

(65) Prior Publication Data

US 2009/0077684 A1    Mar. 19, 2009

Related U.S. Application Data

(63) Continuation of application No. PCT/US2008/075708, filed on Sep. 9, 2008.

(60) Provisional application No. 60/973,057, filed on Sep. 17, 2007.

(51) Int. Cl.
*A01H 5/00* (2006.01)
*A01H 1/00* (2006.01)
*C12N 15/82* (2006.01)

(52) U.S. Cl. ......... 800/283; 800/278; 800/298; 435/468

(58) Field of Classification Search ........................ None
See application file for complete search history.

(56) References Cited

U.S. PATENT DOCUMENTS

| | | | |
|---|---|---|---|
| 5,354,844 A | 10/1994 | Beug et al. |
| 5,459,127 A | 10/1995 | Felgner et al. |
| 5,530,028 A | 6/1996 | Lidert et al. |
| 5,580,859 A | 12/1996 | Felgner et al. |
| 5,589,466 A | 12/1996 | Felgner et al. |
| 5,693,622 A | 12/1997 | Wolff et al. |
| 5,856,435 A | 1/1999 | Bazile et al. |
| 5,880,333 A | 3/1999 | Goff et al. |
| 6,107,286 A | 8/2000 | Byk et al. |
| 6,172,048 B1 | 1/2001 | Behr et al. |
| 6,200,956 B1 | 3/2001 | Scherman et al. |
| 6,245,531 B1 | 6/2001 | Hogness et al. |
| 6,258,603 B1 | 7/2001 | Carlson et al. |
| 6,265,173 B1 | 7/2001 | Evans et al. |
| 6,294,716 B1 | 9/2001 | Meyerowitz et al. |
| 6,333,318 B1 | 12/2001 | Evans et al. |
| 6,784,340 B1 | 8/2004 | Aoyama |
| 7,091,038 B2 | 8/2006 | Palli et al. |
| 2003/0154509 A1 | 8/2003 | Pascal |
| 2003/0188331 A1 | 10/2003 | Choo |
| 2004/0128719 A1 | 7/2004 | Klee et al. |
| 2005/0060772 A1 | 3/2005 | Ciardi et al. |
| 2005/0066389 A1 | 3/2005 | Gallie et al. |
| 2005/0228016 A1 | 10/2005 | Michelotti et al. |
| 2005/0266457 A1 | 12/2005 | Palli et al. |
| 2006/0200875 A1 | 9/2006 | Guo et al. |
| 2008/0235816 A1 | 9/2008 | Dhadialla |
| 2009/0077684 A1 | 3/2009 | Gallie |

FOREIGN PATENT DOCUMENTS

| | | |
|---|---|---|
| WO | WO 97/38117 | 10/1997 |
| WO | WO 03/088738 | 10/2003 |
| WO | WO 2010/101884 | 9/2010 |

OTHER PUBLICATIONS

Ayoma et al. The Plant Journal (1997) 11(3) 605-612.*
Christiane Kanz (Current Opinion in Biot (1996), 7:168-172.*
Zuo et al. The Plant Journal (2000) 24(2) 265-273.*
Antoniewski, "The ecdysone response enhancer of the Fbp1 gene of *Drosophila melanogaster* is a direct target for the EcR/USP nuclear receptor", Mol Cell Biol, 14(7):4465-4474 (Jul. 1994).
Baima, "The *arabidopsis* ATHB-8 HD-zip protein acts as a differentiation-promoting transcription factor of the vascular meristems", Plant Physiol, 126(2):643-655 (Jun. 2001).
Bezerra, "A corm-specific gene encodes tarin, a major globulin of taro (*Colocasia esculenta* L. Schott)", Plant Mol Biol, 28(1):137-144 (Apr. 1995).
Blume, "Expression of ACC oxidase promoter-GUS fusions in tomato and *Nicotiana plumbaginifolia* regulated by developmental and environmental stimuli", Plant J, 12(4):731-746 (Oct. 1997).
Brent, "A eukaryotic transcriptional activator bearing the DNA specificity of a prokaryotic repressor", Cell, 43(3, Part 2):729-736 (Dec. 1985). Busk, "Regulatory elements in vivo in the promoter of the abscisic acid responsive gene rab17 from maize", Plant J, 11(6):1285-1295 (Jun. 1997).
Casal, "Different phototransduction kinetics of phytochrome A and phytochrome B in *Arabidopsis thaliana*", Plant Physiol, 116(4):1533-1538 (Apr. 1998).
Chen, "Ethylene signal transduction", Annals of Botany, 95(6):901-915 (May 2005; Epub date Mar. 7, 2005).
Cherbas, "Identification of ecdysone response elements by analysis of the *Drosophila* Eip28/29 gene", Genes Dev, 5(1):120-131 (Jan. 1991).
Choi, "Tissue-specific and developmental regulation of a gene encoding a low molecular weight sulfur-rich protein in soybean seeds", Mol Genet, 246(2):266-268 (Jan. 20, 1995).
Ciardi, "Regulation of Ethylene-mediated Responses at the Level of the Receptor ", Annals Bot Co, 88:813-822 (2001).

(Continued)

*Primary Examiner* — Medina A Ibrahim
(74) *Attorney, Agent, or Firm* — Thomas D. Rogerson; Mary E. Bak

(57) ABSTRACT

A gene expression system for controllable expression of ethylene response in a plant cell includes an activation cassette comprising a DNA-binding domain that recognizes a response element; an ecdysone receptor ligand binding domain; and an activation domain; and a target cassette comprising an inducible promoter, which comprises, in operative association, the response element and a minimal promoter responsive to the activation domain. The inducible promoter controls the expression of a nucleic acid sequence that encodes a selected protein that modifies sensitivity to ethylene in the plant. Interaction among the components of the activation cassette and target cassette, when in a plant cell, in the presence of an inducing composition, modulates expression of the selected protein and selectively modulates ethylene sensitivity in the plant cell. This modulation in the expression of the protein is controlled by the timing, the concentration and the duration of the application of the inducing composition. Transgenic plant cells, tissues, organs and entire plants are provided, which in the presence of the inducing composition control ethylene sensitivity. Ethylene sensitivity and/or ethylene production in such transgenic plants and tissues may be controlled for purposes of manipulating ripening, flower senescence and other ethylene sensitive functions of the plant.

15 Claims, 3 Drawing Sheets

OTHER PUBLICATIONS

Czarny, "Genetic modulation of ethylene biosynthesis and signaling in plants", Biotechnol Adv, 24(4):410-419 (Jul.-Aug. 2006; Epub Mar. 9, 2006).

Dasgupta, "Cloning and sequencing of 5' flanking sequence from the gene encoding 2S storage protein, from two *Brassica* species", Gene, 133(2):301-302 (Nov. 15, 1993).

D'Avino, "The moulting hormone ecdysone is able to recognize target elements composed of direct repeats", Mol Cell Endocrinol, 113(1):1-9 (Aug. 30, 1995).

De Castro, "Spatial and temporal gene expression patterns occur during corm development", Plant Cell, 4(12):1549-1559 (Dec. 1992).

Di Laurenzio, "The SCARECROW gene regulates an asymmetric cell division that is essential for generating the radial organization of the *Arabidopsis* root", Cell, 86(3):423-433 (Aug. 9, 1996).

Elge, "An *Arabidopsis* inositol phospholipid kinase strongly expressed in procambial cells: synthesis of PtdIns(4,5)P2 and PtdIns(3,4,5)P3 in insect cells by 5-phosphorylation of precursors", Plant J, 26(6):561-571 (Jun. 2001).

Enjuto, "Expression of the *Arabidopsis* HMG2 gene, encoding 3-hydroxy-3-methylglutaryl coenzyme A reductase, is restricted to meristematic and floral tissues", Plant Cell, 7(5):517-527 (May 1995).

Felgner, "Cationic liposome-mediated transfection", Nature-, 337(6205):387-388 (Jan. 26, 1989).

Ficker, "A promoter directing high level expression in pistils of transgenic plants", Plant Mol Biol, 35(4):425-431 (Nov. 1997).

Fisher, "Rapid, efficient production of homozygous transgenic tobacco plants with *Agrobacterium tumefaciens*: A seed-to-seed protocol", Plant Mol Biol Reporter, 13(3):278-289 (1995).

Galweiler, "Regulation of polar auxin transport by AtPIN1 in *Arabidopsis* vascular tissue", Science, 282(5397):2226-2230 (Dec. 18, 1998).

Granger, "Isolation of an *Arabidopsis* homologue of the maize homeobox Knotted-1 gene", Plant Mol Biol, 31(2):373-378 (May 1996).

Guzman, "Exploiting the triple response of *Arabidopsis* to identify ethylene-related mutants", Plant Cell, 2(6):513-523 (Jun. 1990).

Hake, "Homeobox genes in the functioning of plant meristems", Philos Trans R Soc Lond B Biol Sci, 350(1331):45-51 (Oct. 30, 1995).

Hansen, "Wound-inducible and organ-specific expression of ORF13 from *Agrobacterium* rhizogenes 8196 T-DNA in transgenic tobacco plants", Mol Genet, 254(3):337-343 (Apr. 16, 1997).

Hormann, "Superimposition evaluation of ecdysteroid agonist chemotypes through multidimensional QSAR", J Comput Aided Mol Des, 17(2-4):135-53 (Feb.-Apr. 2003).

Igarashi, "Expression of the Zinnia TED3 promoter in developing tracheary elements of transgenic *Arabidopsis*", Plant Mol Biol, 36(6):917-927 (Apr. 1998).

Kerstetter, "Sequence analysis and expression patterns divide the maize knotted1-like homeobox genes into two classes", Plant Cell, 6(12):1877-1887 (Dec. 1994).

Kim, "Design of TATA box-binding protein/zinc finger fusions for targeted regulation of gene expression", Proc Natl Acad Sci, USA, 94(8):3616-3620 (Apr. 15, 1997).

Kim, "Nuclear protein factors binding to a class I patatin promoter region are tuber-specific and sucrose-inducible", Plant Mol Biol, 26(2):603-615 (Oct. 1994).

Koelle, "The *Drosophila* EcR gene encodes an ecdysone receptor, a new member of the steroid receptor superfamily", Cell, 67(1):59-77 (Oct. 4, 1991).

Kumar, "Highly flexible ligand binding pocket of ecdysone receptor: a single amino acid change leads to discrimination between two groups of nonsteroidal ecdysone agonists", J Biol Chem, 279(26):27211-27218 (Jun. 25, 2004; Epub Apr. 23, 2004).

Lee, "Genes encoding oleosins in maize kernel of inbreds Mo17 and B73", Plant Mol Biol, 26(6):1981-1987 (Dec. 1994).

Li, "A novel myb-related gene from *Arabidopsis thaliana*", FEBS Lett, 379(2):117-121 (Jan. 29, 1996).

Lincoln, "A knotted1-like homeobox gene in *Arabidopsis* is expressed in the vegetative meristem and dramatically alters leaf morphology when overexpressed in transgenic plants", Plant Cell, 6(12):1859-1876 (Dec. 1994).

Long, "A member of the KNOTTED class of homeodomain proteins encoded by the STM gene of *Arabidopsis*", Nature, 379(6560):66-69 (Jan. 4, 1996).

Martin, "Identification of mutants in metabolically regulated gene expression", Plant J, 11(1):53-62 (Jan. 1997).

Matsuoka, "The promoters of two carboxylases in a C4 plant (maize) direct cell-specific, light-regulated expression in a C3 plant (rice)", Plant J, 6(3):311-319 (Sep. 1994).

Meier, "The tomato RBCS3A promoter requires integration into the chromatin for correct organ-specific regulation", FEBS Lett, 415(1):91-95 (Sep. 22, 1997).

Padidam, "Chemically regulated gene expression in plants", Curr Opin Plant Biol, 6(2):169-77 (Apr. 2003).

Sadowski, "GAL4-VP16 is an unusually potent transcriptional activator", Nature, 335(6190):563-564 (Oct. 6, 1988).

Shiina, "Identification of promoter elements involved in the cytosolic Ca(2+)-mediated photoregulation of maize cab-m1 expression", Plant Physiol, 115(2):477-483 (Oct. 1997).

Tice, "Synthesis and SAR of α-acylaminoketone ligands for control of gene expression", Bioorg Med Chem Lett, 2003 13(3):475-478 (Feb. 10, 2003).

Tice, "Optimization of α-acylaminoketone ecdysone agonists for control of gene expression", Bioorg Med Chem Lett, 13(11):1883-1886 (Jun. 2, 2003).

Wang, "Ethylene Biosynthesis and Signaling Networks", Plant Cell, (American Society of Plant Biologists), S131-S151 (2002).

Wu, "Receptor-mediated gene delivery and expression in vivo", J Biol Chem, 263(29):14621-14624 (Oct. 15, 1988).

Wilson, "Hepatocyte-directed gene transfer in vivo leads to transient improvement of hypercholesterolemia in low density lipoprotein receptor-deficient rabbits", J Biol Chem, 267(2):963-967 (Jan. 15, 1992).

Yamamoto, "Characterization of cis-acting sequences regulating root-specific gene . expression in tobacco", Plant Cell, 3(4):371-382 (Apr. 1991).

Qiao et al, Interplay between ethylene, ETP1/ETP2 F-box proteins, and degradation of EIN2 triggers ethylene response in *Arabidopsis*. Genes & Development, 23(4):512-21 (Feb. 15, 2009).

Gallie, Regulated ethylene sensitivity through the inducible expression of the *Arabidopsis* etr1-1 mutant ethylene receptor in tomato, Plant Physiology, 152(4):1928-1934 (Feb. 24, 2010).

Martinez et al, Ecdysone agonist inducible transcription in transgenic tobacco plants, Plant Journal, 19(1):97-106 (Jul. 1, 1999).

Padidam et al, Chemical-inducible, ecdysone receptor-based gene expression system for plants, Transgenic Research, 12(1):101-109 (Jan. 1, 2003).

Ajay, Ethylene receptors and molecular mechanism of ethylene sensitivity in plants, Macromolecular: Rapid Communications, 89(8):1348-1361 (Oct. 25, 2005).

Guo and Ecker, The ethylene signaling pathway: new insights, Current Opinions in Plant Biology, 7:40-49 (Feb. 2004).

Klee, H., Control of ethylene-mediated processes in tomato at the level of receptors, Journal of Experimental Botany, 53(377):2057-63 (Oct. 2002).

International Search Report dated Nov. 24, 2008, issued in parent International Patent Application No. PCT/US08/75708.

International Search Report dated Apr. 23, 2010, issued in related International Patent Application No. PCT/US2010/25872.

Supplementary European Search Report dated Jun. 30, 2010, issued in corresponding EP Patent Application No. 08831345.7.

Communication from the EPO dated Jul. 27, 2010 issued in corresponding EP Patent Application No. 08831345.7.

International Preliminary Report/written Opinion dated Mar. 24, 2010 issued in related International Patent Application No. PCT/US2008/075708.

Applicants' Response dated May 20, 2011 to the Communication from the EPO dated Jul. 27, 2010 issued in corresponding EP Patent Application No. 08831345.7.

Communication from the EPO dated Nov. 29, 2011 issued in corresponding EP Patent Application No. 08831345.7.

Translation and summary of an Office Action dated Nov. 25, 2011 from the Korean Intellectual Property Office in Korean Patent Application No. 10-2010-7008017, with agent advice redacted.

An Examination Report, dated Dec. 13, 2010 from the New Zealand Intellectual Property Office (NZIPO) in corresponding New Zealand application No. 583992.

An Official Action from the Canadian Intellectual Property Office, dated Nov. 10, 2011, in corresponding Canadian application No. 2,698,460.

Translation of a Notice of a First Office Action for corresponding Chinese Application No. 200880107634, dated Jul. 14, 2011.

The translation of the Applicants' Response, dated Oct. 11, 2011, for corresponding Chinese Application No. 20088010763.

* cited by examiner

```
SEQUENCE LISTING

<160> NUMBER OF SEQ ID NOS: 16

<210> SEQ ID NO 1
<211> LENGTH: 5001
<212> TYPE: DNA
<213> ORGANISM: Artificial
<220> FEATURE:
<223> OTHER INFORMATION: p185 cassette

<400> SEQUENCE: 1
atagtttaaa ctgaaggcgg gaaacgacaa tctgatccaa gctcaagcta agcttgcatg      60
cctgcaggat atcgtggatc caagcttgcc acgtgccgcc acgtgccgcc acgtgccgcc     120
acgtgcctct agaggatcca tctccactga cgtaagggat gacgcacaat cccactatcc     180
ttcgcaagac ccttcctcta tataaggaag ttcatttcat ttggagagga cacgctggga     240
tccccaccat ggcccccccg accgatgtca gcctggggga cgaactccac ttagacggcg     300
aggacgtggc gatggcgcat gccgacgcgc tagacgattt cgatctggac atgttggggg     360
acggggattc cccaggtccg ggatttaccc cccacgactc cgcccctac ggcgctctgg      420 atatggccga cttcgagttt gagcagatgt ttaccgatgc ccttggaatt gacgagtacg     480
gtgggaagct tctaggtacc tccagaagaa tatcaggcgg ggaattcggc gggatgaagc     540
tactgtcttc tatcgaacaa gcatgcgata tttgccgact taaaaagctc aagtgctcca     600
aagaaaaacc gaagtgcgcc aagtgtctga agaacaactg ggagtgtcgc tactctccca     660
aaaccaaaag gtctccgctg actagggcac atctgacaga agtggaatca aggctagaaa     720
gactggaaca gctatttcta ctgatttttc ctcgagaaga ccttgacatg attttgaaaa     780
tggattcttt acaggatata aaagcattgt taacaggatt atttgtacaa gataatgtga     840
ataaagatgc cgtcacagat agattggctt cagtggagac tgatatgcct ctaacattga     900
gacagcatag aataagtgcg acatcatcat cggaagagag tagtaacaaa ggtcaaagac     960
agttgactgt atcgggaggc ggtgggatcc ggcctgagtg cgtagtaccc gagactcagt    1020
gcgccatgaa gcggaaagag aagaaagcac agaaggagaa ggacaaactg cctgtcagca    1080
cgacgacggt ggacgaccac atgccgccca ttatgcagtg tgaacctcca cctcctgaag    1140
cagcaaggat tcacgaagtg gtcccaaggt ttctctccga caagctgttg gtgacaaacc    1200
ggcagaaaaa catcccccag ttgacagcca accagcagtt ccttatcgcc aggctcatct    1260
ggtaccagga cgggtacgag cagccttctg atgaagattt gaagaggatt acgcagacgt    1320
ggcagcaagc ggacgatgaa aacgaagagt cggacactcc cttccgccag atcgtggaga    1380
tgactatcct cacggtccaa cttatcgtgg agttcgcgaa gggattgcca gggttcgcca    1440
agatctcgca gcctgatcaa attacgctgc ttaaggcttg ctcaagtgag gtaatgatgc    1500
tccgagtcgc gcgacgatac gatgcggcct ccgacagtgt tctgttcgcg aacaaccaag    1560
cgtacactcg cgacaactac cgcaaggctg gcatggccta cgtcatcgag gatctactgc    1620
acttctgccg gtgcatgtac tctatggcgt tggacaacat ccattacgcg ctgctcacgg    1680
```

-continued

```
ctgtcgtcat cttttctgac cggccagggt tggagcagcc gcaactggtg aagagatcc    1740 agcggtacta cctgaatacg ctccgcatct atatcctgaa ccagctgagc gggtcggcgc    1800
gttcgtccgt catatacggc aagatcctct caatcctctc tgagctacgc acgctcggca    1860
tgcaaaactc caacatgtgc atctccctca agctcaagaa cagaaagctg ccgcctttcc    1920
tcgaggagat ctgggatgtg gcggacatgt cgcacaccca accgccgcct atcctcgagt    1980
cccccacgaa tctctagccc ctgcgcgcac gcatcgccga tgccgcgtcc ggccgcgctg    2040
ctctgagaat cgatatcaa gcttctagac ccgggctgca gagatctacg cgttaagctt    2100
aattcccgat cgttcaaaca tttggcaata agtttcttta agattgaatc ctgttgccgg    2160
tcttgcgatg attatcatat aatttctgtt gaattacgtt aagcatgtaa taattaacat    2220
gtaatgcatg acgttattta tgagatgggt ttttatgatt agagtcccgc aattatacat    2280
ttaatacgcg atagaaaaca aaatatagcg cgcaaactag gataaattat cgcgcgcggt    2340
gtcatctatg ttactagatc ggggactagt aaggccggcc gcttggatcc gctcggagga    2400
cagtactccg ctcggaggac agtactccgc tcggaggaca gtactccgct cgaggacagt    2460
actccgctcg gaggacagta ctccgatccg tcagatctgc aagacccttc ctctatataa    2520
ggaagttcat tcatttggga gaggacacgc tgaaccatgg aagtctgcaa ttgtattgaa    2580
ccgcaatggc cagcggatga attgttaatg aaataccaat acatctccga tttcttcatt    2640
gcgattgcgt attttcgat tcctcttgag ttgatttact ttgtgaagaa atcagccgtg    2700
tttccgtata gatgggtact tgttcagttt ggtgctttta tcgttctta tggagcaact    2760 catcttatta acttatggac tttcactacg cattcgagaa ccgtggcgct tgtgatgact    2820
accgcgaagg tgttaaccgc tgttgtctcg tgtgctactg cgttgatgct tgttcatatt    2880
attcctgatc ttttgagtgt taagactcgg gagcttttct tgaaaaataa agctgctgag    2940
ctcgatagag aaatgggatt gattcgaact caggaagaaa ccggaaggca tgtgagaatg    3000
ttgactcatg agattagaag cactttagat agacatacta ttttaaagac tacacttgtt    3060
gagcttggta ggacattagc tttggaggag tgtgcattgt ggatgcctac tagaactggg    3120
ttagagctac agcttttctta tacacttcgt catcaacatc ccgtggagta tacggttcct    3180
attcaattac cggtgattaa ccaagtgttt ggtactagta gggctgtaaa aatatctcct    3240
aattctcctg tggctaggtt gagacctgtt tctgggaaat atatgctagg ggaggtggtc    3300
gctgtgaggg ttccgcttct ccacctttct aattttcaga ttaatgactg gcctgagctt    3360
tcaacaaaga gatatgcttt gatggttttg atgcttcctt cagatagtgc aaggcaatgg    3420
catgtccatg agttggaact cgttgaagtc gtcgctgatc aggtggctgt agctctctca    3480
catgctgcga tcctagaaga gtcgatgcga gctagggacc ttctcatgga gcagaatgtt    3540
gctcttgatc tagctagacg agaagcagaa acagcaatcc gtgcccgcaa tgatttccta    3600
gcggttatga accatgaaat gcgaacaccg atgcatgcga ttattgcact ctcttcctta    3660
ctccaagaaa cggaactaac ccctgaacaa agactgatgg tggaaacaat acttaaaagt    3720 agtaacctt tggcaacttt gatgaatgat gtcttagatc tttcaaggtt agaagatgga    3780
agtcttcaac ttgaacttgg gacattcaat cttcatacat tatttagaga ggtcctcaat    3840
ctgataaagc ctatagcggt tgttaagaaa ttacccatca cactaaatct tgcaccgat    3900 ttgccagaat tgttgttgg ggatgagaaa cggctaatgc agataatatt aaatatagtt    3960
ggtaatgctg tgaaattctc caaacaaggt agtatctccg taaccgctct tgtcaccaag    4020
tcagacacac gagctgctga ctttttttgtc gtgccaactg ggagtcattt ctacttgaga    4080
```

```
gtgaaggtaa aagactctgg agcaggaata atcctcaag acattccaaa gattttcact      4140
aaatttgctc aaacacaatc tttagcgacg agaagctcgg gtggtagtgg gcttggcctc      4200
gccatctcca agaggtttgt gaatctgatg gagggtaaca tttggattga gagcgatggt      4260
cttggaaaag gatgcacggc tatctttgat gttaaacttg ggatctcaga acgttcaaac      4320
gaatctaaac agtcgggcat accgaaagtt ccagccattc cccgacattc aaatttcact      4380
ggacttaagg ttcttgtcat ggatgagaac ggggtaagta aatggtgac gaagggactt      4440 cttgtacacc ttgggtgcga agtgaccacg gtgagttcaa acgaggagtg tctccgagtt      4500
gtgtcccatg agcacaaagt ggtcttcatg gacgtgtgca tgcccggggt cgaaaactac      4560
caaatcgctc tccgtattca cgagaaattc acaaaacaac gccaccaacg gccactactt      4620
gtggcactca gtggtaacac tgacaaatcc acaaaagaga aatgcatgag ctttggtctt      4680
gacggtgtgt tgctcaaacc cgtatcacta gacaacataa gagatgttct gtctgatctt      4740
ctcgagcccc gggtactgta cgagtaagcg gccgctaggg catgtctaga agtccgcaaa      4800
aatcaccagt ctctctctac aaatctatct ctctctattt ttctccagaa taatgtgtga      4860
gtagttccca gataagggaa ttagggttct tatagggttt cgctcatgtg ttgagcatat      4920
aagaacccct tagtatgtat ttgtatttgt aaaatacttc tatcaataaa atttctaatt      4980
cctaaaacca aaatccagtg a                                              5001

<210> SEQ ID NO 2
<211> LENGTH: 4995
<212> TYPE: DNA
<213> ORGANISM: Artificial
<220> FEATURE:
<223> OTHER INFORMATION: p187 cassette

<400> SEQUENCE: 2
atagtttaaa ctgaaggcgg gaaacgacaa tctgatccaa gctcaagcta agcttgcatg        60
cctgcaggat atcgtggatc caagcttgcc acgtgccgcc acgtgccgcc acgtgccgcc       120
acgtgcctct agaggatcca tctccactga cgtaagggat gacgcacaat cccactatcc       180
ttcgcaagac ccttcctcta tataaggaag ttcatttcat ttggagagga cacgctggga       240
tccccaccat ggatccgcca ccatgctagc ccaccatgaa gctactgtct tctatcgaac       300
aagcatgcga tatttgccga cttaaaaagc tcaagtgctc caagaaaaaa ccgaagtgcg       360
ccaagtgtct gaagaacaac tgggagtgtc gctactctcc caaaaccaaa aggtctccgc       420
tgactagggc acatctgaca gaagtggaat caaggctaga aagactggaa cagctatttc       480
tactgatttt tcctcgagaa gaccttgaca tgattttgaa aatggattct ttacaggata       540
taaaagcatt gttaacagga ttatttgtac aagataatgt gaataaagat gccgtcacag       600
atagattggc ttcagtggag actgatatgc ctctaacatt gagacagcat agaataagtg       660
cgacatcatc atcggaagag agtagtaaca aaggtcaaag acagttgact gtatccatgg       720 ccccccccgac cgatgtcagc ctggggggacg aactccactt agacggcgag acgtggcga       780 tggcgcatgc cgacgcgcta gacgatttcg atctggacat gttgggggac ggggattccc       840
caggtccggg attacccccc cacgactccg cccctacgg cgctctggat atggccgact       900
tcgagtttga gcagatgttt accgatgccc ttggaattga cgagtacggt gggaagcttc       960
taggtacctc tagaagaata tcgtggcctg agtgcgtagt acccgagact cagtgcgcca      1020
tgaagcggaa agagaagaaa gcacagaagg agaaggacaa actgcctgtc agcacgacga      1080
cggtggacga ccacatgccg cccattatgc agtgtgaacc tccacctcct gaagcagcaa      1140
```

```
ggattcacga agtggtccca aggtttctct ccgacaagct gttggagaca aaccggcaga    1200
aaaacatccc ccagttgaca gccaaccagc agttccttat cgccaggctc atctggtacc    1260
aggacgggta cgagcagcct tctgatgaag atttgaagag gattacgcag acgtggcagc    1320
aagcggacga tgaaaacgaa gagtcggaca ctcccttccg ccagatcgtg gagatgacta    1380
tcctcacggt ccaacttatc gtggagttcg cgaagggatt gccagggttc gccaagatct    1440
cgcagcctga tcaaattacg ctgcttaagg cttgctcaag tgaggtaatg atgctccgag    1500
tcgcgcgacg atacgatgcg gcctccgaca gtgttctgtt cgcgaacaac caagcgtaca    1560
ctcgcgacaa ctaccgcaag gctggcatgg cctacgtcat cgaggatcta ctgcacttct    1620
gccggtgcat gtactctatg gcgttggaca acatccatta cgcgctgctc acggctgtcg    1680
tcatcttttc tgaccggcca gggttggagc agccgcaact ggtggaagag atccagcggt    1740
actacctgaa tacgctccgc atctatatcc tgaaccagct gagcgggtcg gcgcgttcgt    1800
ccgtcatata cggcaagatc ctctcaatcc tctctgagct acgcacgctc ggcatgcaaa    1860
actccaacat gtgcatctcc ctcaagctca gaacagaaa gctgccgcct ttcctcgagg    1920
agatctggga tgtggcggac atgtcgcaca cccaaccgcc gcctatcctc gagtccccca    1980
cgaatctcta gccctgcgc gcacgcatcg ccgatgccgc gtccggccgc gctgctctga    2040
gaattcgata tcaagcttct agacccgggc tgcagagatc tacgcgttaa gcttaattcc    2100
cgatcgttca aacatttggc aataaagttt cttaagattg aatcctgttg ccggtcttgc    2160
gatgattatc atataatttc tgttgaatta cgttaagcat gtaataatta acatgtaatg    2220
catgacgtta tttatgagat gggttttat gattagagtc ccgcaattat acatttaata    2280
cgcgatagaa acaaaatat agcgcgcaaa ctaggataaa ttatcgcgcg cggtgtcatc    2340
tatgttacta gatcggggac tagtaaggcc ggccgcttgg atccgctcgg aggacagtac    2400
tccgctcgga ggacagtact ccgctcgag gacagtactc cgctcgagga cagtactccg    2460
ctcggaggac agtactccga tccgtcagat ctgcaagacc cttcctctat ataaggaagt    2520
tcatttcatt tggagaggac acgctgaacc atggaagtct gcaattgtat tgaaccgcaa    2580
tggccagcgg atgaattgtt aatgaaatac caatacatct ccgatttctt cattgcgatt    2640
gcgtattttt cgattcctct tgagttgatt tactttgtga agaaatcagc cgtgtttccg    2700
tatagatggg tacttgttca gtttggtgct tttatcgttc tttatggagc aactcatctt    2760
attaacttat ggactttcac tacgcattcg agaaccgtgg cgcttgtgat gactaccgcg    2820
aaggtgttaa ccgctgttgt ctcgtgtgct actgcgttga tgcttgttca tattattcct    2880
gatcttttga gtgttaagac tcgggagctt ttcttgaaaa ataaagctgc tgagctcgat    2940
agagaaatgg gattgattcg aactcaggaa gaaaccggaa ggcatgtgag aatgttgact    3000
catgagatta gaagcacttt agatagacat actattttaa agactacact tgttgagctt    3060
ggtaggacat tagctttgga ggagtgtgca ttgtggatgc ctactagaac tgggttagag    3120
ctacagcttt cttatacact tcgtcatcaa catcccgtgg agtatacggt tcctattcaa    3180
ttaccggtga ttaaccaagt gttggtact agtagggctg taaaaatatc tcctaattct    3240
cctgtggcta ggttgagacc tgtttctggg aaatatatgc taggggaggt ggtcgctgtg    3300
agggttccgc ttctccacct ttctaatttt cagattaatg actggcctga ctttcaaca    3360 aagagatatg ctttgatggt tttgatgctt ccttcagata gtgcaaggca atggcatgtc    3420
catgagttgg aactcgttga agtcgtcgct gatcaggtgg ctgtagctct ctcacatgct    3480
gcgatcctag aagagtcgat gcgagctagg gaccttctca tggagcagaa tgttgctctt    3540
```

```
gatctagcta gacgagaagc agaaacagca atccgtgccc gcaatgattt cctagcggtt    3600
atgaaccatg aaatgcgaac accgatgcat gcgattattg cactctcttc cttactccaa    3660
gaaacggaac taacccctga acaaagactg atggtggaaa caatacttaa aagtagtaac    3720
cttttggcaa ctttgatgaa tgatgtctta gatctttcaa ggttagaaga tggaagtctt    3780
caacttgaac ttgggacatt caatcttcat acattattta gagaggtcct caatctgata    3840
aagcctatag cggttgttaa gaaattaccc atcacactaa atcttgcacc agatttgcca    3900
gaatttgttg ttggggatga gaaacggcta atgcagataa tattaaatat agttggtaat    3960
gctgtgaaat tctccaaaca aggtagtatc tccgtaaccg ctcttgtcac caagtcagac    4020
acacgagctg ctgactttt tgtcgtgcca actgggagtc atttctactt gagagtgaag    4080
gtaaaagact ctggagcagg aataaatcct caagacattc caagatttt cactaaattt    4140 gctcaaacac aatctttagc gacgagaagc tcggtggta gtgggcttgg cctcgccatc    4200
tccaagaggt ttgtgaatct gatggagggt aacatttgga ttgagagcga tggtcttgga    4260
aaaggatgca cggctatctt tgatgttaaa cttgggatct cagaacgttc aaacgaatct    4320
aaacagtcgg gcataccgaa agttccagcc attccccgac attcaaattt cactggactt    4380
aaggttcttg tcatggatga gaacggggta agtagaatgg tgacgaaggg acttcttgta    4440
caccttgggt gcgaagtgac cacggtgagt tcaaacgagg agtgtctccg agttgtgtcc    4500
catgagcaca aagtggtctt catggacgtg tgcatgcccg gggtcgaaaa ctaccaaatc    4560
gctctccgta ttcacgagaa attcacaaaa caacgccacc aacggccact acttgtggca    4620
ctcagtggta acactgacaa atccacaaaa gagaaatgca tgagctttgg tcttgacggt    4680
gtgttgctca aacccgtatc actagacaac ataagagatg ttctgtctga tcttctcgag    4740
ccccgggtac tgtacgagta agcggccgct agggcatgtc tagaagtccg caaaaatcac    4800
cagtctctct ctacaaatct atctctctct attttctcc agaataatgt gtgagtagtt    4860
cccagataag ggaattaggg ttcttatagg gtttcgctca tgtgttgagc atataagaaa    4920
cccttagtat gtatttgtat ttgtaaaata cttctatcaa taaatttct aattcctaaa    4980 accaaaatcc agtga                                                    4995

<210> SEQ ID NO 3
<211> LENGTH: 4427
<212> TYPE: DNA
<213> ORGANISM: Artificial
<220> FEATURE:
<223> OTHER INFORMATION: p184 cassette

<400> SEQUENCE: 3
atagtttaaa ctgaaggcgg gaaacgacaa tctgatccaa gctcaagcta agcttgcatg      60
cctgcaggat atcgtggatc caagcttgcc acgtgccgcc acgtgccgcc acgtgccgcc     120
acgtgcctct agaggatcca tctccactga cgtaagggat gacgcacaat cccactatcc     180
ttcgcaagac ccttcctcta tataaggaag ttcatttcat ttggagagga cacgctggga     240
tccccaccat ggccccccg accgatgtca gcctggggga cgaactccac ttagacggcg     300
aggacgtggc gatggcgcat gccgacgcgc tagacgattt cgatctggac atgttggggg     360
acggggattc cccaggtccg ggatttaccc ccacgactc gcccctac ggcgctctgg     420 atatggccga cttcgagttt gagcagatgt ttaccgatgc ccttggaatt gacgagtacg     480
gtgggaagct tctaggtacc tccagaagaa tatcaggcgg ggaattcggc gggatgaagc     540
tactgtcttc tatcgaacaa gcatgcgata tttgccgact taaaaagctc aagtgctcca     600
```

```
aagaaaaacc gaagtgcgcc aagtgtctga agaacaactg ggagtgtcgc tactctccca       660
aaaccaaaag gtctccgctg actagggcac atctgacaga agtggaatca aggctagaaa       720
gactggaaca gctatttcta ctgattttc ctcgagaaga ccttgacatg attttgaaaa       780
tggattcttt acaggatata aaagcattgt taacaggatt atttgtacaa gataatgtga       840
ataaagatgc cgtcacagat agattggctt cagtggagac tgatatgcct ctaacattga       900
gacagcatag aataagtgcg acatcatcat cggaagagag tagtaacaaa ggtcaaagac       960
agttgactgt atcgggaggc ggtgggatcc ggcctgagtg cgtagtaccc gagactcagt      1020
gcgccatgaa gcggaaagag aagaaagcac agaaggagaa ggacaaactg cctgtcagca      1080
cgacgacggt ggacgaccac atgccgccca ttatgcagtg tgaacctcca cctcctgaag      1140
cagcaaggat tcacgaagtg gtcccaaggt ttctctccga caagctgttg gtgacaaacc      1200
ggcagaaaaa catcccccag ttgacagcca accagcagtt ccttatcgcc aggctcatct      1260
ggtaccagga cgggtacgag cagccttctg atgaagattt gaagaggatt acgcagacgt      1320
ggcagcaagc ggacgatgaa aacgaagagt cggacactcc cttccgccag atcgtggaga      1380
tgactatcct cacggtccaa cttatcgtgg agttcgcgaa gggattgcca gggttcgcca      1440
agatctcgca gcctgatcaa attacgctgc ttaaggcttg ctcaagtgag gtaatgatgc      1500
tccgagtcgc gcgacgatac gatgcggcct ccgacagtgt tctgttcgcg aacaaccaag      1560
cgtacactcg cgacaactac cgcaaggctg gcatggccta cgtcatcgag gatctactgc      1620
acttctgccg gtgcatgtac tctatggcgt tggacaacat ccattacgcg ctgctcacgg      1680
ctgtcgtcat cttttctgac cggccagggt tggagcagcc gcaactggtg gaagagatcc      1740
agcggtacta cctgaatacg ctccgcatct atatcctgaa ccagctgagc gggtcggcgc      1800
gttcgtccgt catatacggc aagatcctct caatcctctc tgagctacgc acgctcggca      1860
tgcaaaactc caacatgtgc atctccctca agctcaagaa cagaaagctg ccgccttttcc      1920 tcgaggagat ctgggatgtg gcggacatgt cgcacaccca accgccgcct atcctcgagt      1980
cccccacgaa tctctagccc ctgcgcgcac gcatcgccga tgccgcgtcc ggccgcgctg      2040
ctctgagaat tcgatatcaa gcttctagac ccgggctgca gagatctacg cgttaagctt      2100
aattcccgat cgttcaaaca tttggcaata aagtttctta agattgaatc ctgttgccgg      2160
tcttgcgatg attatcatat aatttctgtt gaattacgtt aagcatgtaa taattaacat      2220
gtaatgcatg acgttattta tgagatgggt ttttatgatt agagtcccgc aattatacat      2280
ttaatacgcg atagaaaaca aaatatagcg cgcaaactag gataaattat cgcgcgcggt      2340
gtcatctatg ttactagatc ggggactagt aaggccggcc gcttggatcc gctcggagga      2400
cagtactccg ctcggaggac agtactccgc tcggaggaca gtactccgct cgaggacagt      2460
actccgctcg gaggacagta ctccgatccg tcagatctgc aagacccttc ctctatataa      2520
ggaagttcat ttcatttgga gaggacacgc tgaaccatgg aagacgccaa aacataaag      2580 aaaggcccgg cgccattcta tccgctggaa gatggaaccg ctggagagca actgcataag      2640
gctatgaaga gatacgccct ggttcctgga acaattgctt ttacagatgc acatatcgag      2700
gtggacatca cttacgctga gtacttcgaa atgtccgttc ggttggcaga agctatgaaa      2760
cgatatgggc tgaatacaaa tcacagaatc gtcgtatgca gtgaaaactc tcttcaattc      2820
tttatgccgg tgttgggcgc gttatttatc ggagttgcag ttgcgcccgc gaacgacatt      2880
tataatgaac gtgaattgct caacagtatg ggcatttcgc agcctaccgt ggtgttcgtt      2940
tccaaaaagg ggttgcaaaa aatttttgaac gtgcaaaaaa agctcccaat catccaaaaa      3000
```

| | | | |
|---|---|---|---|
| attattatca | tggattctaa | aacggattac | agggatttc agtcgatgta cacgttcgtc | 3060 |
| acatctcatc | tacctcccgg | ttttaatgaa | tacgattttg tgccagagtc cttcgatagg | 3120 |
| gacaagacaa | ttgcactgat | catgaactcc | tctggatcta ctggtctgcc taaaggtgtc | 3180 |
| gctctgcctc | atagaactgc | ctgcgtgaga | ttctcgcatg ccagagatcc tattttggc | 3240 |
| aatcaaatca | ttccggatac | tgcgatttta | agtgttgttc cattccatca cggttttgga | 3300 |
| atgtttacta | cactcggata | tttgatatgt | ggatttcgag tcgtcttaat gtatagattt | 3360 |
| gaagaagagc | tgtttctgag | gagccttcag | gattacaaga ttcaaagtgc gctgctggtg | 3420 |
| ccaaccctat | tctccttctt | cgccaaaagc | actctgattg acaaatacga tttatctaat | 3480 |
| ttacacgaaa | ttgcttctgg | tggcgctccc | ctctctaagg aagtcgggga agcggttgcc | 3540 |
| aagaggttcc | atctgccagg | tatcaggcaa | ggatatgggc tcactgagac tacatcagct | 3600 |
| attctgatta | cacccgaggg | ggatgataaa | ccgggcgcgg tcgtaaagt tgttccattt | 3660 |
| tttgaagcga | aggttgtgga | tctggatacc | gggaaaacgc tgggcgttaa tcaaagaggc | 3720 |
| gaactgtgtg | tgagaggtcc | tatgattatg | tccggttatg taaacaatcc ggaagcgacc | 3780 |
| aacgccttga | ttgacaagga | tggatggcta | cattctggag acatagctta ctgggacgaa | 3840 |
| gacgaacact | tcttcatcgt | tgaccgcctg | aagtctctga ttaagtacaa aggctatcag | 3900 |
| gtggctcccg | ctgaattgga | atccatcttg | ctccaacacc ccaacatctt cgacgcaggt | 3960 |
| gtcgcaggtc | ttcccgacga | tgacgccggt | gaacttcccg ccgccgttgt tgttttggag | 4020 |
| cacggaaaga | cgatgacgga | aaaagagatc | gtggattacg tcgccagtca agtaacaacc | 4080 |
| gcgaaaaagt | tgcgcggagg | agttgtgttt | gtggacgaag taccgaaagg tcttaccgga | 4140 |
| aaactcgacg | caagaaaaat | cagagagatc | ctcataaagg ccaagaaggg cggaaagatc | 4200 |
| gccgtgtaat | tctagaagtc | cgcaaaaatc | accagtctct ctctacaaat ctatctctct | 4260 |
| ctatttttct | ccagaataat | gtgtgagtag | ttcccagata agggaattag ggttcttata | 4320 |
| gggtttcgct | catgtgttga | gcatataaga | aacccttagt atgtatttgt atttgtaaaa | 4380 |
| tacttctatc | aataaaattt | ctaattccta | aaaccaaaat ccagtga | 4427 |

<210> SEQ ID NO 4
<211> LENGTH: 4421
<212> TYPE: DNA
<213> ORGANISM: Artificial
<220> FEATURE:
<223> OTHER INFORMATION: p186 cassette

<400> SEQUENCE: 4

| | | | |
|---|---|---|---|
| atagtttaaa | ctgaaggcgg | gaaacgacaa | tctgatccaa gctcaagcta agcttgcatg | 60 |
| cctgcaggat | atcgtggatc | caagcttgcc | acgtgccgcc acgtgccgcc acgtgccgcc | 120 |
| acgtgcctct | agaggatcca | tctccactga | cgtaagggat gacgcacaat cccactatcc | 180 |
| ttcgcaagac | ccttcctcta | tataaggaag | ttcatttcat ttggagagga cacgctggga | 240 |
| tccccaccat | ggatccgcca | ccatgctagc | ccaccatgaa gctactgtct tctatcgaac | 300 |
| aagcatcga | tatttgccga | cttaaaaagc | tcaagtgctc caagaaaaa ccgaagtgcg | 360 |
| ccaagtgtct | gaagaacaac | tgggagtgtc | gctactctcc caaaaccaaa aggtctccgc | 420 |
| tgactagggc | acatctgaca | gaagtggaat | caaggctaga aagactggaa cagctatttc | 480 |
| tactgatttt | tcctcgagaa | gaccttgaca | tgattttgaa aatggattct ttacaggata | 540 |
| taaaagcatt | gttaacagga | ttatttgtac | aagataatgt gaataaagat gccgtcacag | 600 |
| atagattggc | ttcagtggag | actgatatgc | ctctaacatt gagacagcat agaataagtg | 660 |

```
cgacatcatc atcggaagag agtagtaaca aaggtcaaag acagttgact gtatccatgg    720
cccccccgac cgatgtcagc ctgggggacg aactccactt agacggcgag gacgtggcga    780
tggcgcatgc cgacgcgcta gacgatttcg atctggacat gttgggggac ggggattccc    840
caggtccggg atttaccccc cacgactccg ccccctacgg cgctctggat atggccgact    900
tcgagtttga gcagatgttt accgatgccc ttggaattga cgagtacggt gggaagcttc    960
taggtacctc tagaagaata tcgtggcctg agtgcgtagt acccgagact cagtgcgcca   1020
tgaagcggaa agagaagaaa gcacagaagg agaaggacaa actgcctgtc agcacgacga   1080
cggtggacga ccacatgccg cccattatgc agtgtgaacc tccacctcct gaagcagcaa   1140
ggattcacga agtggtccca aggtttctct ccgacaagct gttggagaca accggcaga    1200
aaaacatccc ccagttgaca gccaaccagc agttccttat cgccaggctc atctggtacc   1260
aggacgggta cgagcagcct tctgatgaag atttgaagag gattacgcag acgtggcagc   1320
aagcggacga tgaaaacgaa gagtcggaca ctcccttccg ccagatcgtg gagatgacta   1380
tcctcacggt ccaacttatc gtggagttcg cgaagggatt gccagggttc gccaagatct   1440
cgcagcctga tcaaattacg ctgcttaagg cttgctcaag tgaggtaatg atgctccgag   1500
tcgcgcgacg atacgatgcg gcctccgaca gtgttctgtt cgcgaacaac caagcgtaca   1560
ctcgcgacaa ctaccgcaag gctggcatgg cctacgtcat cgaggatcta ctgcacttct   1620
gccggtgcat gtactctatg gcgttggaca acatccatta cgcgctgctc acggctgtcg   1680
tcatcttttc tgaccggcca gggttggagc agccgcaact ggtggaagag atccagcggt   1740
actacctgaa tacgctccgc atctatatcc tgaaccagct gagcgggtcg gcgcgttcgt   1800
ccgtcatata cggcaagatc ctctcaatcc tctctgagct acgcacgctc ggcatgcaaa   1860
actccaacat gtgcatctcc ctcaagctca agaacagaaa gctgccgcct ttcctcgagg   1920
agatctggga tgtggcggac atgtcgcaca cccaaccgcc gcctatcctc gagtccccca   1980
cgaatctcta gcccctgcgc gcacgcatcg ccgatgccgc gtccggccgc gctgctctga   2040
gaattcgata tcaagcttct agacccgggc tgcagagatc tacgcgttaa gcttaattcc   2100
cgatcgttca acatttggc aataaagttt cttaagattg aatcctgttg ccggtcttgc    2160
gatgattatc atataatttc tgttgaatta cgttaagcat gtaataatta acatgtaatg   2220
catgacgtta tttatgagat gggttttat gattagagtc ccgcaattat acatttaata    2280
cgcgatagaa aacaaaatat agcgcgcaaa ctaggataaa ttatcgcgcg cggtgtcatc   2340
tatgttacta gatcggggac tagtaaggcc ggccgcttgg atccgctcgg aggacagtac   2400
tccgctcgga ggacagtact ccgctcgag gacagtactc cgctcgagga cagtactccg    2460
ctcggaggac agtactccga tccgtcagat ctgcaagacc cttcctctat ataaggaagt   2520
tcatttcatt tggagaggac acgctgaacc atggaagacg ccaaaaacat aaagaaaggc   2580
ccggcgccat tctatccgct ggaagatgga accgctggag agcaactgca taaggctatg   2640
aagagatacg ccctggttcc tggaacaatt gcttttacag atgcacatat cgaggtggac   2700
atcacttacg ctgagtactt cgaaatgtcc gttcggttgg cagaagctat gaaacgatat   2760
gggctgaata caaatcacag aatcgtcgta tgcagtgaaa actctcttca attctttatg   2820
ccggtgttgg gcgcgttatt tatcggagtt gcagttgcgc ccgcgaacga catttataat   2880
gaacgtgaat tgctcaacag tatgggcatt tcgcagccta ccgtggtgtt cgtttccaaa   2940
aagggggttgc aaaaaatttt gaacgtgcaa aaaaagctcc caatcatcca aaaaattatt   3000
atcatggatt ctaaaacgga ttaccaggga tttcagtcga tgtacacgtt cgtcacatct   3060
```

```
catctacctc ccggttttaa tgaatacgat tttgtgccag agtccttcga tagggacaag    3120
acaattgcac tgatcatgaa ctcctctgga tctactggtc tgcctaaagg tgtcgctctg    3180
cctcatagaa ctgcctgcgt gagattctcg catgccagag atcctatttt tggcaatcaa    3240
atcattccgg atactgcgat tttaagtgtt gttccattcc atcacggttt tggaatgttt    3300
actacactcg atatttgat atgtggattt cgagtcgtct taatgtatag atttgaagaa    3360
gagctgtttc tgaggagcct tcaggattac aagattcaaa gtgcgctgct ggtgccaacc    3420
ctattctcct tcttcgccaa aagcactctg attgacaaat acgatttatc taatttacac    3480
gaaattgctt ctggtggcgc tcccctctct aaggaagtcg gggaagcggt tgccaagagg    3540
ttccatctgc caggtatcag gcaaggatat gggctcactg agactacatc agctattctg    3600
attacacccg aggggatga taaaccgggc gcggtcggta agttgttcc attttttgaa    3660 gcgaaggttg tggatctgga taccgggaaa acgctgggcg ttaatcaaag aggcgaactg    3720
tgtgtgagag gtcctatgat tatgtccggt tatgtaaaca atccggaagc gaccaacgcc    3780
ttgattgaca aggatggatg gctacattct ggagacatag cttactggga cgaagacgaa    3840
cacttcttca tcgttgaccg cctgaagtct ctgattaagt acaaaggcta tcaggtggct    3900
cccgctgaat tggaatccat cttgctccaa caccccaaca tcttcgacgc aggtgtcgca    3960
ggtcttcccg acgatgacgc cggtgaactt cccgccgccg ttgttgtttt ggagcacgga    4020
aagacgatga cggaaaaaga gatcgtggat tacgtcgcca gtcaagtaac aaccgcgaaa    4080
aagttgcgcg gaggagttgt gtttgtggac gaagtaccga aagtcttac cggaaaactc    4140 gacgcaagaa aaatcagaga gatcctcata aaggccaaga agggcggaaa gatcgccgtg    4200
taattctaga agtccgcaaa aatcaccagt ctctctctac aaatctatct ctctctattt    4260
ttctccagaa taatgtgtga gtagttccca gataagggaa ttagggttct tatagggttt    4320
cgctcatgtg ttgagcatat aagaaaccct tagtatgtat ttgtatttgt aaaatacttc    4380
tatcaataaa atttctaatt cctaaaacca aaatccagtg a                        4421
```

<210> SEQ ID NO 5
<211> LENGTH: 7228
<212> TYPE: DNA
<213> ORGANISM: Artificial
<220> FEATURE:
<223> OTHER INFORMATION: p1002 cassette

<400> SEQUENCE: 5

```
atagtttaaa ctgaaggcgg gaaacgacaa tctgatccaa gctcaagcta agcttgcatg      60
cctgcaggat atcgtggatc caagcttgcc acgtgccgcc acgtgccgcc acgtgccgcc     120
acgtgcctct agaggatcca tctccactga cgtaagggat gacgcacaat cccactatcc     180
ttcgcaagac ccttcctcta tataaggaag ttcatttcat ttggagagga cacgctggga     240
tccccaccat ggcccccccg accgatgtca gcctggggga cgaactccac ttagacggcg     300
aggacgtggc gatggcgcat gccgacgcgc tagacgattt cgatctggac atgtgggggg     360
acggggattc cccaggtccg ggatttaccc cccacgactc cgcccctac ggcgctctgg     420 atatggccga cttcgagttt gagcagatgt ttaccgatgc ccttggaatt gacgagtacg     480
gtgggaagct tctaggtacc tccagaagaa tatcaggcgg ggaattcggc gggatgaagc     540
tactgtcttc tatcgaacaa gcatgcgata tttgccgact taaaaagctc aagtgctcca     600
aagaaaaacc gaagtgcgcc aagtgtctga agaacaactg ggagtgtcgc tactctccca     660
aaaccaaaag gtctccgctg actagggcac atctgacaga agtggaatca aggctagaaa     720
```

```
gactggaaca gctatttcta ctgattttc ctcgagaaga ccttgacatg attttgaaaa    780
tggattcttt acaggatata aaagcattgt taacaggatt atttgtacaa gataatgtga    840
ataaagatgc cgtcacagat agattggctt cagtggagac tgatatgcct ctaacattga    900
gacagcatag aataagtgcg acatcatcat cggaagagag tagtaacaaa ggtcaaagac    960
agttgactgt atcgggaggc ggtgggatcc ggcctgagtg cgtagtaccc gagactcagt   1020
gcgccatgaa gcggaaagag aagaaagcac agaaggagaa ggacaaactg cctgtcagca   1080
cgacgacggt ggacgaccac atgccgccca ttatgcagtg tgaacctcca cctcctgaag   1140
cagcaaggat tcacgaagtg gtcccaaggt ttctctccga caagctgttg gtgacaaacc   1200
ggcagaaaaa catcccccag ttgacagcca accagcagtt ccttatcgcc aggctcatct   1260
ggtaccagga cgggtacgag cagccttctg atgaagattt gaagaggatt acgcagacgt   1320
ggcagcaagc ggacgatgaa aacgaagagt cggacactcc cttccgccag atcgtggaga   1380
tgactatcct cacggtccaa cttatcgtgg agttcgcgaa gggattgcca gggttcgcca   1440
agatctcgca gcctgatcaa attacgctgc ttaaggcttg ctcaagtgag gtaatgatgc   1500
tccgagtcgc gcgacgatac gatgcggcct ccgacagtgt tctgttcgcg aacaaccaag   1560
cgtacactcg cgacaactac cgcaaggctg gcatggccta cgtcatcgag gatctactgc   1620
acttctgccg gtgcatgtac tctatggcgt tggacaacat ccattacgcg ctgctcacgg   1680
ctgtcgtcat ctttctgac cggccagggt tggagcagcc gcaactggtg aagagatcc   1740
agcggtacta cctgaatacg ctccgcatct atatcctgaa ccagctgagc gggtcggcgc   1800
gttcgtccgt catatacggc aagatcctct caatcctctc tgagctacgc acgctcggca   1860
tgcaaaactc caacatgtgc atctccctca agctcaagaa cagaaagctg ccgccttttcc   1920
tcgaggagat ctgggatgtg cggacatgt cgcacaccca accgccgcct atcctcgagt   1980
cccccacgaa tctctagccc ctgcgcgcac gcatcgccga tgccgcgtcc ggccgcgctg   2040
ctctgagaat tcgatatcaa gcttctagac ccgggctgca gagatctacg cgttaagctt   2100
aattcccgat cgttcaaaca tttggcaata aagtttctta agattgaatc ctgttgccgg   2160
tcttgcgatg attatcatat aatttctgtt gaattacgtt aagcatgtaa taattaacat   2220
gtaatgcatg acgttattta tgagatgggt ttttatgatt agagtcccgc aattatacat   2280
ttaatacgcg atagaaaaca aaatatagcg cgcaaactag gataaattat cgcgcgcggt   2340
gtcatctatg ttactagatc ggggactagt aaggccggcc gcttggatcc gctcggagga   2400
cagtactccg ctcggaggac agtactccgc tcggaggaca gtactccgct cgaggacagt   2460
actccgctcg gaggacagta ctccgatccg tcagatctgc aagacccttc ctctatataa   2520
ggaagttcat ttcatttgga gaggacacgc tgaaccatgg aagtctgcaa ttgtattgaa   2580
ccgcaatggc cagcggatga attgttaatg aaataccaat acatctccga tttcttcatt   2640
gcgattgcgt attttctgat tcctcttgag ttgatttact ttgtgaagaa atcagccgtg   2700
tttccgtata gatgggtact tgttcagttt ggtgctttta tcgttcttta tggagcaact   2760
catcttatta acttatggac tttcactacg cattcgagaa ccgtgcgct tgtgatgact   2820
accgcgaagg tgttaaccgc tgttgtctcg tgtgctactg cgttgatgct tgttcatatt   2880
attcctgatc ttttgagtgt taagactcgg gagcttttct tgaaaataa agctgctgag   2940
ctcgatagag aaatgggatt gattcgaact caggaagaaa ccggaaggca tgtgagaatg   3000
ttgactcatg agattagaag cacttttgat agacatacta ttttaaagac tacacttgtt   3060
gagcttggta ggacattagc tttggaggag tgtgcattgt ggatgcctac tagaactggg   3120
```

```
ttagagctac agctttctta tacacttcgt catcaacatc ccgtggagta tacggttcct    3180
attcaattac cggtgattaa ccaagtgttt ggtactagta gggctgtaaa aatatctcct    3240
aattctcctg tggctaggtt gagacctgtt tctgggaaat atatgctagg ggaggtggtc    3300
gctgtgaggg ttccgcttct ccacctttct aattttcaga ttaatgactg gcctgagctt    3360
tcaacaaaga gatatgcttt gatggttttg atgcttcctt cagatagtgc aaggcaatgg    3420
catgtccatg agttggaact cgttgaagtc gtcgctgatc aggtggctgt agctctctca    3480
catgctgcga tcctagaaga gtcgatgcga gctaggacc ttctcatgga gcagaatgtt    3540
gctcttgatc tagctagacg agaagcagaa acagcaatcc gtgcccgcaa tgatttccta    3600
gcggttatga accatgaaat gcgaacaccg atgcatgcga ttattgcact ctcttcctta    3660
ctccaagaaa cggaactaac ccctgaacaa agactgatgg tggaaacaat acttaaaagt    3720
agtaaccttt tggcaacttt gatgaatgat gtcttagatc tttcaaggtt agaagatgga    3780
agtcttcaac ttgaacttgg gacattcaat cttcatacat tatttagaga ggtcctcaat    3840
ctgataaagc ctatagcggt tgttaagaaa ttacccatca cactaaatct tgcaccagat    3900
ttgccagaat ttgttgttgg ggatgagaaa cggctaatgc agataatatt aaatatagtt    3960
ggtaatgctg tgaaattctc caaacaaggt agtatctccg taaccgctct tgtcaccaag    4020
tcagacacac gagctgctga cttttttgtc gtgccaactg ggagtcattt ctacttgaga    4080
gtgaaggtaa aagactctgg agcaggaata aatcctcaag acattccaaa gattttcact    4140
aaatttgctc aaacacaatc tttagcgacg agaagctcgg gtggtagtgg gcttggcctc    4200
gccatctcca agaggtttgt gaatctgatg gagggtaaca tttggattga gagcgatggt    4260
cttggaaaag gatgcacggc tatctttgat gttaaacttg ggatctcaga acgttcaaac    4320
gaatctaaac agtcgggcat accgaaagtt ccagccattc cccgacattc aaatttcact    4380
ggacttaagg ttcttgtcat ggatgagaac ggggtaagta aatggtgac gaagggactt    4440
cttgtacacc ttgggtgcga agtgaccacg gtgagttcaa acgaggagtg tctccgagtt    4500
gtgtcccatg agcacaaagt ggtcttcatg gacgtgtgca tgcccggggt cgaaaactac    4560
caaatcgctc tccgtattca cgagaaattc acaaaacaac gccaccaacg gccactactt    4620
gtggcactca gtggtaacac tgacaaatcc acaaaagaga aatgcatgag ctttggtctt    4680
gacggtgtgt tgctcaaacc cgtatcacta gacaacataa gagatgttct gtctgatctt    4740
ctcgagcccc gggtactgta cgagtaagcg gccgctaggg catgtctaga agtccgcaaa    4800
aatcaccagt ctctctctac aaatctatct ctctctattt ttctccagaa taatgtgtga    4860
gtagttccca gataagggaa ttagggttct tatagggttt cgctcatgtg ttgagcatat    4920
aagaaaccct tagtatgtat ttgtatttgt aaaatacttc tatcaataaa atttctaatt    4980
cctaaaacca aaatccagtg actgcaggca tgcaagctta tcgataccgt cgacgattga    5040
tgcatgttgt caatcaattg gcaagtcata aaatgcatta aaaaatattt tcatactcaa    5100
ctacaaatcc atgagtataa ctataattat aaagcaatga ttagaatctg acaaggattc    5160
tggaaaatta cataaaggaa agttcataaa tgtctaaaac acaagaggac atacttgtat    5220
tcagtaacat ttgcagcttt tctaggtctg aaaatatatt tgttgcctag tgaataagca    5280
taatggtaca actacaagtg ttttactcct catattaact tcggtcatta gaggccacga    5340
tttgacacat ttttactcaa aacaaaatgt ttgcatatct cttataattt caaattcaac    5400
acacaacaaa taagagaaaa aacaaataat attaatttga gaatgaacaa aaggaccata    5460
tcattcatta actcttctcc atccattttcc atttcacagt tcgatagcga aaaccgaata    5520
```

```
aaaaacacag taaattacaa gcacaacaaa tggtacaaga aaaacagttt tcccaatgcc    5580
ataatactca aactcagtag gattctggtg tgtgcgcaat gaaactgatg cattgaactt    5640
gacgaacgtt gtcgaaaccg atgatacgaa cgaaagctct agaggatcaa ttcgagctct    5700
taggtcgacc cacgtttgcc aaaaccaact cctgctctcc ttttttgtcg tgcttctact    5760
ctttcagggc ttggcaatcc agttttttct tcgtacttct tttctagggc ctctagctct    5820
tcacgaatgc tatcaagaac ttgatccgtc attctgtcaa agaagagaac tccctccaga    5880
tggtcgtatt cgtgctgaaa gattcgtgca ggtaaacgtg atagactgat tgaaaatctt    5940
tcaccagtaa tatcccttgc atcaatcttg acagattgtg gtcgaacaac ttcagcatag    6000
atccccggga aggagaggca tccttcatca aacggtacta atttatcgga atatttcttg    6060
attttcggat ttacaaggac aatttctttt ccttctccag gctctccagc tggattaaac    6120
accatgagtt gaacattgag acctacttgt ggtgctgaga gcccaatgcc atccgttttg    6180
tacataacat caaacatagc atcaaccaag ttctttaaat tctcgtcaaa aatatcaatc    6240
ctcttgttct tagcccgtag tataggatcc ggatactcaa caatcttcaa aggcgtctca    6300
aattgaacat cagtagctga agctacttta tcgtctttac gcgagacgcg ctttacttct    6360
gcgcggaccg aagatgtcag aggactggtc cggttcacag tagagcagaa cgtgaccgtg    6420
gatttgagcc gaccataacc ggcagagaga gtagtagctc ggcgagataa aaccggtagg    6480
agtatgcgag agagtggtgg agcttggagg aagcagttac agacggctcc catggtggaa    6540
gtatttgaaa gaaaattaaa aataaaaaga tccgctcgag gatccaagct tagatgagag    6600
atttcgattc cgattttgat ttcgattccg attttgattt cgattgatct cttccttctg    6660
atttgtgttc cttatataag gaaattcttg tgggattaga cgtcatggct tacgtcattt    6720
ccttcgtcct gttgctcact gattgagctg tgagtggagg gaccactgga agatgcttca    6780
ctaattttct tagtggaggg accggcttca catgcttcac acaagtggct gtcgggcatc    6840 atcttttta gcttttgaca aagcaatgtt ttagtggtgg ctcccactct tatcttcaac    6900
attattatct tatcttcaaa ggacgataag atgttgatgt ctgtggacga agttgggatt    6960
agacgtcatg gcttacgtca tttccttcgt cctgttgctc actgattgag ctgtgagtgg    7020
agggaccact ggaagatgct tcactaattt tcttagtgga gggaccggct tctcatgctt    7080
cacacaagtg gctgtcgggc atcatctttt ttagcttttg acaaagcaat gttttagtgg    7140
gggctcccac tctatcttc aacattatta tcttatcttc aaaggacgat aagatgttga    7200
tgtctgtgga cgaagttgac gaatttcg                                      7228
```

<210> SEQ ID NO 6
<211> LENGTH: 7222
<212> TYPE: DNA
<213> ORGANISM: Artificial
<220> FEATURE:
<223> OTHER INFORMATION: p1003 cassette

<400> SEQUENCE: 6

```
atagtttaaa ctgaaggcgg gaaacgacaa tctgatccaa gctcaagcta agcttgcatg      60
cctgcaggat atcgtggatc caagcttgcc acgtgccgcc acgtgccgcc acgtgccgcc     120
acgtgcctct agaggatcca tctccactga cgtaagggat gacgcacaat cccactatcc     180
ttcgcaagac ccttcctcta tataaggaag ttcatttcat ttggagagga cacgctggga     240
tccccaccat ggatccgcca ccatgctagc ccaccatgaa gctactgtct tctatcgaac     300
aagcatgcga tatttgccga cttaaaaagc tcaagtgctc caaagaaaaa ccgaagtgcg     360
```

```
ccaagtgtct gaagaacaac tgggagtgtc gctactctcc caaaaccaaa aggtctccgc    420
tgactagggc acatctgaca gaagtggaat caaggctaga aagactggaa cagctatttc    480
tactgatttt tcctcgagaa gaccttgaca tgattttgaa aatggattct ttacaggata    540
taaaagcatt gttaacagga ttatttgtac aagataatgt gaataaagat gccgtcacag    600
atagattggc ttcagtggag actgatatgc ctctaacatt gagacagcat agaataagtg    660
cgacatcatc atcggaagag agtagtaaca aaggtcaaag acagttgact gtatccatgg    720
cccccccgac cgatgtcagc ctgggggacg aactccactt agacggcgag gacgtggcga    780
tggcgcatgc cgacgcgcta gacgatttcg atctggacat gttggggggac ggggattccc    840 caggtccggg atttaccccc cacgactccg cccctacgg cgctctggat atggccgact    900
tcgagtttga gcagatgttt accgatgccc ttggaattga cgagtacggt gggaagcttc    960
taggtacctc tagaagaata tcgtggcctg agtgcgtagt acccgagact cagtgcgcca    1020
tgaagcggaa agagaagaaa gcacagaagg agaaggacaa actgcctgtc agcacgacga    1080
cggtggacga ccacatgccg cccattatgc agtgtgaacc tccacctcct gaagcagcaa    1140
ggattcacga agtggtccca aggtttctct ccgacaagct gttggagaca aaccggcaga    1200
aaaacatccc ccagttgaca gccaaccagc agttccttat cgccaggctc atctggtacc    1260
aggacgggta cgagcagcct tctgatgaag atttgaagag gattacgcag acgtggcagc    1320
aagcggacga tgaaaacgaa gagtcggaca ctcccttccg ccagatcgtg gagatgacta    1380
tcctcacggt ccaacttatc gtggagttcg cgaagggatt gccagggttc gccaagatct    1440
cgcagcctga tcaaattacg ctgcttaagg cttgctcaag tgaggtaatg atgctccgag    1500
tcgcgcgacg atacgatgcg gcctccgaca gtgttctgtt cgcgaacaac caagcgtaca    1560
ctcgcgacaa ctaccgcaag gctggcatgg cctacgtcat cgaggatcta ctgcacttct    1620
gccggtgcat gtactctatg gcgttggaca acatccatta cgcgctgctc acggctgtcg    1680
tcatcttttc tgaccggcca gggttggagc agccgcaact ggtggaagag atccagcggt    1740
actacctgaa tacgctccgc atctatatcc tgaaccagct gagcgggtcg gcgcgttcgt    1800
ccgtcatata cggcaagatc ctctcaatcc tctctgagct acgcacgctc ggcatgcaaa    1860
actccaacat gtgcatctcc ctcaagctca agaacagaaa gctgccgcct ttcctcgagg    1920
agatctggga tgtggcggac atgtcgcaca cccaaccgcc gcctatcctc gagtccccca    1980
cgaatctcta gcccctgcgc gcacgcatcg ccgatgccgc gtccggccgc gctgctctga    2040
gaattcgata tcaagcttct agacccgggc tgcagagatc tacgcgttaa gcttaattcc    2100
cgatcgttca aacatttggc aataaagttt cttaagattg aatcctgttg ccggtcttgc    2160
gatgattatc atataatttc tgttgaatta cgttaagcat gtaataatta acatgtaatg    2220
catgacgtta tttatgagat gggtttttat gattagagtc ccgcaattat acatttaata    2280
cgcgatagaa aacaaaatat agcgcgcaaa ctaggataaa ttatcgcgcg cggtgtcatc    2340
tatgttacta gatcggggac tagtaaggcc ggccgcttgg atccgctcgg aggacagtac    2400
tccgctcgga ggacagtact ccgctcggag gacagtactc cgctcgagga cagtactccg    2460
ctcggaggac agtactccga tccgtcagat ctgcaagacc cttcctctat ataaggaagt    2520
tcatttcatt tggagaggac acgctgaacc atggaagtct gcaattgtat tgaaccgcaa    2580
tggccagcgg atgaattgtt aatgaaatac caatacatct ccgatttctt cattgcgatt    2640
gcgtattttt cgattcctct tgagttgatt tactttgtga agaaatcagc cgtgtttccg    2700
tatagatggg tacttgttca gtttggtgct tttatcgttc tttatggagc aactcatctt    2760
```

```
attaacttat ggactttcac tacgcattcg agaaccgtgg cgcttgtgat gactaccgcg    2820
aaggtgttaa ccgctgttgt ctcgtgtgct actgcgttga tgcttgttca tattattcct    2880
gatcttttga gtgttaagac tcgggagctt ttcttgaaaa ataaagctgc tgagctcgat    2940
agagaaatgg gattgattcg aactcaggaa gaaaccggaa ggcatgtgag aatgttgact    3000
catgagatta gaagcacttt agatagacat actattttaa agactacact tgttgagctt    3060
ggtaggacat tagctttgga ggagtgtgca ttgtggatgc ctactagaac tgggttagag    3120
ctacagcttt cttatacact tcgtcatcaa catcccgtgg agtatacggt tcctattcaa    3180
ttaccggtga ttaaccaagt gtttggtact agtagggctg taaaaatatc tcctaattct    3240
cctgtggcta ggttgagacc tgtttctggg aaatatatgc taggggaggt ggtcgctgtg    3300
agggttccgc ttctccacct ttctaatttt cagattaatg actggcctga gctttcaaca    3360
aagagatatg ctttgatggt tttgatgctt ccttcagata gtgcaaggca atggcatgtc    3420
catgagttgg aactcgttga agtcgtcgct gatcaggtgg ctgtagctct ctcacatgct    3480
gcgatcctag aagagtcgat gcgagctagg gaccttctca tggagcagaa tgttgctctt    3540
gatctagcta gacgagaagc agaaacagca atccgtgccc gcaatgattt cctagcggtt    3600
atgaaccatg aaatgcgaac accgatgcat gcgattattg cactctcttc cttactccaa    3660
gaaacggaac taccccctga acaaagactg atggtgaaaa caatacttaa aagtagtaac    3720
cttttggcaa cttttgatgaa tgatgtctta gatctttcaa ggttagaaga tggaagtctt    3780
caacttgaac ttgggacatt caatcttcat acattattta gagaggtcct caatctgata    3840
aagcctatag cggttgttaa gaaattaccc atcacactaa atcttgcacc agatttgcca    3900
gaatttgttg ttggggatga gaaacggcta atgcagataa tattaaatat agttggtaat    3960
gctgtgaaat tctccaaaca aggtagtatc tccgtaaccg ctcttgtcac caagtcagac    4020
acacgagctg ctgactttt tgtcgtgcca actgggagtc atttctactt gagagtgaag    4080
gtaaaagact ctggagcagg aataaatcct caagacattc caaagatttt cactaaattt    4140
gctcaaacac aatctttagc gacgagaagc tcggtggta gtgggcttgg cctcgccatc    4200
tccaagaggt ttgtgaatct gatggagggt aacatttgga ttgagagcga tggtcttgga    4260
aaaggatgca cggctatctt tgatgttaaa cttgggatct cagaacgttc aaacgaatct    4320
aaacagtcgg gcataccgaa agttccagcc attccccgac attcaaattt cactggactt    4380
aaggttcttg tcatggatga gaacggggta agtagaatgg tgacgaaggg acttcttgta    4440
caccttgggt gcgaagtgac cacggtgagt tcaaacgagg agtgtctccg agttgtgtcc    4500
catgagcaca aagtggtctt catggacgtg tgcatgcccg gggtcgaaaa ctaccaaatc    4560
gctctccgta ttcacgagaa attcacaaaa caacgccacc aacggccact acttgtggca    4620
ctcagtggta acactgacaa atccacaaaa gagaaatgca tgagctttgg tcttgacggt    4680
gtgttgctca aacccgtatc actagacaac ataagagatg ttctgtctga tcttctcgag    4740
ccccgggtac tgtacgagta agcggccgct agggcatgtc tagaagtccg caaaaatcac    4800
cagtctctct ctacaaatct atctctctct attttctcc agaataatgt gtgagtagtt    4860
cccagataag ggaattaggg ttcttatagg gtttcgctca tgtgttgagc atataagaaa    4920
cccttagtat gtatttgtat ttgtaaaata cttctatcaa taaatttct aattcctaaa    4980 accaaaatcc agtgactgca ggcatgcaag cttatcgata ccgtcgacga ttgatgcatg    5040
ttgtcaatca attggcaagt cataaaatgc attaaaaaat attttcatac tcaactacaa    5100
atccatgagt ataactataa ttataaagca atgattagaa tctgacaagg attctggaaa    5160
```

```
attacataaa ggaaagttca taaatgtcta aaacacaaga ggacatactt gtattcagta     5220
acatttgcag cttttctagg tctgaaaata tatttgttgc ctagtgaata agcataatgg     5280
tacaactaca agtgttttac tcctcatatt aacttcggtc attagaggcc acgatttgac     5340 acattttac  tcaaaacaaa atgtttgcat atctcttata atttcaaatt caacacacaa     5400
caaataagag aaaaaacaaa taatattaat ttgagaatga acaaaaggac catatcattc     5460
attaactctt ctccatccat ttccatttca cagttcgata gcgaaaaccg aataaaaaac     5520
acagtaaatt acaagcacaa caaatggtac aagaaaaaca gttttcccaa tgccataata     5580
ctcaaactca gtaggattct ggtgtgtgcg caatgaaact gatgcattga acttgacgaa     5640
cgttgtcgaa accgatgata cgaacgaaag ctctagagga tcaattcgag ctcttaggtc     5700
gacccacgtt tgccaaaacc aactcctgct ctcctttttt gtcgtgcttc tactctttca     5760
gggcttggca atccagtttt ttcttcgtac ttcttttcta gggcctctag ctcttcacga     5820
atgctatcaa gaacttgatc cgtcattctg tcaaagaaga gaactccctc cagatggtcg     5880
tattcgtgct gaaagattcg tgcaggtaaa cgtgatagac tgattgaaaa tctttcacca     5940
gtaatatccc ttgcatcaat cttgacagat tgtggtcgaa caacttcagc atagatcccc     6000
gggaaggaga ggcatccttc atcaaacggt actaatttat cggaatattt cttgattttc     6060
ggatttacaa ggacaatttc ttttccttct ccaggctctc cagctggatt aaacaccatg     6120
agttgaacat tgagacctac ttgtggtgct gagagcccaa tgccatccgt tttgtacata     6180
acatcaaaca tagcatcaac caagttcttt aaattctcgt caaaaatatc aatcctcttg     6240
ttcttagccc gtagtatagg atccggatac tcaacaatct tcaaaggcgt ctcaaattga     6300
acatcagtag ctgaagctac tttatcgtct ttacgcgaga cgcgctttac ttctgcgcgg     6360
accgaagatg tcagaggact ggtccggttc acagtagagc agaacgtgac cgtggatttg     6420
agccgaccat aaccggcaga gagagtagta gctcggcgag ataaaaccgg taggagtatg     6480
cgagagagtg gtggagcttg gaggaagcag ttacagacgg ctcccatggt ggaagtattt     6540
gaaagaaaat taaaaataaa aagatccgct cgaggatcca agcttagatg agagatttcg     6600
attccgattt tgatttcgat tccgatttg  atttcgattg atctcttcct tctgatttgt     6660 gttcctttata taaggaaatt cttgtgggat tagacgtcat ggcttacgtc atttccttcg     6720
tcctgttgct cactgattga gctgtgagtg gagggaccac tggaagatgc ttcactaatt     6780
ttcttagtgg agggaccggc ttcacatgct tcacacaagt ggctgtcggg catcatcttt     6840
tttagctttt gacaaagcaa tgttttagtg gtggctccca ctcttatctt caacattatt     6900
atcttatctt caaggacga  taagatgttg atgtctgtgg acgaagttgg gattagacgt     6960
catggcttac gtcatttcct tcgtcctgtt gctcactgat tgagctgtga gtggagggac     7020
cactggaaga tgcttcacta attttcttag tggagggacc ggcttctcat gcttcacaca     7080
agtggctgtc gggcatcatc tttttagct tttgacaaag caatgtttta gtgggggctc     7140
ccactcttat cttcaacatt attatcttat cttcaaagga cgataagatg ttgatgtctg     7200
tggacgaagt tgacgaattt cg                                             7222
```

<210> SEQ ID NO 7
<211> LENGTH: 2211
<212> TYPE: DNA
<213> ORGANISM: Artificial
<220> FEATURE:
<223> OTHER INFORMATION: mutated Arabidopsis thaliana gene Etr 1-1

<400> SEQUENCE: 7

```
atggaagtct gcaattgtat tgaaccgcaa tggccagcgg atgaattgtt aatgaaatac      60
caatacatct ccgatttctt cattgcgatt gcgtattttt cgattcctct tgagttgatt     120
tactttgtga agaaatcagc cgtgtttccg tatagatggg tacttgttca gtttggtgct     180
tttatcgttc tttatggagc aactcatctt attaacttat ggactttcac tacgcattcg     240
agaaccgtgg cgcttgtgat gactaccgcg aaggtgttaa ccgctgttgt ctcgtgtgct     300
actgcgttga tgcttgttca tattattcct gatcttttga gtgttaagac tcgggagctt     360
ttcttgaaaa ataaagctgc tgagctcgat agagaaatgg gattgattcg aactcaggaa     420
gaaaccggaa ggcatgtgag aatgttgact catgagatta aagcactttt agatagacat     480
actattttaa agactacact tgttgagctt ggtaggacat tagctttgga ggagtgtgca     540
ttgtggatgc ctactagaac tgggttagag ctacagcttt cttatacact tcgtcatcaa     600
catcccgtgg agtatacggt tcctattcaa ttaccggtga ttaaccaagt gtttggtact     660
agtagggctg taaaaatatc tcctaattct cctgtggcta ggttgagacc tgtttctggg     720
aaatatatgc taggggaggt ggtcgctgtg agggttccgc ttctccacct ttctaatttt     780
cagattaatg actggcctga gctttcaaca aagagatatg ctttgatggt tttgatgctt     840
ccttcagata gtgcaaggca atggcatgtc catgagttgg aactcgttga agtcgtcgct     900
gatcaggtgg ctgtagctct ctcacatgct gcgatcctag aagagtcgat gcagctagg      960 gaccttctca tggagcagaa tgttgctctt gatctagcta dacgagaagc agaaacagca    1020
atccgtgccc gcaatgattt cctagcggtt atgaaccatg aaatgcgaac accgatgcat    1080
gcgattattg cactctcttc cttactccaa gaaacggaac taaccctga caaagactg     1140 atggtggaaa caatacttaa aagtagtaac cttttggcaa cttttgatgaa tgatgtctta    1200 gatctttcaa ggttagaaga tggaagtctt caacttgaac ttgggacatt caatcttcat    1260
acattattta gagaggtcct caatctgata aagcctatag cggttgttaa gaaattaccc    1320
atcacactaa atcttgcacc agatttgcca gaatttgttg ttggggatga gaacggcta    1380 atgcagataa tattaaatat agttggtaat gctgtgaaat ctccaaaaca aggtagtatc    1440
tccgtaaccg ctcttgtcac caagtcagac acacgagctg ctgactttt tgtcgtgcca    1500 actgggagtc atttctactt gagagtgaag gtaaaagact ctggagcagg aataaatcct    1560
caagacattc caaagatttt cactaaattt gctcaaacac aatctttagc gacgagaagc    1620
tcgggtggta gtgggcttgg cctcgccatc tccaagaggt ttgtgaatct gatgggagggt    1680 aacatttgga ttgagagcga tggtcttgga aaaggatgca cggctatctt tgatgttaaa    1740
cttgggatct cagaacgttc aaacgaatct aaacagtcgg gcataccgaa agttccagcc    1800
attccccgac attcaaattt cactggactt aaggttcttg tcatggatga aacgggggta    1860
agtagaatgg tgacgaaggg acttcttgta caccttgggt gcgaagtgac cacggtgagt    1920
tcaaacgagg agtgtctccg agttgtgtcc catgagcaca aagtggtctt catggacgtg    1980
tgcatgcccg gggtcgaaaa ctaccaaatc gctctccgta ttcacgagaa attcacaaaa    2040
caacgccacc aacggccact acttgtggca ctcagtggta acactgacaa atccacaaaa    2100
gagaaatgca tgagctttgg tcttgacggt gtgttgctca acccgtatc actagacaac    2160 ataagagatg ttctgtctga tcttctcgag ccccgggtac tgtacgagta a             2211
```

<210> SEQ ID NO 8
<211> LENGTH: 259
<212> TYPE: PRT
<213> ORGANISM: Choristoneura fumiferana

<400> SEQUENCE: 8

```
Leu Thr Ala Asn Gln Gln Phe Leu Ile Ala Arg Leu Ile Trp Tyr Gln
1               5                   10                  15

Asp Gly Tyr Glu Gln Pro Ser Asp Glu Asp Leu Lys Arg Ile Thr Gln
            20                  25                  30

Thr Trp Gln Gln Ala Asp Asp Glu Asn Glu Glu Ser Asp Thr Pro Phe
        35                  40                  45

Arg Gln Ile Thr Glu Met Thr Ile Leu Thr Val Gln Leu Ile Val Glu
    50                  55                  60

Phe Ala Lys Gly Leu Pro Gly Phe Ala Lys Ile Ser Gln Pro Asp Gln
65                  70                  75                  80

Ile Thr Leu Leu Lys Ala Cys Ser Ser Glu Val Met Met Leu Arg Val
                85                  90                  95

Ala Arg Arg Tyr Asp Ala Ala Ser Asp Ser Val Leu Phe Ala Asn Asn
            100                 105                 110

Gln Ala Tyr Thr Arg Asp Asn Tyr Arg Lys Ala Gly Met Ala Tyr Val
        115                 120                 125

Ile Glu Asp Leu Leu His Phe Cys Arg Cys Met Tyr Ser Met Ala Leu
130                 135                 140

Asp Asn Ile His Tyr Ala Leu Leu Thr Ala Val Val Ile Phe Ser Asp
145                 150                 155                 160

Arg Pro Gly Leu Glu Gln Pro Gln Leu Val Glu Ile Gln Arg Tyr
                165                 170                 175

Tyr Leu Asn Thr Leu Arg Ile Tyr Ile Leu Asn Gln Leu Ser Gly Ser
            180                 185                 190

Ala Arg Ser Ser Val Ile Tyr Gly Lys Ile Leu Ser Ile Leu Ser Glu
        195                 200                 205

Leu Arg Thr Leu Gly Met Gln Asn Ser Asn Met Cys Ile Ser Leu Lys
    210                 215                 220

Leu Lys Asn Arg Lys Leu Pro Pro Phe Leu Glu Glu Ile Trp Asp Val
225                 230                 235                 240

Ala Asp Met Ser His Thr Gln Pro Pro Ile Leu Glu Ser Pro Thr
                245                 250                 255

Asn Leu Gly
```

<210> SEQ ID NO 9
<211> LENGTH: 259
<212> TYPE: PRT
<213> ORGANISM: Choristoneura fumiferana

<400> SEQU

```
                    100                 105                 110
Gln Ala Tyr Thr Arg Asp Asn Tyr Arg Lys Ala Gly Met Ala Tyr Val
            115                 120                 125

Ile Glu Asp Leu Leu His Phe Cys Arg Cys Met Tyr Ser Met Ala Leu
        130                 135                 140

Asp Asn Ile His Tyr Ala Leu Leu Thr Ala Val Val Ile Phe Ser Asp
145                 150                 155                 160

Arg Pro Gly Leu Glu Gln Pro Gln Leu Val Glu Glu Ile Gln Arg Tyr
                165                 170                 175

Tyr Leu Asn Thr Leu Arg Ile Tyr Ile Leu Asn Gln Leu Ser Gly Ser
            180                 185                 190

Ala Arg Ser Ser Val Ile Tyr Gly Lys Ile Leu Ser Ile Leu Ser Glu
        195                 200                 205

Leu Arg Thr Leu Gly Met Gln Asn Ser Asn Met Cys Ile Ser Leu Lys
210                 215                 220

Leu Lys Asn Arg Lys Leu Pro Pro Phe Leu Glu Glu Ile Trp Asp Val
225                 230                 235                 240

Ala Asp Met Ser His Thr Gln Pro Pro Ile Leu Glu Ser Pro Thr
            245                 250                 255

Asn Leu Gly

<210> SEQ ID NO 10
<211> LENGTH: 24
<212> TYPE: DNA
<213> ORGANISM: Artificial
<220> FEATURE:
<223> OTHER INFORMATION: synthetic E1b minimal promoter

<400> SEQUENCE: 10
tatataatgg atccccgggt accg                                              24

<210> SEQ ID NO 11
<211> LENGTH: 20
<212> TYPE: DNA
<213> ORGANISM: Artificial
<220> FEATURE:
<223> OTHER INFORMATION: 18s Foward Primer

<400> SEQUENCE: 11
cgtccctgcc ctttgtacac                                                   20

<210> SEQ ID NO 12
<211> LENGTH: 21
<212> TYPE: DNA
<213> ORGANISM: Artificial
<220> FEATURE:
<223> OTHER INFORMATION: 18s Reverse Primer

<400> SEQUENCE: 12
acacttcacc ggaccattca a                                                 21

<210> SEQ ID NO 13
<211> LENGTH: 19
<212> TYPE: DNA
<213> ORGANISM: Artificial
<220> FEATURE:
<223> OTHER INFORMATION: 18s Probe

<400> SEQUENCE: 13
ccgcccgtcg ctcctaccg                                                    19
```

```
<210> SEQ ID NO 14
<211> LENGTH: 21
<212> TYPE: DNA
<213> ORGANISM: Artificial
<220> FEATURE:
<223> OTHER INFORMATION: ACC Oxidase(aco) Forward Primer

<400> SEQUENCE: 14
gttgtagaag gacgcgatgg a                                              21

<210> SEQ ID NO 15
<211> LENGTH: 21
<212> TYPE: DNA
<213> ORGANISM: Artificial
<220> FEATURE:
<223> OTHER INFORMATION: ACC Oxidase(aco) Reverse Primer

<400> SEQUENCE: 15
caggtacaag agcgtcatgc a                                              21

<210> SEQ ID NO 16
<211> LENGTH: 20
<212> TYPE: DNA
<213> ORGANISM: Artificial
<220> FEATURE:
<223> OTHER INFORMATION: ACC Oxidase(aco) Probe

<400> SEQUENCE: 16
tcctgttccc gctgggctgc                                                20
```

COMPOSITIONS AND METHODS FOR THE MODIFICATION OF PHYSIOLOGICAL RESPONSES IN PLANTS

CROSS-REFERENCE TO RELATED APPLICATIONS

This application is a continuation of international patent application PCT/US08/75708 filed on Sep. 9, 2008, which claims the benefit of the priority of U.S. provisional patent application No. 60/973,057, filed Sep. 17, 2007.

BACKGROUND OF THE INVENTION

The phytohormone ethylene is a signaling molecule that regulates numerous physiological processes throughout the life cycle of plants, including responses during germination, flower and fruit development, as well as the response of the plants to a variety of environmental stressors, such as drought, heat, excessive salinity, and disease (see, e.g., Chen et al, 2005, Annals of Botany, 95:901-915; Czarny et al, 2006 Biotechnol. Adv., 24:410-419). Ethylene biosynthesis pathways and signaling/regulatory pathways and networks are well described. For example, see FIGS. 1 and 2 in Wang et al, "Ethylene Biosynthesis and Signaling Networks", in The Plant Cell, 2002 (eds. American Society of Plant Biologists) pages S131-S151. Commercially, a common way to regulate ethylene response in plants, including fruits and vegetables and flowers, involves the application of a chemical to the plant, fruit, flower or vegetable, such as 1-methylcyclopropene (1-MCP; AgroFresh, Inc.). 1-MCP is a compound generally delivered as a gas that is used as a plant growth regulator that prevents ethylene from attaching to its receptors in plant tissues. Its application thereby increases the ethylene insensitivity of the plant. The temporary ablation of ethylene sensitivity can increase the plants' resistance or tolerance to stress, delay ripening, senescence, or flowering, among other commercially valuable manipulations of plant growth.

More recently, proposals to transform plant cells genetically with modified ethylene response receptors or other proteins involved in the ethylene response in plants have been suggested, such as in e.g., U.S. Pat. No. 6,294,716; US Patent Application Publication Nos. 2006/0200875, 2005/0066389, 2005/0060772 and 2004/0128719, among others. Such systems are directed to expression of a variety of mutated genes in the ethylene pathways. These systems generally employ a variety of suggested promoters to drive expression of the proteins, including constitutive promoters and tissue-specific promoters.

While the use of chemically regulated gene expression systems have been proposed for use in plants generically (M. Padidim 2003 Curr. Opin Plant Biol., 6(2):169-77), many such systems are experimental only, or have been reported to have certain disadvantages. Among these disadvantages are the use of toxic or volatile inducers, low induction levels, poor translocation/movement in the plant, a slow ability to "turn-off" the expression of the gene or insufficient specificity to an inducer that is non-toxic to plants, among other issues. Such gene expression systems are not universally useful in all plants and selection of the operable components and their assembly is often challenging.

In the examples of the prior art, expression of the ethylene pathway genes is typically always on in all tissues and parts of the plant or is always on in specific tissues of the plant. However, tissue-specific promoters or low level constitutive promoters can be leaky or induced by an undesirable inducer. Such conventional promoters do not permit tight regulation of hormonal expression in the plant. The timing, duration and level of expression of the ethylene pathway genes are critical for normal physiological function. The induction of ethylene insensitivity at will and for a determined period of time has not been successfully demonstrated by the prior art.

There remains a need in the art for compositions and methods that permit controllable temporal regulation of hormonal responses of plants, e.g., ethylene sensitivity, which are safe for use in agricultural crops and foodstuffs, as well as in other plants.

SUMMARY OF THE INVENTION

Figure 1:
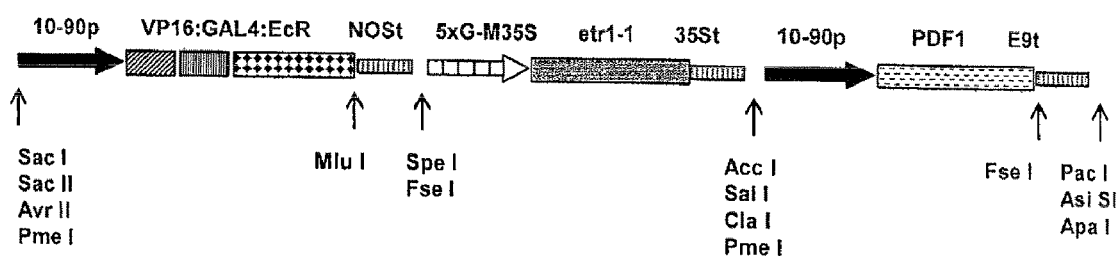
FIG. 1 is a schematic drawing of a plasmid p185 containing the gene expression system for expression of a mutant gene in the ethylene response pathway, etr1-1. Above the construct are references to the components of the activation cassette, i.e., the 10-90p constitutive promoter, the VP16 activation domain, the GAL4 DNA binding domain, the ecdysone receptor (EcR) ligand binding domain, and the NOS terminator. Also above the construct are references to the components of the target cassette, including the five repeats of the GAL4 response element (5×G), the minimal 35S promoter (M35S), the sequence of the mutant etr1-1 gene, and the 35S terminator (35St). Following the target cassette is the optional plant selectable marker PDF 1 followed by an rbcS terminator, which are useful in determining whether the gene construct was stably integrated into the plant cell. Below the construct are the positions and identifications of the conventional enzymatic cleavage sites.

The compositions and methods described herein meet the need in the art by providing transgenic plants, plant cells, tissues, organs, fruits or flowers in which regulation of ethylene sensitivity may be reliably and safely controlled, e.g., in a temporal, qualitative and/or quantitative manner. These compositions and methods demonstrate tight regulation of gene expression, and thus hormonal expression, and are safe for use in agricultural crops and foodstuffs, as well as in other commercially valuable plants.

In one aspect, a gene expression system is provided for controllable expression of ethylene response in a plant cell. This system includes an activation cassette and a target cassette, which may be present on one or more plasmids. The activation cassette comprises a suitable promoter, a DNA-binding domain (DBD), an ecdysone receptor ligand binding domain (EcRLBD); and an activation domain (AD). The target cassette comprises a chemically inducible promoter comprising, in operative association, the response element to which the DBD binds and a minimal promoter responsive to the AD. This chemically inducible promoter controls expression of a target nucleic acid sequence that encodes a selected protein or fragment thereof that modifies sensitivity to ethylene in the plant (in sense or antisense orientation). Interaction among components of the two cassettes, when in the plant cell with an inducing composition, modulates expression of the protein and selectively modulates ethylene sensitivity in the plant cell. The modulation in protein expression is controllable by the timing, the concentration and the duration of the application of the inducing composition. The inducing composition may be absorbed by, and translocated within, the cells of the plant, where it interacts with the activation domain to turn on the chemically inducible promoter of the target cassette. Thus, this system permits controllable and selective modulation of ethylene sensitivity in the plant cell via expression of the target nucleic acid sequence.

In another aspect, a plant cell is provided which expresses, stably or transiently, this above-described gene expression system.

In another aspect, a plant tissue or organ is provided which expresses, stably or transiently, this above-described gene expression system.

In another aspect, a transgenic plant is provided which expresses, stably or transiently, this above-described gene expression system.

In another aspect, a method for producing such a transgenic plant or portion thereof involves transforming at least one cell in the plant with the gene expression system described herein; generating a plant cell, tissue, organ or intact plant from the transformed plant cell; and selecting a plant cell, tissue, organ or intact plant which demonstrates controllable modulation of ethylene insensitivity when the plant cell, tissue, organ or intact plant is contacted with an inducing composition. The modulation in protein expression is controlled by the timing, the concentration, and the duration of the application of the inducing composition. The inducing composition may be absorbed by and translocated within, the plant cell, tissue, organ or intact plant.

In a further aspect, a method for controlling ethylene sensitivity in a plant involves applying an effective amount of an inducing composition to the cells of a transgenic plant or portion thereof, the plant comprising cells that stably or transiently express the gene expression system described herein. The inducing composition may be absorbed by, and translocated within, the plant cells. In the presence of the inducing composition, the response of the plant cells to ethylene is decreased for a selected time; and the response of the plant cells to ethylene is increased after a selected time by depriving the plant of the inducer. The modulation in protein expression is controlled by the timing, the concentration, and the duration of the application of the inducing composition.

Other aspects and advantages of these methods and compositions are described further in the following detailed description.

DETAILED DESCRIPTION OF THE INVENTION

The compositions and methods described herein address the need in the art for compositions and methods for the controllable regulation of ethylene sensitivity in plants. More specifically, the compositions and methods described herein permit the deliberate variation of expression levels based on use of selected amounts of a chemical inducer. Such an ability to manipulate hormonal regulation of the plants provides an agricultural benefit for the growth and ripening of crops, among other benefits described below.

I. GENE EXPRESSION SYSTEM

A gene expression or modulation system is employed for stable or transient expression in a plant cell. The components of such a system include at least two gene expression cassettes, each of which is capable of being expressed in a plant cell.

In one embodiment, the first gene expression cassette, referred to as the activation cassette, comprises a polynucleotide which is expressible in a plant cell encoding the following components under the control of a suitable promoter and in operative association therewith: (a) a DNA-binding domain (DBD) that recognizes a response element associated with a gene whose expression is to be modulated, i.e., a gene that encodes a selected protein that modifies sensitivity to ethylene in the plant; (b) a ligand binding domain (LBD) comprising an ecdysone receptor ligand binding domain (EcRLBD) or functional fragment thereof; and (c) an activation or transactivation domain (AD) which is activated in the presence of an inducing composition suitable for application to plants. In one embodiment, the components in the activation cassette are present in the following order 5' to 3': the LBD is downstream of the DBD, which is downstream of the AD. In another embodiment, the components in the activation cassette are present in the following order 5' to 3': the LBD is downstream of the AD, which is downstream of the DBD. In another embodiment, the components in the activation cassette are present in the following order 5' to 3': the DBD is downstream of the LBD, which is downstream of the AD. In another embodiment, the components in the activation cassette are present in the following order 5' to 3': the DBD is downstream of the AD, which is downstream of the LBD. In another embodiment, the components in the activation cassette are present in the following order 5' to 3': the AD is downstream of the LBD, which is downstream of the DBD. In another embodiment, the components in the activation cassette are present in the following order 5' to 3': the AD is downstream of the DBD, which is downstream of the LBD. The activation cassette also includes a terminator positioned preferable at the 3' terminus of the cassette. The specific identities of these components are discussed below.

The second gene expression cassette, i.e., the target cassette, comprises a polynucleotide encoding the following components. One component is a chemically inducible promoter comprising, in operative association, the response element (RE) to which the DBD of the protein encoded by the activation cassette binds and a minimal promoter responsive to the AD of the activation cassette. The other component is a target nucleic acid sequence that encodes a selected protein that modifies sensitivity to ethylene in plant, or encodes a functional fragment of such a protein. The nucleic acid sequence may be in sense orientation in certain embodiments. In other embodiments, the nucleic acid sequence may be in antisense orientation. The inducible promoter is in control of the expression of the selected protein-encoding or antisense sequence.

In another embodiment, the activation and/or target cassettes further comprise terminator sequences, such as downstream of the nucleic acid sequence encoding the protein or its antisense sequence, and an optional selectable marker. Such markers are well-known and used for selecting cells that take up the genes in the presence of an antibiotic or other chemical.

These optional components are discussed in more detail below.

This gene expression system operates so that the components of the activation cassette and the target cassette, when in the plant cell and in cooperation with an inducing composition, modulate expression of the selected protein. Modulation or regulation of the selected protein selectively modulates ethylene sensitivity in the plant cell. For example, one modulation involves increasing ethylene sensitivity of the plant cell. In another embodiment, the ethylene sensitivity of the plant cell is decreased. This expression of a protein that modulates the ethylene pathway is controlled in the plant cell by the interaction of the components of the gene expression system with the inducing composition. The inducing composition may be absorbed by, and/or translocated within, the cells of the plant.

Figure 2:
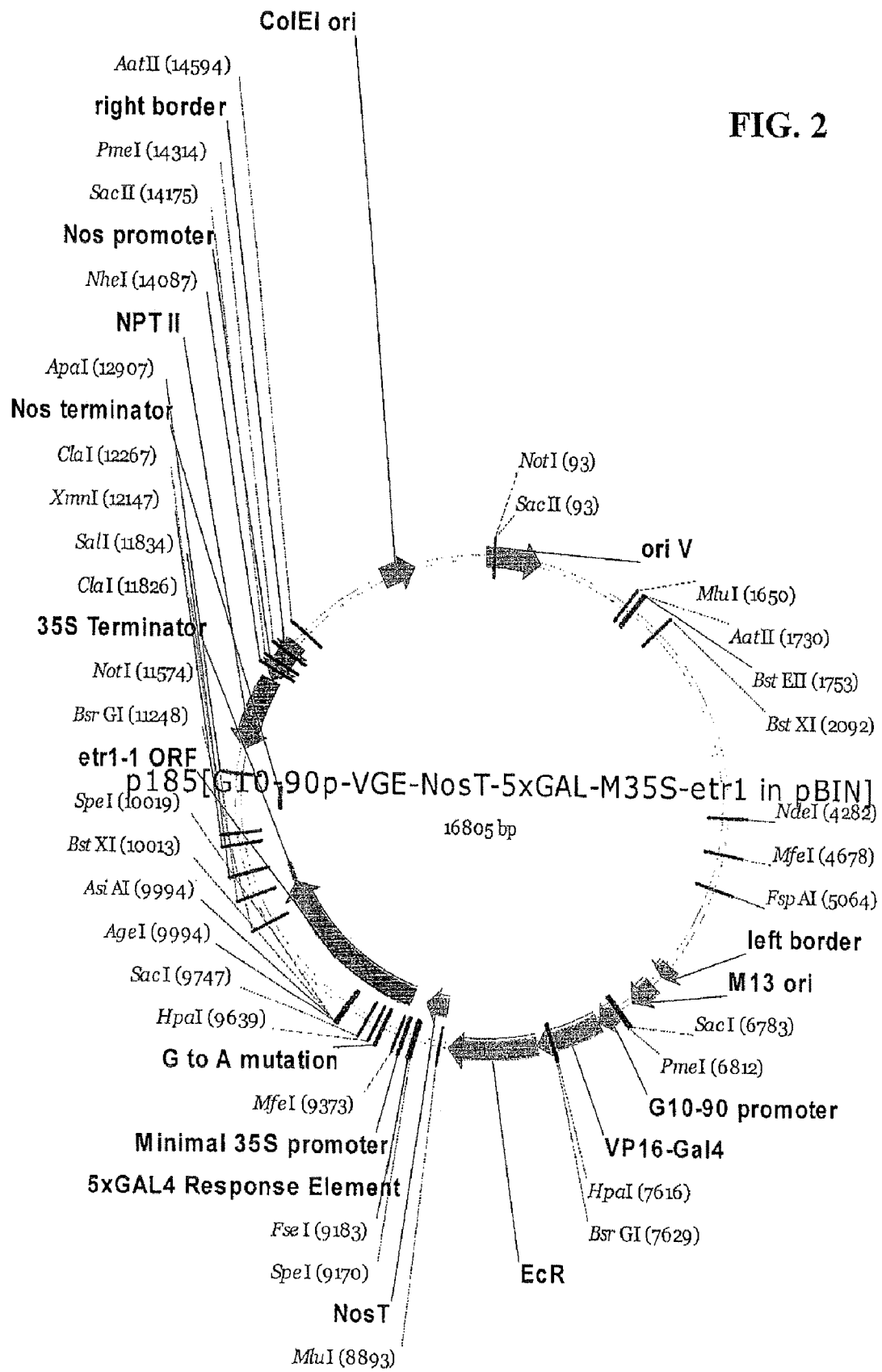
FIG. 2 is a schematic of an example of a plasmid designated p185 carrying both an activation cassette and a targeting cassette of the gene expression system (G10-90p-VGE-NosT-5×GAL-M335S-etr1) with the components of the cassettes identified as disclosed above in FIG. 1 and in SEQ ID NO: 1, with the G to A mutation shown for the mutant gene etr1-1, and the cleavage sites identified by nucleic acid position in parentheses. The cassette portions of this plasmid are reported in SEQ ID NO: 1. The commercially available plasmid backbone is not provided in the sequence listing or figures, as it may be readily replaced with other plasmid backbones.
Figure 3:
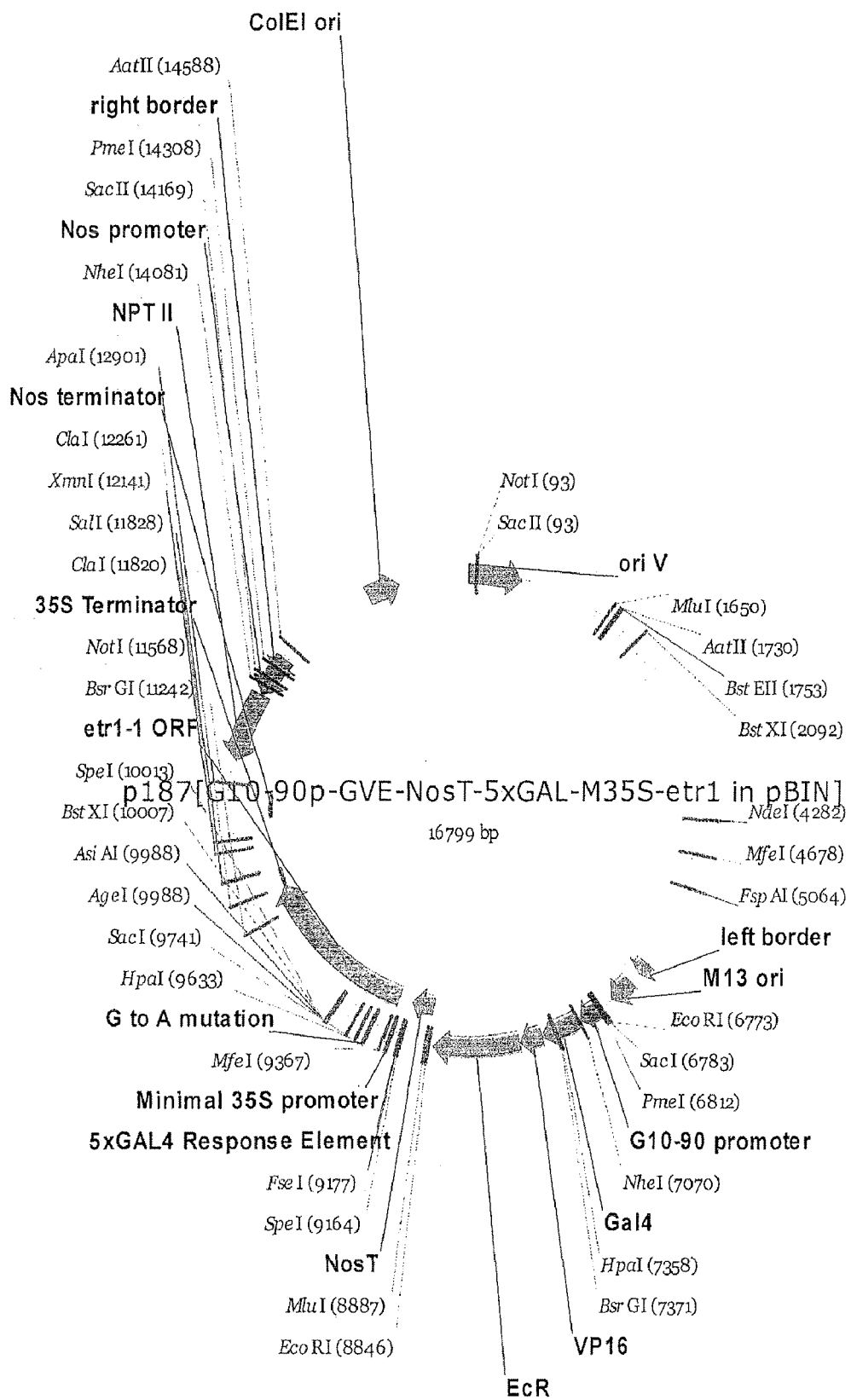
FIG. 3 is a schematic of an example of a plasmid designated p187, which contains both an activation cassette and target cassette [G10-90p-GVE-NosT-5×GAL-M35S-etr1], for expression of etr1-1 using GVE receptor-mediated inducible expression of etr1-1. The cassette portions of this plasmid are reported in SEQ ID NO: 2. The commercially available plasmid backbone is not provided in the sequence listing or figures, as it may be readily replaced with other plasmid backbones.

In one embodiment of this system, the first cassette and second cassette are present on a single plasmid, such as that of FIGS. 2 and 3. In another embodiment, the first and second cassettes are present on separate plasmids.

In another embodiment of the gene expression system, a first gene expression cassette can contain a DBD and a first LBD; a second cassette can contain the AD and a second, different LBD; and a third cassette comprises a polynucleotide that encodes the response element to which the DBD of the first polypeptide binds, a promoter that is activated by the AD of the second cassette; and the target gene whose expression is to be modulated. In this system, the AD and DBD are operationally linked to two different proteins which in the presence of inducing composition activate the target gene expression. In one embodiment, the first LBD can be an EcR LBD, while the second LBD can be an LBD from a retinoid X receptor. In another embodiment, the second LBD can be an EcR LBD, while the first LBD can be an LBD from a retinoid X receptor. Such a construct is described in U.S. Pat. No. 7,091,038 or US patent publication No. US 2005/0266457, published Dec. 1, 2005.

For use in understanding the following components, the term "operably linked" or "operatively linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from a nucleic acid or polynucleotide. In one embodiment, expression refers to translation of mRNA into a protein or polypeptide. In another embodiment, expression may be decreased or downregulated by antisense (i.e., expressing a sequence complementary to the mRNA "sense" sequence which then binds to the "sense" strand and prevents expression thereof), cosuppression (i.e., the overexpression of a gene sequence, generally a transgene, which causes suppression of a homologous endogenous gene) or RNA interference (RNAi, i.e., a process wherein RNA introduced to a cell ultimately causes the degradation of the complementary cellular mRNA and leads to a reduction in gene activity). In another embodiment, the components of the gene expression system may be transiently expressed in the plant cell. In another embodiment, the components of the gene expression system may be stably expressed by integration into a chromosome of the plant cell. The selection of transient vs. stable integrated expression may be selected by one of skill in the art in generating and using the gene expression system as described herein.

The terms "cassette", "expression cassette" and "gene expression cassette" refer to a segment of DNA that can be inserted into a nucleic acid or polynucleotide at specific restriction sites or by homologous recombination. The segment of DNA comprises a polynucleotide that encodes a polypeptide of interest or provides a gene in the antisense orientation, and the cassette and restriction sites are designed to ensure insertion of the cassette in the proper reading frame for transcription and translation in either direction. These vectors or plasmids may optionally comprise a polynucleotide that encodes a polypeptide of interest and having elements in addition to the polynucleotide that facilitate transformation of a particular host cell. Such cassettes in certain embodiments also comprise elements that allow for enhanced expression of a polynucleotide encoding a polypeptide of interest in a host cell. These elements may include, but are not limited to: a promoter, a minimal promoter, an enhancer, a response element, a terminator sequence, a polyadenylation sequence, and the like.

All other terms used herein employ the conventional meaning in the art, unless otherwise indicated. See, for example, the definition of the terms in U.S. Pat. No. 7,091,038.

A. The Promoter of the Activation Cassette

In one embodiment of the system, the promoter of the activation cassette is a nucleic acid sequence (DNA or RNA) that is capable of controlling the expression of the DBD, LBD and AD sequences within a transformed plant cell. In general, these three primary components of the activation cassette are located 3' to the selected promoter sequence. The promoter sequence consists of proximal and more distal upstream elements referred to as enhancers. An "enhancer" is a DNA sequence that can stimulate promoter activity and may be an innate element of the promoter or a heterologous element inserted to enhance the level or specificity of a promoter. Useful promoters in this context may be derived in their entirety from a native gene, or be composed of different elements derived from different promoters found in nature, or even comprise synthetic DNA segments.

In one embodiment, the promoter of the activation cassette is a constitutive promoter, e.g., a promoter that causes a gene to be expressed in most cell types at most times, so that the plant cell transformed with this cassette is continually producing the activation cassette components. For example, certain constitutive promoters that are useful in this activation cassette include, without limitation, the exemplified G10-90 promoter, the cauliflower mosaic virus 35S promoter, the Cassava mosaic virus promoter, the figwort mosaic virus promoter, the Badnavirus promoter, *Mirabilis* mosaic virus promoter, the Rubisco promoter, the Actin promoter, or the ubiquitin promoter.

In still other embodiments promoters that direct the expression of a gene in different tissues or cell types ("tissue specific", "cell specific" or "plant organ-specific promoters") may be used for this purpose. Desirably such promoters are native to or functional in plant tissues and plant cells, or mutant versions of promoters native to or functional in plant tissues and plant cells. However promoters for other tissues and cells from other sources, e.g., mammalian, invertebrate, etc, that operate in plant cells may also be employed for this purpose. Still other embodiments employ promoters that express the components at different stages of development ("developmentally-specific promoters" or "cell differentiation-specific promoter"), or in response to different environmental or physiological conditions. For an extensive list of tissue-specific promoters, see Gallie, US Patent Application Publication No. 2005/0066389, which describes seed-specific promoters derived from the following genes: MACI from maize (Sheridan, 1996 Genetics 142:1009-1020); Cat3 from maize (GenBank No. L05934, Abler 1993 Plant Mol. Biol. 22:10131-10138); vivparous-1 from *Arabidopsis* (Genbank No. U93215); atmyc1 from *Arabidopsis* (Urao, 1996 Plant Mol. Biol. 32:571-576; Conceicao 1994 Plant 5:493-505); napA and BnCysP1 from *Brassica napus* (GenBank No. J02798, Josefsson, 1987 JBL 26:12196-12201, Wan et al., 2002 Plant J 30:1-10); and the napin gene family from *Brassica napus* (Sjodahl, 1995 Planta 197:264-271). Fruit specific promoters include the promoter from the CYP78A9 gene (Ito and Meyerowitz, 2000 Plant Cell 12:1541-1550). Other tissue-specific promoters include the ovule-specific BEL1 gene described in Reiser, 1995 Cell 83:735-742, GenBank No. U39944; Ray, 1994 Proc. Natl. Acad. Sci. USA 91:5761-5765 and the egg and central cell specific FIE1 promoter. Sepal and petal specific promoters include the *Arabidopsis* floral homeotic gene APETALA1 (AP1) (Gustafson Brown, 1994 Cell 76:131-143; Mandel, 1992 Nature 360: 273-277), a related promoter, for AP2 (see, e.g., Drews, 1991 Cell 65:991-1002; Bowman, 1991 Plant Cell 3:749-758). Another useful promoter is that controlling the expression of the unusual floral organs (ufo) gene of *Arabidopsis* (Bossinger, 1996 Development 122:1093-1102). Additional tissue specific promoters include a maize pollen specific promoter (Guerrero, 1990 Mol. Gen. Genet. 224:161-168); see also promoters described by Wakeley, 1998 Plant Mol. Biol. 37:187-192; Ficker, 1998 Mol. Gen. Genet. 257:132-142; Kulikauskas, 1997 Plant Mol. Biol. 34:809-814; Treacy, 1997 Plant Mol. Biol. 34:603-611). Useful promoters include those from the FUL gene (Mandel and Yanofsky, 1995 Plant Cell, 7:1763-1771) and promoters from the SHP1 and SHP2 genes (Flanagan et al. 1996 Plant J 10:343-353; Savidge et al., 1995 Plant Cell 7(6):721-733). Promoters may be derived from the TA29 gene (Goldberg et al., 1995 Philos Trans. R. Soc. Lond. B. Biol. Sci. 350:5-17).

Other suitable promoters include those from the gene encoding the 2S storage protein from *Brassica napus* (Dasgupta, 1993 Gene 133:301-302); the 2 s seed storage protein gene family from *Arabidopsis*; the gene encoding oleosin 20 kD from *Brassica napus*, GenBank No. M63985; the genes encoding oleosin A, Genbank No. U09118, and, oleosin B, Genbank No. U09119, from soybean; the gene encoding oleosin from *Arabidopsis*, Genbank No. Z17657; the gene encoding oleosin 18 kD from maize, GenBank No. J05212 and Lee, 1994 Plant Mol. Biol. 26:1981-1987; and the gene encoding low molecular weight sulphur rich protein from soybean (Choi, 1995 Mol Gen, Genet. 246:266-268). The tissue specific E8 promoter from tomato and promoters from the ATHB-8, AtPIN1, AtP5K1 or TED3 genes (Baima et al., 2001 Plant Physiol. 126:643-655, Galaweiler et al., 1998 Science 282:2226-2230; Elge et al., 2001 Plant J. 26:561-571; Igarashi et al., 1998 Plant Mol. Biol. 36:917-927) are also useful.

A tomato promoter active during fruit ripening, senescence and abscission of leaves and, to a lesser extent, of flowers can be used (Blume, 1997 Plant J. 12:731-746). Other exemplary promoters include the pistil specific promoter in the potato (*Solanum tuberosum* L.) SK2 gene, encoding a pistil specific basic endochitinase (Ficker, 1997 Plant Mol. Biol. 35:425-431); the Blec4 gene from pea (*Pisum sativum* cv. Alaska), active in epidermal tissue of vegetative and floral shoot apices of transgenic alfalfa. A variety of promoters specifically active in vegetative tissues including promoters controlling patatin, the major storage protein of the potato tuber (e.g., Kim, 1994 Plant Mol. Biol. 26:603-615; and Martin, 1997 Plant J. 11:53-62), and the ORF13 promoter from *Agrobacterium rhizogenes* (Hansen, 1997 Mol. Gen. Genet. 254:337-343) can be used. Other useful vegetative tissue-specific promoters include: the tarin promoter of the gene encoding a globulin from a major taro (*Colocasia esculenta* L. Schott) corn protein family, tarin (Bezerra, 1995 Plant Mol. Biol. 28:137-144); the curculin promoter (de Castro, 1992 Plant Cell 4:1549-1559) and the promoter for the tobacco root specific gene TobRB7 (Yamamoto, 1991 Plant Cell 3:371-382). Leaf-specific promoters include the ribulose biphosphate carboxylase (RBCS) promoters, the tomato RBCS1, RBCS2 and RBCS3A genes (Meier, 1997 FEBS Lett. 415: 91-95). A ribulose bisphosphate carboxylase promoter expressed almost exclusively in mesophyll cells in leaf blades and leaf sheaths at high levels (Matsuoka, 1994 Plant J. 6:311-319), the light harvesting chlorophyll a/b binding protein gene promoter (Shiina, 1997 Plant Physiol. 115:477-483; Casal, 1998 Plant Physiol. 116:1533-1538), the *Arabidopsis thaliana* myb-related gene promoter (Atmyb5; Li, 1996 FEBS Lett. 379:117-121), and the Atmyb5 promoter (Busk, 1997 Plant J. 11:1285-1295) are useful promoters.

Useful vegetative tissue-specific promoters include meristematic (root tip and shoot apex) promoters, e.g., the "SHOOTMERISTEMLESS" and "SCARECROW" promoters (Di Laurenzio, 1996 Cell 86:423-433; and, Long, 1996 Nature 379:66-69. Another useful promoter controls the expression of 3-hydroxyl-3-methylglutaryl coenzyme A reductase HMG2 gene (see, e.g., Enjuto, 1995 Plant Cell. 7:517-527). Also useful are kn1 related genes from maize and other species which show meristem specific expression, see, e.g., Granger, 1996 Plant Mol. Biol. 31:373-378; Kerstetter, 1994 Plant Cell 6:1877-1887; Hake, 1995 Philos. Trans. R. Soc. Lond. B. Biol. Sci. 350:45-51, e.g., the *Arabidopsis thaliana* KNAT1 or KNAT2 promoters (see, e.g., Lincoln, 1994 Plant Cell 6:1859-1876).

In certain embodiments of the activation cassette, the promoters may be inducible or regulatable, e.g., causes expression of the nucleic acid sequence following exposure or treatment of the cell with an agent, biological molecule, chemical, ligand, light, or some other stimulus. A non-limiting list of such inducible promoters include the PR 1-a promoter, prokaryotic repressor-operator systems, and higher eukaryotic transcription activation systems, such as described in detail in U.S. Pat. No. 7,091,038. Such promoters include the tetracycline ("Tet") and lactose ("Lac") repressor-operator systems from *E. coli*. Other inducible promoters include the drought-inducible promoter of maize; the cold, drought, and high salt inducible promoter from potato, the senescence inducible promoter of *Arabidopsis*, SAG 12, and the embryogenesis related promoters of LEC1, LEC2, FUS3, AtSERK1, and AGL15, all known to those of skill in the art. Still other plant promoters which are inducible upon exposure to plant hormones, such as auxins or cytokinins, are useful in this context, as described in US Patent Application Publication No. US2005/0066389 and U.S. Pat. No. 6,294,716.

Essentially for the purposes of the activation cassette, any promoter capable of driving expression of the sequences of the DBD, LBD and AD is suitable, including but not limited to: viral promoters, bacterial promoters, plant promoters, synthetic promoters, constitutive promoters, tissue specific promoter, developmental specific promoters, inducible promoters, light regulated promoters; pathogenesis or disease related promoters, cauliflower mosaic virus 19S, cauliflower mosaic virus 35S, CMV 35S minimal, cassava vein mosaic virus (CsVMV), figwort mosaic virus, Badnavirus, *Mirabilis* mosaic virus, chlorophyll a/b binding protein, ribulose 1,5- bisphosphate carboxylase, shoot-specific, root specific, chitinase, stress inducible, rice tungro bacilliform virus, plant super-promoter, potato leucine aminopeptidase, nitrate reductase, alcohol dehydrogenase, sucrose synthase, mannopine synthase, nopaline synthase, octopine synthase, ubiquitin, zein protein, actin and anthocyanin promoters In a preferred embodiment of the invention, the promoter is selected from the group consisting of a cauliflower mosaic virus 35S promoter, a cassava vein mosaic virus promoter, and a cauliflower mosaic virus 35S minimal promoter, a figwort mosaic virus promoter, a Badnavirus promoter, a *Mirabilis* mosaic virus, a ubiquitin (Ubc) promoter, and an actin promoter.

B. The DBD

As used herein, the term "DNA binding domain" comprises a minimal polypeptide sequence of a DNA binding protein, up to the entire length of a DNA binding protein, so long as the DNA binding domain functions to associate with a particular response element. The DNA binding domain binds, in the presence or absence of a ligand, to the DNA sequence of the RE to initiate or suppress transcription of downstream gene(s) under the regulation of this RE. In certain embodiments of the gene expression units, the DBD is located in the activation cassette, while the response element is located in the targeting cassette.

The DNA binding domain can be any DNA binding domain with a known response element, including synthetic and chimeric DNA binding domains, or analogs, combinations, or modifications thereof. In certain embodiments, the DBD is a GAL4 DBD, a LexA DBD, a transcription factor DBD, a Group H nuclear receptor member DBD, a steroid/thyroid hormone nuclear receptor superfamily member DBD, or a bacterial LacZ DBD. More preferably, the DBD is an insect ecdysone receptor DBD, a GAL4 DBD (see the sequence illustrated in the plasmids of the examples herein), or a LexA DBD. The sequences for such DBDs are publically available and described in publications such as U.S. Pat. No. 7,091,038 or US Patent Application Publication No. 2005/0266457. In other embodiments, the DBDs useful in this cassette include, without limitation, DNA binding domains obtained from the cI promoter, or lac promoter, which are also publically available sequences.

C. The Ecdysone LBD and Optional Second LBD

In certain embodiments of the gene expression system, the ecdysone receptor (EcR) LBD comprises all or a portion of an invertebrate ecdysone receptor or mutant thereof. EcR is a member of the nuclear steroid receptor super family that is characterized by signature DNA and ligand binding domains, and an activation domain (Koelle et al. 1991, Cell, 67:59 77; see also, U.S. Pat. No. 6,245,531 (Stanford). Ecdysone receptors are responsive to a number of steroidal compounds such as ponasterone A and muristerone A and non-steroidal compounds. EcR has five modular domains, A/B (transactivation), C (DNA binding, heterodimerization), D (Hinge, heterodimerization), E (ligand binding, heterodimerization and transactivation and F (transactivation) domains. Some of these domains such as A/B, C and E retain their function when they are fused to other proteins. Suitable portions of EcR for use as the LBD in the gene expression system described herein include domains D, E and F.

Preferably, the EcR is a Lepidopteran EcR, a Dipteran EcR, an Arthropod EcR, a Homopteran EcR and a Hemipteran EcR. More preferably, the EcR for use is a spruce budworm *Choristoneura fumiferana* EcR ("CfEcR"), a *Tenebrio molitor* EcR ("TmEcR"), a *Manduca sexta* EcR ("MsEcR"), a *Heliothies virescens* EcR ("HvEcR"), a silk moth *Bombyx mori* EcR ("BmEcR"), a fruit fly *Drosophila melanogaster* EcR ("DmEcR"), a mosquito *Aedes aegypti* EcR ("AaEcR"), a blowfly *Lucilia capitata* EcR ("LcEcR"), a Mediterranean fruit fly *Ceratitis capitata* EcR ("CcEcR"), a locust *Locusta migratoria* EcR ("LmEcR"), an aphid *Myzus persicae* EcR ("MpEcR"), a fiddler crab *Uca pugilator* EcR ("UpEcR"), an ixodid tick *Amblyomma americanum* EcR ("AmaEcR"), a white fly *Bamecia argentifoli* EcR ("BaEcR"), or a green leafhopper *Nephotetix cincticeps* EcR ("NcEcR"), among others. Even more preferably, the LBD is from spruce budworm (*Choristoneura fumiferana*) EcR ("CfEcR") or fruit fly *Drosophila melanogaster* EcR ("DmEcR"). Sequences for such EcRs are publically available and described in such publications as, e.g., U.S. Pat. No. 7,091,038; International Patent Publication No. WO 97/38117 and U.S. Pat. Nos. 6,333,318, 6,265,173 and 5,880,333.

Another suitable mutant ecdysone receptor is one containing a mutation as described in the above cited US patent application publication No. 2005/0266457, e.g., a Group H nuclear receptor ligand binding domain comprising at least one mutation, wherein the mutation is at a position equivalent to or analogous to certain specific amino acid residues identified in that publication. More specifically, the ecdysone LBD that contains a mutation at amino acid position T to V mutation at SEQ ID NO: 9 is a particularly desirable EcRLBD used in the following examples. The sequence of this mutant is also reproduced as amino acid no. 990 to 1997 of SEQ ID NO: 1 herein. This mutant EcR LBD is referred to as T52V, but describes a mutation of Thr to Val at amino acid position 335 in the full-length Cf EcR. This mutation of EcR LBD is employed in the gene expression cassettes used in the examples below. Still others of the EcR LBDs described therein may be useful in the gene expression system described herein. In another embodiment, the mutant ecdysone receptor LBD is that described in U.S. Pat. No. 6,245,531 (Stanford).

In one specific embodiment, the LBD is from a truncated EcR polypeptide. The EcR polypeptide truncation results in a deletion of at least 1, 2, 3, 4, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, or 265 amino acids. Preferably, the EcR polypeptide truncation results in a deletion of at least a partial polypeptide domain. More preferably, the EcR polypeptide truncation results in a deletion of at least an entire polypeptide domain. In a specific embodiment, the EcR polypeptide truncation results in a deletion of at least an A/B-domain, a C-domain, a D-domain, an F-domain, an A/B/C-domains, an A/B/1/2-C-domains, an A/B/C/D-domains, an A/B/C/D/F-domains, an A/B/F-domains, an A/B/C/F-domains, a partial E domain, or a partial F domain. A combination of several complete and/or partial domain deletions may also be performed.

In another embodiment, the Group H nuclear receptor ligand binding domain is encoded by a polynucleotide comprising a codon mutation that results in a substitution of a) amino acid residue 48, 51, 52, 54, 92, 95, 96, 109, 110, 119, 120, 125, 128, 132, 219, 223, 234, or 238 of SEQ ID NO: 8, b) amino acid residues 96 and 119 of SEQ ID NO: 8, c) amino acid residues 110 and 128 of SEQ ID NO: 8, d) amino acid residues 52 and 110 of SEQ ID NO: 8, e) amino acid residues 107, 110, and 127 of SEQ ID NO: 8, or f) amino acid residues 52, 107 and 127 of SEQ ID NO: 8. In another embodiment, the Group H nuclear receptor ligand binding domain is encoded by a polynucleotide comprising codon mutations that results in substitution of amino acid residues 107 and 127 and insertion of amino acid 259 of SEQ ID NO: 8. SEQ ID NO: 8 is shown in FIG. 11.

In another specific embodiment, the Group H nuclear receptor ligand binding domain is encoded by a polynucleotide comprising a codon mutation that results in a substitution of a) an asparagine, arginine, tyrosine, tryptophan, leucine or lysine residue at a position equivalent to analogous to amino acid residue 48 of SEQ ID NO: 8, b) a methionine, asparagines or leucine residue at a position equivalent or analogous to amino acid residue 51 of SEQ ID NO: 8, c) a leucine, proline, methionine, arginine, tryptophan, glycine, glutamine or glutamic acid residue at a position equivalent or analogous to amino acid residue 52 of SEQ ID NO: 8, d) a tryptophan or threonine at a position equivalent or analogous to amino acid 54 of SEQ ID NO: 8, e) a leucine or glutamic acid at a position equivalent or analogous to amino acid 92 of SEQ ID NO: 8, f) a histidine, methionine or tryptophan residue at a position equivalent or analogous to amino acid residue 95 of SEQ ID NO: 8, g) a leucine, serine, glutamic acid or tryptophan residue at a position equivalent or analogous to amino acid residue 96 of SEQ ID NO: 8, h) a tryptophan, proline, leucine, methionine or asparagine at a position equivalent or analogous to amino acid 109 of SEQ ID NO: 8, i) a glutamic acid, tryptophan or asparagine residue at a position equivalent or analogous to amino acid residue 110 of SEQ ID NO: 8, j) a phenylalanine at a position equivalent or analogous to amino acid 119 of SEQ ID NO: 8, k) a tryptophan or methionine at a position equivalent or analogous to amino acid 120 of SEQ ID NO: 8, l) a glutamic acid, proline, leucine, cysteine, tryptophan, glycine, isoleucine, asparagine, serine, valine or arginine at a position equivalent or analogous to amino acid 125 of SEQ ID NO: 8, m) a phenylalanine at a position equivalent or analogous to amino acid 128 of SEQ ID NO: 8, n) a methionine, asparagine, glutamic acid or valine at a position equivalent or analogous to amino acid 132 of SEQ ID NO: 8, o) an alanine, lysine, tryptophan or tyrosine residue at a position equivalent or analogous to amino acid residue 219 of SEQ ID NO: 8, p) a lysine, arginine or tyrosine residue at a position equivalent or analogous to amino acid residue 223 of SEQ ID NO: 8, q) a methionine, arginine, tryptophan or isoleucine at a position equivalent or analogous to amino acid 234 of SEQ ID NO: 8, r) a proline, glutamic acid, leucine, methionine or tyrosine at a position equivalent or analogous to amino acid 238 of SEQ ID NO: 8, s) a phenylalanine residue at a position equivalent or analogous to amino acid 119 of SEQ ID NO: 8 and a threonine at a position equivalent or analogous to amino acid 96 of SEQ ID NO: 8, t) a proline residue at a position equivalent or analogous to amino acid 110 of SEQ ID NO: 8 and a phenylalanine residue at a position equivalent or analogous to amino acid 128 of SEQ ID NO: 8, u) a valine residue at a position equivalent or analogous to amino acid 52 of SEQ ID NO: 8 and a praline residue at a position equivalent or analogous to amino acid 110 of SEQ ID NO: 8, v) an isoleucine residue at a position equivalent or analogous to amino acid 107 of SEQ ID NO: 8, a glutamic acid residue at a position equivalent or analogous to amino acid 127 of SEQ ID NO: 8 and a proline residue at a position equivalent or analogous to amino acid 110 of SEQ ID NO: 8, or w) an isoleucine at a position equivalent or analogous to amino acid 107 of SEQ ID NO: 8, a glutamic acid at a position equivalent or analogous to amino acid 127 of SEQ ID NO: 8 and a valine at a position equivalent or analogous to amino acid 52 of SEQ ID NO: 8. In another embodiment, the Group H nuclear receptor ligand binding domain is encoded by a polynucleotide comprising codon mutations that results in substitution of an isoleucine residue at a position equivalent or analogous to amino acid 107 of SEQ ID NO: 8, a glutamic acid residue at a position equivalent or analogous to amino acid 127 of SEQ ID NO: 8 and insertion of a glycine residue at a position equivalent or analogous to amino acid 259 of SEQ ID NO: 8. In a preferred embodiment, the Group H nuclear receptor ligand binding domain is from an ecdysone receptor.

In still another embodiment, the LBD comprising a substitution mutation is an ecdysone receptor ligand binding domain comprising a substitution mutation encoded by a polynucleotide comprising a codon mutation that results in a substitution mutation selected from the following group. According to this list, the reference F48Y means the LBD of SEQ ID NO: 8 in which phenylalanine at amino acid position 48 of the sequence is replaced by a tyrosine, and so on. Thus, the group includes substitution mutations represented F48Y, F48W, F48L, F48N, F48R, F48K, I51M, I51N, I51L, T52M, T52V, T52L, T52E, T52P, T52R, T52W, T52G, T52Q, M43W, M54T, M92L, M92E, R95H, R95M, R95W, V96L, V96W, V96S, V96E, F109W, F109P, F109P, F109L, F109M, F109N, A110E, A110N, A110W, N119F, Y120W, Y120M, M125P, M125R, M125E, M125L, M125C, M125W, M125G, M125I, M125N, M125S, M125V, V128F, L132M, L132N, L132V, L132E, M219K, M219W, M219Y, M219A, L223K, L223R, L223Y, L234M, L234I, L234R, L234W, W238P, W238E, W238Y, W238M, W238L, N119/V96T, V128F/ A100P, T52V/A110P, V107I/Y127E/T52V, and V107I/ Y127E/A110P substitution mutation of SEQ ID NO: 8. In another specific embodiment, the LBD comprising a substitution mutation is an ecdysone receptor ligand binding domain comprising a substitution mutation encoded by a polynucleotide comprising a codon mutation that results in substitution mutation V107I/Y127E of SEQ ID NO: 8, which further comprises insertion mutation G259 of SEQ ID NO: 8 (V107I/Y127E/G259).

In another embodiment, the LBD is encoded by a polynucleotide that hybridizes to a polynucleotide identified above under hybridization conditions comprising a hybridization step in less than 500 mM salt and at least 37° C., and a washing step in 2×SSPE at least 63° C. In a preferred embodiment, the hybridization conditions comprise less than 200 mM salt and at least 37° C., for the hybridization step. In another preferred embodiment, the hybridization conditions comprise 2×SSPE and 63° C. for both the hybridization and washing steps.

In another specific embodiment, the ligand binding domain comprises a substitution mutation at a position equivalent or analogous to a) amino acid residue 48, 51, 52, 54, 92, 95, 96, 109, 110, 119, 120, 125, 128, 132, 219, 223, 234, or 238 of SEQ ID NO: 8, b) amino acid residues 96 and 119 of SEQ ID NO: 8, c) amino acid residues 110 and 128 of SEQ ID NO: 8, d) amino acid residues 52 and 110 of SEQ ID NO: 8, e) amino acid residues 107, 110, and 127 of SEQ ID NO: 8, or f) amino acid residues 52, 107 and 127 of SEQ ID NO: 8. In another embodiment, the Group H nuclear receptor ligand binding domain comprises substitution mutations that results in substitution mutation at a position equivalent or analogous to amino acid residues 107 and 127 and insertion of amino acid residue 259 of SEQ ID NO: 8.

Preferably, the LBD comprises a substitution of a) an asparagine, arginine, tyrosine, tryptophan, leucine or lysine residue at a position equivalent to analogous to amino acid residue 48 of SEQ ID NO: 8, b) a methionine, asparagine or leucine residue at a position equivalent or analogous to amino acid residue 51 of SEQ ID NO: 8, c) a leucine, proline, methionine, arginine, tryptophan, glycine, glutamine or glutamic acid residue at a position equivalent or analogous to amino acid residue 52 of SEQ ID NO: 8, d) a tryptophan or threonine residue at a position equivalent or analogous to amino acid 54 of SEQ ID NO: 8, e) a leucine or glutamic acid residue at a position equivalent or analogous to amino acid 92 of SEQ ID NO: 8, f) a histidine, methionine or tryptophan residue at a position equivalent or analogous to amino acid residue 95 of SEQ ID NO: 8, g) a leucine, serine, glutamic acid or tryptophan residue at a position equivalent or analogous to amino acid residue 96 of SEQ ID NO: 8, h) a tryptophan, proline, leucine, methionine or asparagine at a position equivalent or analogous to amino acid 109 of SEQ ID NO: 8, i) a glutamic acid, tryptophan or asparagine residue at a position equivalent or analogous to amino acid residue 110 of SEQ ID NO: 8, j) a phenylalanine residue at a position equivalent or analogous to amino acid 119 of SEQ ID NO: 8, k) a tryptophan or methionine residue at a position equivalent or analogous to amino acid 120 of SEQ ID NO: 8, l) a glutamic acid, proline, leucine, cysteine, tryptophan, glycine, isoleucine, asparagine, serine, valine or arginine residue at a position equivalent or analogous to amino acid 125 of SEQ ID NO: 8, m) a phenylalanine residue at a position equivalent or analogous to amino acid 128 of SEQ ID NO: 8, n) a methionine, asparagine, glutamic acid or valine residue at a position equivalent or analogous to amino acid 132 of SEQ ID NO: 8, o) an alanine, lysine, tryptophan or tyrosine residue at a position equivalent or analogous to amino acid residue 219 of SEQ ID NO: 8, p) a lysine, arginine or tyrosine residue at a position equivalent or analogous to amino acid residue 223 of SEQ ID NO: 8, q) a methionine, arginine, tryptophan or isoleucine residue at a position equivalent or analogous to amino acid 234 of SEQ ID NO: 8, r) a proline, glutamic acid, leucine, methionine or tyrosine residue at a position equivalent or analogous to amino acid 238 of SEQ ID NO: 8, s) a phenylalanine residue at a position equivalent or analogous to amino acid 119 of SEQ ID NO: 8 and a threonine residue at a position equivalent or analogous to amino acid 96 of SEQ ID NO: 8, t) a proline residue at a position equivalent or analogous to amino acid 110 of SEQ ID NO: 8 and a phenylalanine residue at a position equivalent or analogous to amino acid 128 of SEQ ID NO: 8, u) a valine residue at a position equivalent or analogous to amino acid 52 of SEQ ID NO: 8 and a proline residue at a position equivalent or analogous to amino acid 110 of SEQ ID NO: 8, v) an isoleucine residue at a position equivalent or analogous to amino acid 107 of SEQ ID NO: 8, a glutamic acid residue at a position equivalent or analogous to amino acid 127 of SEQ ID NO: 8 and a proline residue at a position equivalent or analogous to amino acid 110 of SEQ ID NO: 8, or w) an isoleucine residue at a position equivalent or analogous to amino acid 107 of SEQ ID NO: 8, a glutamic acid residue at a position equivalent or analogous to amino acid 127 of SEQ ID NO: 8 and a valine residue at a position equivalent or analogous to amino acid 52 of SEQ ID NO: 8. In another embodiment, the Group H nuclear receptor ligand binding domain comprises a substitution of an isoleucine residue at a position equivalent or analogous to amino acid 107 of SEQ ID NO: 8, a glutamic acid residue at a position equivalent or analogous to amino acid 127 of SEQ ID NO: 8 and insertion of a glycine residue at a position equivalent or analogous to amino acid 259 of SEQ ID NO: 8.

In certain embodiments of the gene expression system employs a second LBD. The second LBD is not an ecdysone receptor polypeptide, but can be the ligand binding domain of a second nuclear receptor. Such second binding domains include, without limitation a vertebrate retinoid X receptor ligand binding domain, an invertebrate retinoid X receptor ligand binding domain, an ultraspiracle protein ligand binding domain, and a chimeric ligand binding domain comprising two polypeptide fragments, wherein the first polypeptide fragment is from a vertebrate retinoid X receptor ligand binding domain, an invertebrate retinoid X receptor ligand binding domain, or an ultraspiracle protein ligand binding domain, and the second polypeptide fragment is from a different vertebrate retinoid X receptor ligand binding domain, invertebrate retinoid X receptor ligand binding domain, or ultraspiracle protein ligand binding domain. See, e.g, such binding domains described in US Patent Application Publication No. US 2005/0266457. Such LBDs are well known to those of skill in the art and are well described in the literature.

D. The Activation Domain

The activation or transactivation domain (abbreviated "AD") useful in the gene expression system may be any Group H nuclear receptor member AD, steroid/thyroid hormone nuclear receptor AD, synthetic or chimeric AD, polyglutamine AD, basic or acidic amino acid AD, a VP16 AD, a GAL4 AD, an NF-κB AD, a BP64 AD, a B42 acidic activation domain (B42AD), a p65 transactivation domain (p65AD), a glucocorticoid activation domain or an analog, combination, or modification thereof. In a specific embodiment, the AD is a synthetic or chimeric AD, or is obtained from an EcR, a glucocorticoid receptor, VP16, GAL4, NF-κB, or B42 acidic activation domain AD. Preferably, the AD is an EcR AD, a VP16 AD, a B42 AD, or a p65 AD. Sequences for such activation domains are publically available in such publications as U.S. Pat. No. 7,091,038 or in other documents described herein. An exemplary VP16AD is described in plasmids described in the examples herein. Such domains are well known to those of skill in the art and are well described in the literature.

E. The Inducible Promoter of the Target Cassette

In certain embodiments, the inducible promoter of the target cassette is a multicomponent promoter sequence. It comprises a minimal promoter operatively associated with one or more copies of a response element corresponding to the DNA binding domain in the activation cassette. A minimal promoter, as used herein, includes the core promoter (i.e., the sequence that mediates the initiation of transcription) and the 5' untranslated region (5'UTR) without enhancer sequences. Thus, for use in embodiments of the gene expression system, the minimal promoter may be a minimal promoter derived from any promoter described above in Part A for use in the activation cassette. In certain embodiments of target cassettes, desirable minimal promoters include: the cauliflower mosaic virus 35S minimal promoter; a synthetic E1b minimal promoter (SEQ ID NO: 10; see U.S. Pat. No. 7,091,038) and a synthetic TATA minimal promoter (TATATA; see US Patent Application Publication No. US 2005/0228016). Minimal promoters useful in the gene expression systems described herein may be readily selected by one of skill in the art from numerous promoters well described in the literature. The sequence of the 35S minimal promoter is described in the plasmids described in the examples below.

The other portion of the inducible promoter of the target cassette includes a response element ("RE") located 5' or 3' to the minimal promoter. One RE can have two different or identical minimal promoters on either side to express two different proteins. In one embodiment, the RE is operationally or operatively linked to the minimal promoter. A response element is one or more cis-acting DNA elements which confer responsiveness on a promoter mediated through interaction with the DNA-binding domains of the activation cassette. This DNA element may be either palindromic (perfect or imperfect) in its sequence or composed of sequence motifs or half sites separated by a variable number of nucleotides. The half sites can be similar or identical and arranged as either direct or inverted repeats or as a single half site or multimers of adjacent half sites in tandem. Examples of DNA sequences for response elements of the natural ecdysone receptor are described in Cherbas L. et al, 1991 Genes Dev. 5, 120 131; D'Avino P P. et al, 1995 Mol. Cell. Endocrinol, 113:19 and Antoniewski C. et al, 1994 Mol. Cell Biol. 14, 4465-4474, among other publications. The RE may be any response element corresponding to the DNA binding domain in the activation cassette, or an analog, combination, or modification thereof. A single RE may be employed or multiple REs, either multiple copies of the same RE or two or more different REs, may be used in target cassette. The RE can be modified or substituted with response elements for other DNA binding protein domains such as the GAL-4 protein from yeast (see Sadowski, et al. 1988 Nature, 335:563 564) or LexA protein from *E. coli* (see Brent and Ptashne 1985, Cell, 43:729 736), or synthetic response elements specific for targeted interactions with proteins designed, modified, and selected for such specific interactions (see, for example, Kim, et al. 1997 Proc. Natl. Acad. Sci., USA, 94:3616-3620) to accommodate chimeric receptors. In a specific embodiment, the RE is an RE from GAL4 ("GAL4RE"), preferably two or more copies. The examples below demonstrate the use of five copies of the GAL4 RE (i.e, 5×GAL4). However, other suitable RE include, without limitation, LexA, a Group H nuclear receptor RE, a steroid/thyroid hormone nuclear receptor RE, or a synthetic RE that recognizes a synthetic DNA binding domain. In other embodiments, the RE is an ecdysone response element (EcRE), or a LexA RE (operon, "op") comprising a polynucleotide sequence. All such RE are well described in the literature and may be readily selected by one of skill in the art given the teachings of this specification.

In the target cassette, this "inducible promoter" is operatively linked and controls expression of the nucleic acid sequence or gene that modulates ethylene sensitivity, as identified below. The inducible promoter of the target cassette is induced by a chemical inducing composition or inducer which, when in contact with the ligand binding domain of the activation cassette, activates the response element of the minimal promoter.

F. The Nucleic Acid Sequence Encoding a Selected Protein

The nucleic acid sequence useful in this system encodes a selected protein that modifies ethylene sensitivity or ethylene production in the plant. Such a nucleic acid sequence includes, in certain embodiments, the ethylene biosynthesis genes, ACC synthase (ACS), ACC oxidase (ACO) and ACC deaminase (ACD). Other suitable ethylene receptor genes are those wildtype genes that encode the ETR1, ETR2, ERS1, ERS2 and EIN4 proteins. Still other ethylene signaling pathway genes encoding proteins, such as RTE1, CTR1, EIN2, EIN3, EIN3-like (EIL1-5), EIN5, EIN6 and EEN are useful in the gene expression system useful in the methods and plants, plant organs and tissues described herein. Additional nucleic acid sequences which form embodiments of gene expression systems include the ethylene response factors, ERF1, EDF1, EDF2, EDF3 and EDF4, and the EIN3 binding F-box proteins, EBF1 and EBF2. For additional ethylene modulation targets, see also Czarny et al, 2006 Biotech. Advances, 24:410-419; Chen et al, 2005 Annals Bot. 95:901-915; and Ciardi and Klee, 2001, Annals Bot, 88:813-822.

In addition to the use of wildtype, or naturally occurring plant genes, the gene expression system may also employ certain nucleic acid sequences that contain mutations useful in these gene sequences and encoded proteins. An example of such a mutant etr1-1 receptor sequence is identified in SEQ ID NO: 1 from nucleotides 2557 to 4767. A variety of known mutant ethylene receptor proteins are described in the literature, as are methods to create such mutations. See, for example, the mutant receptor disclosed in US Patent Application Publication No. US2004/0128719, as well as the mutations described at paragraphs 0033-0041; and the ACC oxidase sequences of US Patent Application Publication No. US 2005/0066389; and the ETR sequences of US Patent Application Publication No. US 2006/0200875, among others.

In one embodiment of the invention described herein, the wildtype gene for a particular plant is used in the gene expression system and in the methods described herein to control or modulate ethylene sensitivity in the plant. In another embodiment, mutated versions of the wildtype protein that mediates ethylene sensitivity or ethylene production in the plant cell are employed. In still further embodiments, a wildtype of mutated variant of a gene that encodes a protein that modifies ethylene sensitivity or ethylene production in one species of plant cell is used in another species of plant cell, where such use is desirable, e.g., to eliminate potential RNA silencing.

In addition to the use of nucleic acid sequences that encode protein sequences that can be employed to modulate ethylene sensitivity, another component of certain gene express systems useful herein include polynucleotides that are complementary in sequence to the encoding sequences referenced herein. For instance, antisense sequences to a wildtype gene sequence of the many identified above can be expressed by the gene expression system in the plant cell. The transcription of such antisense sequences can modulate ethylene sensitivity by binding to, and thus inactivating, sequences native to the plant.

G. Optional Components

Optional components found in the cassettes of the gene expression system include termination control regions. Such terminator or polyadenylation sequences may also be employed in the activation and target cassettes in certain embodiments of this invention. Such regions are derived from various genes native to the preferred hosts. In one embodiment of the invention, the termination control region comprises or is derived from a synthetic polyadenylation signal, nopaline synthase (nos), cauliflower mosaic virus (CaMV), octopine synthase (ocs), *Agrobacterium*, viral, and plant terminator sequences, or the like.

Selectable markers can include an antibiotic or chemical resistance gene that is able to be selected for based upon its effect, i.e., resistance to an antibiotic, resistance to a herbicide, colorimetric markers, enzymes, fluorescent markers, and the like. Examples of selectable marker genes known and used in the art include: genes providing resistance to ampicillin, streptomycin, gentamycin, kanamycin, hygromycin, actinonin (PDF1 gene), bialaphos herbicide, glyphosate herbicide, sulfonamide, mannose and the like; and genes that are used as phenotypic markers, i.e., anthocyanin regulatory genes, isopentanyl transferase gene, GUS and luciferase.

Other regulatory sequences, such as nucleotide sequences that function as spacer sequences in the plasmids, and other minor regulatory sequences, enzyme cleavage sites, and the like, may also be found in the cassettes or in the plasmids that contain the cassettes for transformation into a plant cell according to certain embodiments described herein.

The appropriate termination sequences, selectable markers, and other conventional plasmid regulatory sequences may be readily selected by one of skill in the art from among numerous such sequences well known to those of skill in the art and well described in the literature given the teachings herein.

H. Inducing Compositions/Inducers Useful for the Gene Expression System

When the gene expression system is expressed in the plant, modulation of the expression of the selected protein and selective modulation of ethylene sensitivity in the plant cell is controllable by use of an inducing composition. In one embodiment, the inducing composition is a chemical that is placed in contact with the cells of the plant. In another embodiment, the inducing composition is a chemical that is absorbed by the cells of the plant. In yet another embodiment, the inducing composition is a chemical that is translocated within the plant cells. The inducing composition is also a ligand that is highly specific for the EcR LBD of the activation cassette. Binding of the inducing composition or ligand to the LBD of the activation cassette results in induction of the inducible promoter of the target cassette and expression of the nucleic acid sequence encoding the selected protein. Thus this system modulates ethylene sensitivity in the plant. The inducing composition also is characterized by low toxicity to the plant cells, tissues, and organs. The inducing composition also has the ability to be rapidly depleted from the plant to "turn off" the modulation of ethylene sensitivity, and allow efficient control of the modulation, as described in more detail below.

Among such effective inducing compositions are ligands that preferentially bind to the ecdysone ligand binding domain. In certain embodiments, these ligands include diaceylhydrazine compounds, including the commercially available tebufenozide (Dow AgroSciences), methoxyfenozide (Dow AgroSciences), halofenozide (Dow AgroSciences), and chromafenozide (Nippon Kayaku) (see International Patent Publication No. WO 96/027673 and U.S. Pat. No. 5,530,028). Other useful inducers are non-steroidal ligands including the dibenzoylhydrazine derivatives described in U.S. Pat. No. 6,258,603. Still other useful inducers are the 4-tetrahydroquinoline derivatives described in detail in US Patent Application Publication No. US 2005/0228016. A number of additional suitable compounds, such as 1-Aroyl-4-(arylamino)-1,2,3,4-tetrahydroquinoline (THQ), are listed in Kumar et al, J. Biol. Chem. 2004, 279 (26):27211-8; Hormann et al, J. Comput Aided Mol. Res 2003 17(2-4):135-53; Tice et al, Bioorg Med Chem Lett 2003, 13(11:1883-6; and Tice et al, 2003 Bioorg Med Chem Lett. 2003 13(3):475-8.

Thus, the gene expression system is induced or "turned on" by a chemical inducing composition or inducer which, when in contact with the ligand binding domain of the activation cassette, activates the response element of the minimal promoter and thus turns on expression of the nucleic acid sequence or gene that modulates ethylene sensitivity. This gene expression system provides the means for external controllable modulation of ethylene sensitivity of the plant cell containing the gene expression system.

II. THE TRANSGENIC PLANT, PLANT CELL, TISSUE OR ORGAN

As described above, the gene expression system is designed for integration into a plant, plant cell or other tissue or organ of a plant. Optionally, such integration may also be transient. However, in certain embodiments of this invention stable integration into the chromosomes of the plant is desired.

In one embodiment, a transgenic plant cell is designed that expresses a gene expression system as described above and in which ethylene sensitivity is temporally and reversibly controlled. Such a plant cell, in one embodiment, is a cell into which the activation cassette and target cassette of the gene expression system are transfected or transformed. In one embodiment, wherein the activation and target cassettes are on the same plasmid, this plasmid is transfected or transformed into plant cells. In another embodiment, where the activation and target cassettes are on separate plasmids, both plasmids are separately or together transfected or transformed into the same plant cell. Alternatively, each of the two separate plasmids is transfected or transformed into a different cell of the same plant. In still an alternative embodiment, each of the two plasmids is transformed separately into a different plant, and each plant carrying a single plasmid is sexually crossed to produce a hybrid containing both plasmids, thus providing a functional inducible system.

Transfection involves introducing the exogenous or heterologous RNA or DNA inside the cell, so as to effect a phenotypic change. Transformation refers to the transfer and integration of a nucleic acid fragment into the chromosomal DNA of the plant cell, resulting in genetically stable inheritance. Thus, plant cells containing the transformed nucleic acid fragments are referred to as "transgenic" or "recombinant" or "transformed" organisms. Thus, progeny of the initially transformed or transfected plant cells also have the cassettes transiently or stably integrated into their chromosomes.

1. Transformation

The transformation of the plant cell involves producing vectors or plasmids that comprise only the activation cassette, only the target cassette, or both cassettes. See, the examples of FIGS. 2-3. Suitable vector and plant combinations are readily apparent to those skilled in the art and can be found, for example, in Maliga et al, 1994 Methods in Plant Molecular Biology: A Laboratory Manual, Cold Spring Harbor, N.Y.

For example, a suitable "vector" is any means for the cloning of and/or transfer of a nucleic acid into a plant cell. A vector may be a replicon to which another DNA segment may be attached so as to bring about the replication of the attached segment. A "replicon" is any genetic element (e.g., plasmid, phage, cosmid, chromosome, virus) that functions as an autonomous unit of DNA replication, i.e., capable of replication under its own control. Vectors useful to transform plant cells with the gene expression system include both viral and nonviral means for introducing the nucleic acid into a cell. A large number of vectors known in the art may be used to manipulate nucleic acids, incorporate response elements and promoters into genes, etc. Possible vectors include, for example, plasmids or modified plant viruses including, for example bacteriophages such as lambda derivatives, or plasmids such as pBR322 or pUC plasmid derivatives, or the Bluescript vector. Conventional means of ligating the appropriate DNA fragments into a chosen vector that has complementary cohesive termini or enzymatically modifying a suitable insertion site by ligating nucleotide sequences (linkers) into the DNA termini are known. Any viral or non-viral vector that can be used to transform plant cells is useful for this purpose. Non-viral vectors include plasmids, liposomes, electrically charged lipids (cytofectins), DNA-protein complexes, and biopolymers. In addition to the cassettes of the gene expression system, a vector may also comprise one or more regulatory regions, and/or selectable markers useful in selecting, measuring, and monitoring nucleic acid transfer results (transfer to which tissues, duration of expression, etc.).

The term "plasmid" refers to an extra chromosomal element usually in the form of circular double-stranded DNA molecules. Such elements may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

Vectors or plasmids may be introduced into the desired plant cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267:963 967; Wu and Wu, 1988, J. Biol. Chem. 263:14621 14624; and Hartmut et al., U.S. Pat. No. 5,354,844). Alternatively, the use of cationic lipids may promote encapsulation of negatively charged nucleic acids, and also promote fusion with negatively charged cell membranes (Felgner and Ringold, 1989 Science 337:387 388). Particularly useful lipid compounds and compositions for transfer of nucleic acids are described in U.S. Pat. Nos. 6,172,048, 6,107,286, and 5,459,127. Other molecules are also useful for facilitating transfection of a nucleic acid, such as a cationic oligopeptide or cationic polymer (e.g., U.S. Pat. No. 5,856,435), or peptides derived from DNA binding proteins (e.g., U.S. Pat. No. 6,200,956). It is also possible to introduce a vector as a naked DNA plasmid (see U.S. Pat. Nos. 5,693,622, 5,589,466 and 5,580,859). Receptor-mediated DNA delivery approaches can also be used to effect transformation of the gene expression cassettes into the plant cell. Transformation of plants may be accomplished, e.g., using *Agrobacterium*-mediated leaf disc transformation methods of Horsch et al, 1988 Leaf Disc Transformation: Plant Molecular Biology Manual) or other methods known in the art.

2. Propagation and Screening

Thus, after transforming at least one cell in the plant with the gene expression system described above (in a single plasmid or as multiple transformed plasmids, each containing a different cassette), a method for producing a transgenic plant, plant tissue or plant organ further includes propagating a plant, or plant hybrid as described above, from the transformed plant cell or plant under conditions typical for the selected plant. The plants are then screened to select the plants (cells, tissues, organs) comprising or demonstrating the phenotypic traits of a transformed plant cell. For example, subsequent screening of the resulting plants or cells, tissues and organs thereof, is conducted to determine whether the plant contains the desired integrated nucleic acid sequences of the gene expression cassettes are also known to those of skill in the art. For example, cells which have stably integrated the introduced DNA into their chromosomes can be selected by the use of one or more reporter genes or markers in the plasmids. In the examples below, kanamycin, actinonin, bialaphos or luciferase are employed for this purpose.

A plant (tissue or organ) that has successfully integrated the expression system demonstrates rapid ethylene insensitivity when the plant is contacted with an inducing composition as described above. Any plant (including plant cell, tissue, or organ) is susceptible to such transformation and thus recombinant plants may be bred by conventional means. Plants that are particularly desirable for transformation with the gene expression system and thus susceptible to modulation of their ethylene sensitivities include dicotyledons, monocotyledons, decorative, flowering plants as well as plants for human or animal consumption. Without limitation, such plants include rice, maize, wheat, barley, sorghum, millet, grass, oats, tomato, potato, banana, kiwi fruit, avocado, melon, mango, cane, sugar beet, tobacco, papaya, peach, strawberry, raspberry, blackberry, blueberry, lettuce, cabbage, cauliflower, onion, broccoli, brussel sprout, cotton, canola, grape, soybean, oil seed rape, asparagus, beans, carrots, cucumbers, eggplant, melons, okra, parsnips, peanuts, peppers, pineapples, squash, sweet potatoes, rye, cantaloupes, peas, pumpkins, sunflowers, spinach, apples, cherries, cranberries, grapefruit, lemons, limes, nectarines, oranges, peaches, pears, tangelos, tangerines, lily, carnation, chrysanthemum, petunia, rose, geranium, violet, gladioli, orchid, lilac, crabapple, sweetgum, maple, poinsettia, locust, ash, linden tree and *Arabidopsis thaliana*.

Plant tissues and organs include, without limitation, vegetative tissues, e.g., roots, stems, or leaves, and reproductive tissues, such as fruits, ovules, embryos, endosperm, integument, seeds, seed coat, pollen, petal, sepal, pistils, flowers, anthers, or any embryonic tissue.

III. METHOD FOR CONTROLLING ETHYLENE SENSITIVITY

Such transgenic plants, cells, tissues, flowers, seeds or organs may be subject to a method for controlling ethylene sensitivity by using an effective amount of the inducing composition. The inducing composition may be contacted with, absorbed by, and/or translocated within, the cells of the transgenic plant, plant cells, plant tissues or plant organs. Application techniques include, without limitation, immersing, spraying, powdering, drenching, dripping, or irrigating the plant, or soil or media in contact with the plant, with the inducer.

In the presence of the inducing composition, the response of the plant cells to ethylene is modulated in a manner dependent upon the identity of the selected protein. In the examples below in which the selected protein is the dominant negative mutant etr1-1, the application of the inducer increases the expression of etr1-1 and decreases sensitivity of the plant to ethylene. This decrease in sensitivity lasts for the time during which the inducer is being applied to the plant (cell, tissue or organ), and for such time as the plant continues to metabolize the remaining inducer once active application is stopped. The response of the plant cells to ethylene is reversed, in this case, increased, after a selected time by depriving the plant of the inducer.

"Control", "modulation" or "regulation" of the expression of the protein that affects ethylene sensitivity or ethylene production in the plant cells may be accomplished in several ways. In one embodiment of the method, modulation of the protein expression (including the quantitative magnitude of that expression) is controlled by the timing of application of the inducing composition to the plant. In another embodiment, the concentration of the inducing composition applied to the plant is used to control protein expression (including the quantitative magnitude of that expression) and thus ethylene sensitivity. In still a further embodiment, the modulation of the protein expression (including the quantitative magnitude of that expression) is controlled by the duration of the application of the inducing composition to the plant. Any one, two or all three of these parameters of application of the inducing composition may be varied during growth of the plant to obtain the desired result.

As one example of control through timing, the inducing composition may be applied at a selected time in the plant's growth cycle to induce ethylene sensitivity, e.g., before or after one of the germination, fruit ripening, or flowering of the plant or in response to an environmental condition (e.g., before or after the plant is exposed to a stress factor, such as a pathogen or drought). In another embodiment, the inducing composition is applied at multiple times in the growth cycle of the plant. In still other embodiments, the application of the inducing composition is ceased at selected times in order to control ethylene sensitivity. The desired timing of application may be selected and varied depending upon the type of plant being treated, the potency of the inducing composition, and its possible cytotoxic effects on the plant.

As one example of control through inducing composition concentration, the inducing composition is applied to the plant in a concentration of 0.01-20 µM. In another embodiment, the concentration is 10 µM. In another embodiment, the concentration is at least 0.01, 0.10, 0.20, 0.30, 0.40, 0.5, 0.6, 0.7, 0.8, 0.9, 1.0, 2.0, 3.0, 4.0, 5.0, 6.0, 7.0, 8.0, 9.0, 10.0, 11.0, 12.0, 13.0, 14.0, 15.0, 16.0, 17.0, 18.0, 19.0, and at least 20.0 µM, and including fractional concentrations therebetween. In yet another embodiment, the concentration is 20 µM. In still other embodiments, a concentration of greater than 20 µM of inducing composition is used. In still another embodiment, a concentration of greater than 30 µM is used. In another embodiment, a concentration of greater than 40 µM is used. In yet another embodiment, concentrations greater than 50 µM are useful in the methods described herein. For example, see Example 9 below, which demonstrates how the concentration of the inducer modulates the degree of ethylene sensitivity shown by the plant. In a manner similar to the control by timing of application, the concentration of the inducing composition may be used to respond to the changing requirements of the plant at different growth stages or in response to changing environmental conditions.

The third method of controlling modulation of the protein mediating ethylene sensitivity or ethylene production in the plant involves varying the duration of application of the inducing composition. For example, the duration of application of the inducing composition to the plant may range from an application time of at least 10 minutes, at least 30 minutes, from at least 1 to about 24 hours, or more, depending upon the effect desired, the potency of the inducer and the likelihood of undesirable cytotoxic effects. If desired, the application of the inducing composition may be given over a period of several days. The duration of application can generally be selected by an experienced grower.

In general, the time between ceasing application of inducer to reversal of the plants' response to the inducer is about 2 or more days depending upon the size of the plant, the method of application, and the amount of inducer applied. Alternatively, where the nucleic acid sequence under the control of the inducible promoter of the target cassette is a complementary sequence to a wildtype gene, or an antisense version thereof, the application of a suitable inducer can increase the sensitivity of the plant to ethylene. For example, increasing the expression of ethylene receptors (ETR1, ETR2, ERS1, ERS2 or EIN4) leads to more ethylene receptors and decreased sensitivity to ethylene. Over-expression of truncated ETR1 fused to the N-terminal kinase domain of CTR1 gives slight ethylene insensitivity in wildtype *Arabidopsis*. Increasing the expression of EBF1, EBF2, and/or decreasing the expression of EIN3, in a plant makes the plant less sensitive to ethylene. Decreasing the expression of ACO, ACS, EIN2, EDF or EEN and EIN6 leads to decreased ethylene production and/or decreased ethylene response. Increasing expression of ACD leads to decreased ethylene and decreased ethylene response. The response of the plant cells to ethylene is reversed, in this case, increased, after a selected time by depriving the plant of the inducer. This allows the plants to continue to develop, mature and ripen normally once the induction is removed.

Application of the inducer to a plant stably transformed with the gene expression system described herein permits control of one or more characteristics of plant growth sensitive to ethylene, such as, for example, senescence, fruit ripening, germination, pathogen resistance, leaf abscission, flower abscission, bud abscission, boll abscission, fruit abscission and flowering, as well as the plant's response to stress, such as caused by conditions of drought, heat, population density and salinity, among others.

The methods described herein also can be employed more specifically as methods for increasing a plant's resistance and/or tolerance to disease by increasing the ethylene insensitivity of the plant. Alternatively, the method can be applied to delay ripening or flowering of a plant, tissue or organ, e.g., for purposes of storage or transportation, by increasing the ethylene insensitivity of the plant. In still another embodiment, the method of using the transformed plants described herein with the suitably timed application of the inducer composition enables the treatment of plants undergoing undesirable growing conditions, such as drought or excessive heat, by applying the inducing composition to decrease sensitivity to ethylene and allow the plant to more readily tolerate the environmental conditions. One of skill in the art of plant propagation and growth can readily select instances in which the transformed plants and the method of induction of expression of the nucleic acid sequences described above will provide benefits based on the teachings of this specification.

Therefore, timing, duration or concentration of application of the inducer may be altered during growth of the plant using the methods described herein to control the ethylene sensitivity and thus the growth characteristics of the plant with considerable precision.

IV. THE EXAMPLES

The following examples demonstrate use of an above-described gene expression system, which comprises an activation cassette comprising, under control of a constitutive G10-90 promoter and in operative association therewith, (a) a GAL 4 DBD that recognizes a response element comprising five copies of GAL4 response element; (b) a mutant ecdysone receptor LBD comprising domains D, E and F with a Thr to Val mutation at amino acid 335 in the full-length CfEcR.; and (c) a VP16 AD which is activated in the presence of an inducing composition. The target cassette comprises an inducible promoter comprising, in operative association, the five copies of the GAL 4 response element located upstream of the minimal 35S promoter responsive to activation of the VP16 AD, the inducible promoter controlling expression of (e) a nucleic acid sequence that encodes a mutant ETR1 protein. According to this embodiment, components of the activation cassette and the targeting cassette, when in the plant cell, modulate expression of the mutant ETR1 protein and selectively decrease ethylene sensitivity in the plant cell. This protein expression is controlled by interaction with the inducing composition, which modulates expression of the selected protein and selectively modulates ethylene sensitivity in the plant cell. The modulation in protein expression is controlled by the timing, the concentration, and the duration of the application of the inducing composition.

More specifically, the exemplified gene expression system contains an activation cassette and target cassette present on a single plasmid, p185. This plasmid is schematically illustrated in FIG. 2. Still another exemplary plasmid is illustrated in FIG. 3. The nucleic acid sequences of the gene expression cassette components of each plasmid of FIGS. 2-3 are further identified as SEQ ID NOs: 1-2. The nucleotide sequences of gene expression cassette components of other plasmids discussed in the examples are disclosed in SEQ ID NO: 3.

The following examples illustrate certain embodiments of the above-discussed compositions and methods. These examples do not limit the disclosure of the claims and specification.

Example 1

Plasmids

The gene cassette components include for the activation cassette: the G10-90 constitutive promoter (nucleotide 1 to 243 of SEQ ID NO: 1), the VP16 activation domain (nucleotide 249 to 529 of SEQ ID NO: 1), the GAL4 DNA binding domain (nucleotide 534 to 983 of SEQ ID NO: 1), and the T52V mutant ecdysone receptor ligand binding domain (nucleotide 990 to 1997 of SEQ ID NO: 1) associated with the NOS terminator sequence (nucleotide 2070 to 2364 of SEQ ID NO: 1) were individually cloned. Similarly, the target cassette components, including the inducible promoter which consists of five copies of the GAL4 response element (nucleotide 2391 to 2492 of SEQ ID NO: 1) and the minimal 35S promoter (nucleotide 2499 to 2554 of SEQ ID NO: 1), and the mutant etr1-1 gene (nucleotide 2557 to 4764 of SEQ ID NO: 1) and the 35S terminator sequence (4791 to 5001 of SEQ ID NO: 1) were individually cloned. SEQ ID NO: 1 is shown in FIG. 4.

These components were assembled in expression cassettes individually in SK⁻ plasmid (Stratagene) and then combined into various plasmids:

Cassette (1): G10-90 promoter→VP16:GAL4:EcRDEF T52V—NOS terminator

Cassette (2): G10-90 promoter→GAL4:VP16:EcRDEF T52V—NOS terminator

Cassette (3): G10-90 promoter→etr1-1—35S terminator

Cassette (4): G10-90 promoter→PDF1—E9 terminator

Cassette (5): G10-90 promoter→Luciferase—35S terminator

Cassette (6): 5×G-M35S inducible promoter→etr1-1—35S terminator

Cassette (7): 5×G-M35S inducible promoter→Luciferase—35S terminator

In assembling the activation cassettes, the following components were fused in two different orders to make two different activation cassettes:

VP16 AD to GAL4 LBD to EcR(DEF) of T52V DBD (abbreviated "VGE") and

GAL4 LBD to VP16 AD to EcR(DEF) of T52V DBD (abbreviated GVE).

Inducible luciferase controls were also supplied as positive controls.

Thereafter, plasmid DNAs were made in pBlueScript II SK⁻ backbone (Stratagene). The SK⁻ multiple cloning sites region was replaced with a new multiple cloning sites containing the recognition sites for 8 bp cutting enzymes. Some of these enzymatic cleavage sites were identified in FIGS. 2-3 of exemplary plasmids.

Six exemplary *E. coli* plasmids were prepared and sequenced to confirm the nucleotide sequence. Such plasmids contain unique enzymatic cleavage sites for addition/deletion/exchange of each component as illustrated in the FIGS. 2-3. Thus, each entire construct can be transferred to any other vector of choice including a binary vector for plant transformation.

The constructs made in SK⁻ minus plasmids were later transferred to binary plasmid pBIN19 (American Type Culture Collection Accession No. 37327). Since pBIN19 already has neomycin plant selectable marker gene, LB, RB and nptII selectable markers, the figures and/or sequence listing does not indicate backbone sequences, but only shows the gene expression sequences of interest, i.e., the primary components of the gene expression system, e.g., the Ec receptor and inducible etr1-1 or luciferase were cloned between the left and right borders.

The following five *Agrobacterium* binary plasmids were selected for use in the production of transgenic plants in Example 2 and in a protoplast experiment of Example 3:

p184 [G10-90p-VGE-NosT-5×GAL-M35S-LUC] was used obtain transgenic plants containing the G10-90 promoter-driven VGE receptor and inducible luciferase. The expression cassette components of p184 are illustrated in SEQ ID NO: 3, namely the G10-90 constitutive promoter (nucleotide 1 to 243 of SEQ ID NO: 3), the VP16 activation domain (nucleotide 249 to 529 of SEQ ID NO: 3), the GAL4 DNA binding domain (nucleotide 534 to 983 of SEQ ID NO: 3), and the T52V mutant ecdysone receptor ligand binding domain (nucleotide 990 to 1997 of SEQ ID NO: 1) associated with the NOS terminator sequence (nucleotide 2070 to 2364 of SEQ ID NO: 3), the inducible promoter which consists of five copies of the GAL4 response element (nucleotide 2391 to 2492 of SEQ ID NO: 3) and the minimal 35S promoter (nucleotide 2499 to 2554 of SEQ ID NO: 3), the luciferase marker gene (nucleotide 2557 to 4209 of SEQ ID NO: 3) and the 35S terminator sequence (4217 to 4427 of SEQ ID NO: 3).

p185 [G10-90p-VGE-NosT-5×GAL-M35S-etr1] was the exemplary plasmid containing both the activation cassette fused to the target cassette, for producing transgenic plants containing the G10-90 promoter-driven VGE receptor and inducible etr1-1. See, e.g., FIG. 2 and SEQ ID NO: 1, as well as the components described above.

p186 [G10-90p-GVE-NosT-5×GAL-M35S-LUC] was a plasmid used to obtain transgenic plants containing the G10-90 promoter-driven GVE receptor and inducible luciferase. The expression cassette components of p186 are illustrated in SEQ ID NO: 4, namely the G10-90 constitutive promoter (nucleotide 1 to 243 of SEQ ID NO: 4), the GAL4 DNA binding domain (nucleotide 276 to 716 of SEQ ID NO: 4), the VP16 activation domain (nucleotide 717-793 of SEQ ID NO: 4), and the T52V mutant ecdysone receptor ligand binding domain (nucleotide 994 to 1991 of SEQ ID NO: 4) associated with the NOS terminator sequence (nucleotide 2064 to 2258 of SEQ ID NO: 4), the inducible promoter which consists of five copies of the GAL4 response element (nucleotide 2385 to 2486 of SEQ ID NO: 4) and the minimal 35S promoter (nucleotide 2493 to 2548 of SEQ ID NO: 4), the luciferase marker gene (nucleotide 2551 to 4203 of SEQ ID NO: 4) and the 35S terminator sequence (4211 to 4421 of SEQ ID NO: 4).

p187 [G10-90p-GVE-NosT-5×GAL-M35S-etr1] was a plasmid used to obtain transgenic plants containing the G10-90 promoter-driven GVE receptor and inducible etr1-1. See FIG. 3 and SEQ ID NO: 2. The expression cassette components of p 187 are the G10-90 constitutive promoter (nucleotide 1 to 243 of SEQ ID NO: 2), the GAL4 DNA binding domain (nucleotide 276 to 716 of SEQ ID NO: 2), the VP16 activation domain (nucleotide 717-793 of SEQ ID NO: 2), and the T52V mutant ecdysone receptor ligand binding domain (nucleotide 994 to 1991 of SEQ ID NO: 2) associated with the NOS terminator sequence (nucleotide 2064 to 2258 of SEQ ID NO: 2), the inducible promoter which consists of five copies of the GAL4 response element (nucleotide 2385 to 2486 of SEQ ID NO: 2) and the minimal 35S promoter (nucleotide 2493 to 2548 of SEQ ID NO: 2), the etr1 gene (nucleotide 2551 to 4761 of SEQ ID NO: 2) and the 35S terminator sequence (4785 to 4995 of SEQ ID NO: 2).

p1002 [G10-90p-VGE-NosT-5×GAL-M35S-etr1 and MMVp-def-rbcS-E9t] and its components are illustrated in SEQ ID NO: 5, namely the G10-90 constitutive promoter (nucleotide 1 to 243 of SEQ ID NO: 5), the VP16 activation domain (nucleotide 249 to 529 of SEQ ID NO: 5), the GAL4 DNA binding domain (nucleotide 534 to 983 of SEQ ID NO: 5), and the T52V mutant ecdysone receptor ligand binding domain (nucleotide 990 to 1997 of SEQ ID NO: 5) associated with the NOS terminator sequence (nucleotide 2070 to 2364 of SEQ ID NO: 5), the inducible promoter which consists of five copies of the GAL4 response element (nucleotide 2391 to 2492 of SEQ ID NO: 5) and the minimal 35S promoter (nucleotide 2499 to 2554 of SEQ ID NO: 5), the etr1 gene (nucleotide 2557 to 4764 of SEQ ID NO: 5), the 35S terminator sequence (4791 to 5001 of SEQ ID NO: 5), the MMV promoter (nucleotide 7228 to 6592 of SEQ ID NO: 5), the P-DEF marker gene (nucleotide 6533-5712 of SEQ ID NO: 5) and the rbcS-E9 terminator (nucleotide 5682 to 5038 of SEQ ID NO: 5).

p1003 [G10-90p-GVE-NosT-5×GAL-M35S-etr1 and MMVp-def-rbcS-E9t] and its components are illustrated in SEQ ID NO: 6, namely the G10-90 constitutive promoter (nucleotide 1 to 243 of SEQ ID NO: 6), the GAL4 DNA binding domain (nucleotide 276 to 716 of SEQ ID NO: 6), the VP16 activation domain (nucleotide 717 to 973 of SEQ ID NO: 6), and the T52V mutant ecdysone receptor ligand binding domain (nucleotide 984 to 1991 of SEQ ID NO: 6) associated with the NOS terminator sequence (nucleotide 2064 to 2258 of SEQ ID NO: 6), the inducible promoter which consists of five copies of the GAL4 response element (nucleotide 2385-2486 of SEQ ID NO: 6) and the minimal 35S promoter (nucleotide 2493 to 2548 of SEQ ID NO: 6), the etr1 gene (nucleotide 2551 to 4761 of SEQ ID NO: 6), the 35S terminator sequence (4785 to 4995 of SEQ ID NO: 6), the MMV promoter (nucleotide 7222 to 6586 of SEQ ID NO: 6), the P-DEF marker gene (nucleotide 6527 to 5706 of SEQ ID NO: 6) and the rbcS-E9 terminator (nucleotide 5676 to 5032 of SEQ ID NO: 6).

Example 2

Production of Transgenic Tobacco Plants

Tobacco plants were transformed with the plasmids of Example 1 and were produced by standard *Agrobacterium*-mediated leaf disc transformation as described in Fisher and Guiltinan 1995 Plant Molecular Biology Reporter 13: 278-289. Plants were propagated on rooting medium containing kanamycin and then the introduction and inheritance of the gene expression system was confirmed by PCR as described below.

Single leaf from each plant maintained in a magenta box was collected by snap freezing in liquid nitrogen and stored frozen at −80° C. Leaf (50-100 mg) was then transferred to KONTES tube and ground with the KONTES disposable pestle using a drill for about 1 minute and then for a few second after adding lysis buffer. DNA was purified using the DNEASY mini kit (Qiagen). DNA was finally eluted in 100 µl.

Specific PCR primers were designed to amplify the 529 bp of VGE, the 495 bp of GVE, the 463 bp of the marker gene luciferase LUC, or the 441 bp of the mutant etr-1 gene. Transgenes were amplified for 35 cycles in 50 µl reaction using 3 µl plant DNA, 10 pmoles of each primer and 25 µl AMPLITAQ GOLD PCR (ABI). Twenty five µl PCR reaction was run on a 1% agarose gel and positive plants were identified by the amplification of two different transgenes.

Extreme care was taken to prevent false positives due to contamination and non-specific amplification. High stringent primers that do not bind to tobacco genome were synthesized. Leaf material was handled with extreme caution during the grinding and DNA preparation to minimize cross contamination. Non transgenic control plant DNA was isolated along with each batch of DNA preparations. No DNA PCR control was included with each PCR amplification. Other precautions such as aerosol resistant pipette tips and disposable bench surface diapers were used, and gloves changed frequently.

Hot start PCR was used to minimize non-specific binding of primers. Cross contamination was also checked in some DNAs by PCR amplifying with primers that are not expected to give a band.

The results of the PCR were as follows:

For p184 (VP16 AD to GAL4 LBD to EcR(DEF) of T52V DBD plus inducible luciferase; abbreviated "VGE"): 10 plants were screened and 8 plants were positive for VGE and LUC (p184-2, 3, 4, 5, 7, 8, 9, and 10). Two plants were negative for VGE or LUC (p184-1 and 6).

For the exemplary plasmid containing the activation and target cassettes for expression of the mutant etr1-1 gene, p185, 16 plants were screened and 13 plants were positive for VGE and etr-1 (plasmids designated as p185-1, 2, 3, 4, 5, 8, 10, 11, 12, 13, 14, 15, and 16). Two plants were negative for VGE and etr-1 (p185-6, 7 and 9).

For p186 (GAL4 LBD to VP16 AD to EcR(DEF) of T52V; abbreviated "GVE"+inducible LUC), 25 plants were screened and 23 plants were positive for GVE and LUC (p186-2, 3, 4, 5, 6, 7, 8, 9, 10, 11, 12, 13, 15, 16, 17, 18, 19, 20, 21, 22, 23, 24, and 25) and 2 plants were negative for GVE or LUC (p186-1 and 14).

For p187 (GVE+inducible etr-1): 34 plants were screened and 33 plants were positive for GVE and etr-1 (p187-1, 2, 3, 4, 5, 6, 7, 8, 9, 10, 11, 12, 13, 15, 16, 17, 18, 19, 20, 21, 22, 23, 24, 25, 26, 27, 28, 29, 30, 31, 32, 33, and 34) and 1 plant was negative for GVE and etr-1 (p187-14).

Example 3

Effect of Modulation of Ethylene Sensitivity on Tobacco Plant Growth

A triple response assay as described in Guzman and Ecker 1990 The Plant Cell, 2:513-523, modified as provided herein, was conducted to determine the effect of the modulation of ethylene sensitivity in the transformed tobacco plants of Example 2. From each transformed plant designated 185-1, 184-3, 185-8, 185-11, 187-7, 187-13, 187-17 and 187-21, two leaves from each plant were cut into small pieces. These pieces were plated onto MSS plates containing 100 ng/L kanamycin, with or without 10 µM inducer, i.e., 3,5 Dimethyl-benzoic acid N-(1-ethyl-2,2-dimethyl-propyl)-N'-(3S-hydroxymethyl-5-methyl-2,3-dihydro-benzo[1,4]dioxine-6-carbonyl)hydrazide. MSS plates without antibiotic or inducer were used as controls.

These plated plant tissues were grown at 25° C. with light in growth chambers to induce shoots. Shoots were transferred into fresh plates for about two weeks for continued growth at 25° C. Each callus was then transferred to new culture dishes with or without inducer. Each callus with shoots starting to initiate was split into several plates with approximately equal amounts of callus per plate.

The plates were then separated into groups for the following treatment protocols which lasted for 18 days

| | | |
|---|---|---|
| (a) | induced, dark, no ethylene (air control) | |
| (b) | no inducer, dark, no ethylene (air control) | |
| (c) | induced dark, ethylene at concentration of about 10 ppm | |
| (d) | no inducer, dark, ethylene (conc about 10 ppm) | |

Shoot length was measured, and the relative assessment of the efficacy of the transgenic plants prepared according to the Examples based on raw data for shoot length is reported in Table I for conditions (a) through (d) above. Typically, wildtype shoots exposed to ethylene in the dark display stunted growth. Ethylene insensitive plants under these conditions should show elongated growth. The transgenic plants containing the activation and target cassettes for expression of etr1-1 in the presence of inducer for expression of mutant etr1-1 demonstrated ethylene insensitivity, based on increased shoot length compared to non-induced transgenic plants under the same circumstances. Shoots grown in the light produced uninterpretable data.

TABLE I

Induction of Ethylene Insensitivity in Tobacco
Conditions: Ethylene/Dark (a)-(d)

| Plasmids | Treatment | Shoot Length (cm) | | | | | Avg (cm) |
|---|---|---|---|---|---|---|---|
| 185-1 | air control | 2.4 | 2.3 | 2.5 | 2.4 | 2.5 | 2.4 |
| (VGE) | uninduced | 1.5 | 1.8 | 2.0 | 3.0 | 2.0 | 2.1 |
|  | induced | 5.0 | 1.8 | 2.8 | 2.0 | 2.2 | 2.8 |
| 185-3 | air control | 7.0 | 5.4 | 6.0 | 5.0 | 4.5 | 5.6 |
| (VGE) | uninduced | 4.0 | 2.5 | 3.5 | 4.5 | 4.5 | 3.8 |
|  | induced | 8.0 | 6.0 | 5.5 | 4.5 | 3.8 | 5.6 |
| 185-8 | air control | 5.0 | 5.0 | 5.0 | 4.2 | 4.0 | 4.6 |
| (VGE) | uninduced | 2.5 | 3.0 | 2.0 | 2.3 | 3.0 | 2.6 |
|  | induced | 5.5 | 5.0 | 4.0 | 4.4 | 4.3 | 4.6 |
| 185-11 | air control | 4.8 | 5.0 | 4.5 | 4.0 | 4.5 | 4.6 |
| (VGE) | uninduced | 4.0 | 3.7 | 3.0 | 2.5 | 2.0 | 3.0 |
|  | induced | 4.0 | 4.5 | 4.0 | 4.5 | 3.0 | 4.0 |
| 187-7 | air control | 4.0 | 3.0 | 3.4 | 3.8 | 3.0 | 3.4 |
| (GVE) | uninduced | 4.0 | 3.0 | 4.0 | 2.5 | 4.0 | 3.5 |
|  | induced | 3.0 | 3.0 | 3.0 | 3.0 | 3.0 | 3.0 |
| 187-13 | air control | 4.5 | 4.4 | 3.5 | 4.0 | 3.5 | 4.0 |
| (GVE) | uninduced | 4.0 | 3.0 | 3.0 | 3.0 | 2.0 | 3.0 |
|  | induced | 4.0 | 3.5 | 5.0 | 4.0 | 3.0 | 3.9 |
| 187-17 | air control | 6.0 | 5.5 | 5.0 | 4.0 | 3.5 | 4.8 |
| (GVE) | uninduced | 3.0 | 3.0 | 2.5 | 2.0 | 1.5 | 2.4 |
|  | induced | 5.6 | 5.6 | 3.5 | 3.5 | 3.5 | 4.3 |
| 187-21 | air control | 4.0 | 3.5 | 5.0 | 4.5 | 4.0 | 4.2 |
| (GVE) | uninduced | 3.5 | 3.5 | 2.8 | 2.8 | 2.5 | 3.0 |
|  | induced | 4.0 | 4.0 | 3.5 | 3.0 | 2.5 | 3.4 |

The results of this example demonstrate that the gene expression system and plants transformed therewith when treated with the selected inducing compositions to which the gene expression systems respond permit successful modulation of ethylene sensitivity.

Example 4

Production of Transgenic *Arabidopsis* Plants

*Arabidopsis* plants were transformed with plasmids from Example 1 with *Agrobacterium* using the standard floral dip protocol. Seed was harvested and plated onto kanamycin containing media. Transformed plants were selected for ability to grow on kanamycin and screened by PCR to confirm presence of the etr1-1 gene. Luciferase assays were used for transformants that carry the luciferase construct. Positive transformants were selfed to produce T1 seed. Seed was grown on kanamycin containing media to identify lines homozygous for the transgenes. Homozygous plants were used to test for induction of ethylene insensitivity.

Example 5

Effect of Modulation of Ethylene Sensitivity on *Arabidopsis* Plant Growth

A triple response assay (Guzman and Ecker, 1990 cited above, modified as described below) was used to determine the modulation of ethylene sensitivity in the transformed *Arabidopsis* plants of Example 4. *Arabidopsis* seed was surface-sterilized and imbibed in 20 µM inducer in the dark for 4 days at 4° C. The seed was plated on 0.5× MS with 1% sucrose and 20 µM inducer and for mutant receptors treated with 10 ppm ethylene or 1 ppm ethylene for wild-type receptors and grown in the dark for 4-8 days at 21° C. The response to ethylene was scored on the last day. The transgenic plants containing the activation and target cassettes for expression of etr1-1 in the presence of inducer for expression of mutant etr 1-1 demonstrated ethylene insensitivity, based on increased shoot length and/or altered root growth compared to non-induced transgenic plants under the same circumstances. The results of this example further demonstrate that the gene expression system and plants transformed therewith, when treated with the selected inducing compositions to which the gene expression systems respond, permit successful modulation of ethylene sensitivity.

Wild-type, ein2-5 (an ethylene insensitive mutant control), and p1002 *Arabidopsis* transformant seedlings were assayed for ethylene insensitivity using the triple response assay (Guzman and Ecker, 1990, cited above, with the following modifications) in which seeds were germinated on 0.5× MS media for 11 days in the dark in the presence of 10 ppm ethylene. Root and hypocotyl growth is inhibited by ethylene in ethylene sensitive but not in ethylene insensitive seedlings.

TABLE II

Induction of Ethylene Insensitivity in *Arabidopsis*

| | No inducer | | | 20 µM inducer | | | 20 µM inducer + 5 µM AgNO3 | | |
|---|---|---|---|---|---|---|---|---|---|
| | Avg | SD | t-test | Avg | SD | t-test | Avg | SD | t-test |
| Roots (mm) | | | | | | | | | |
| WT | 3.68 | 1.57 | — | 3.92 | 1.08 | — | 13.9 | 1.04 | — |
| Ein2-5 | 19.1 | 3.05 | p < 0.001 | 19.9 | 2.89 | p < 0.001 | 12.4 | 1.74 | p < 0.005 |
| p1002-1-4 | 3.12 | 0.95 | p = 0.126 | 5.8 | 1.8 | p < 0.001 | 11.8 | 1.41 | p < 0.001 |
| p1002-3-4 | 4.84 | 1.46 | p < 0.01 | 6.7 | 2.08 | p < 0.001 | 17.4 | 5.96 | p < 0.01 |
| p1002-11-3 | 3.67 | 0.88 | p = 0.970 | 5.6 | 1.35 | p < 0.001 | 11.7 | 1.45 | p < 0.001 |
| p1002-24-4 | 3.2 | 1.26 | p = 0.239 | 4.96 | 1.85 | p < 0.05 | 13.1 | 1.44 | p < 0.05 |
| p1002-23-2 | 3.89 | 1.28 | p = 0.601 | 6.04 | 2.28 | p = 0.001 | 10.5 | 2.78 | p < 0.001 |
| Hypocotyls (mm) | | | | | | | | | |
| WT | 11.8 | 1.37 | — | 12 | 1.08 | — | — | — | — |
| Ein2-5 | ~30 | — | — | ~30 | — | — | — | — | — |

TABLE II-continued

Induction of Ethylene Insensitivity in *Arabidopsis*

|  | No inducer | | | 20 μM inducer | | | 20 μM inducer + 5 μM AgNO3 | | |
| --- | --- | --- | --- | --- | --- | --- | --- | --- | --- |
|  | Avg | SD | t-test | Avg | SD | t-test | Avg | SD | t-test |
| p1002-1-4 | 12.4 | 1.61 | p = 0.217 | 12.3 | 1.01 | p = 0.270 | — | — | — |
| p1002-3-4 | 12.5 | 1.63 | p = 0.139 | 12.7 | 2.18 | p = 0.199 | — | — | — |
| p1002-11-3 | 11.9 | 1.27 | p = 0.915 | 12.1 | 0.85 | p = 0.656 | — | — | — |
| p1002-24-4 | 10.6 | 1.5 | P < 0.01 | 12.2 | 1.12 | p = 0.639 | — | — | — |
| p1002-23-2 | 12.4 | 1.69 | p = 0.174 | 12.1 | 0.73 | p = 0.772 | — | — | — |

All treated with 10 ppm ethylene for 11 days at RT in dark on 0.5 × MS + 1% sucrose As shown above, in the absence of the inducer, root and hypocotyl growth in the p1002 transformant seedlings was not significantly different from wild-type seedlings. However, in the presence of inducer, roots were significantly longer in the p1002 transformants relative to the wild-type seedlings, although they were not as long as the ein2 mutant. No effect was observed in the hypocotyls. In the presence of silver which also results in ethylene insensitivity and the inducer, as expected, roots of most of the p1002 *Arabidopsis* transformant seedlings were not significantly longer than either wild-type or ein2 mutant seedlings. Thus, the transgenic plants containing the activation and target cassettes for expression of etr1-1 in the presence of inducer for expression of mutant etr 1-1 demonstrate ethylene insensitivity, based on increased root length compared to non-induced transgenic plants under the same circumstances.

Example 6

Production of Transgenic Tomato Plants and Effect of Modulation of Ethylene Sensitivity on Plant Growth Tomato cotyledon pieces were transformed using the plasmids from Example 1 by *Agrobacterium* using standard methods. Putative transformants were selected using either kanamycin or actinonin and confirmed by PCR analysis. Positive transformants were selfed twice to obtain lines homozygous for the transgenes. Homozygous plants were used to test for induction of ethylene sensitivity in a manner similar to that of Example 5.

A triple response assay (Guzman and Ecker, 1990, cited above, modified as described below) was used to determine the modulation of ethylene sensitivity in the transformed tomato plants. Tomato seed was surface-sterilized and imbibed in 20 μM inducer in the dark for 4 days at 4° C. The seed was plated on 0.5× MS with 1% sucrose and 20 μM inducer and for mutant receptors treated with 10 ppm ethylene or 1 ppm ethylene for wild-type receptors and grown in the dark for 4-8 days at 21° C. The response to ethylene was scored on the last day. The transgenic plants containing the activation and target cassettes for expression of etr1-1 in the presence of inducer for expression of mutant etr 1-1 demonstrated ethylene insensitivity, based on increased shoot length and/or altered root growth, compared to non-induced transgenic plants under the same circumstances. The results of this example further demonstrate that the gene expression system and plants transformed therewith when treated with the selected inducing compositions to which the gene expression systems respond permit successful modulation of ethylene sensitivity.

Seed from three homozygous independent p1002 and p1003 lines were germinated in the dark on 0.5× MS medium+1% sucrose containing 20 μM ACC, the precursor to ethylene. Germination on ACC inhibits tomato seedling growth. Seed from the same lines also was germinated in the presence of 20 μM ACC plus 20 μM inducer. Results are shown in Table III.

TABLE III

Induction of Ethylene Insensitivity in Tomato

|  | No inducer | | | | 20 μM inducer | | | |
| --- | --- | --- | --- | --- | --- | --- | --- | --- |
|  | Hypocotyls (mm) | t-test | Root (mm) | t-test | Hypocotyls (mm) | t-test | Root (mm) | t-test |
| WT | 9.83 ± 2.60 |  | 21.9 ± 23.4 |  | 11.2 ± 3.18 |  | 11.2 ± 3.18 |  |
| p1002-4 | 8.12 ± 2.34 | P < 0.05 | 13.9 ± 18.2 | P = 0.268 | 32.7 ± 16.8 | P < 0.001 | 42.2 ± 16.3 | P < 0.001 |
| p1002-9 | 9.38 ± 2.63 | P = 0.613 | 16.5 ± 19.0 | P = 0.464 | 29.9 ± 7.85 | P < 0.001 | 35.0 ± 16.0 | P < 0.001 |
| p1002-18 | 9.33 ± 3.28 | P = 0.669 | 9.33 ± 17.5 | P = 0.168 | 35.4 ± 8.82 | P < 0.001 | 35.4 ± 8.82 | P < 0.001 |
| p1002-7 | 13.6 ± 3.29 | P < 0.001 | 25.4 ± 19.4 | P = 0.624 | 36.2 ± 8.42 | P < 0.001 | 44.5 ± 7.71 | P < 0.001 |
| p1002-16 | 11.1 ± 2.95 | P = 0.188 | 20.1 ± 18.7 | P = 0.816 | 39.6 ± 9.62 | P < 0.001 | 19.5 ± 16.3 | P = 0.154 |
| p1002-4 | 15.5 ± 3.79 | P < 0.001 | 26.2 ± 25.0 | P = 0.592 | 33.9 ± 6.02 | P < 0.001 | 29.8 ± 21.4 | P = 0.005 |

Measurements were taken from 14 day old seedlings grown in the presence of 20 μM ACC Growth on ACC in the presence of inducer resulted in a state of ethylene insensitivity as the induced seedlings exhibit elongated hypocotyls with no apical hook. In the absence of inducer, no ethylene insensitivity was obtained for the p1002 containing lines and only a little ethylene insensitivity was conferred by the p1003 construct. The results further demonstrate that induction is required to induce a full state of ethylene insensitivity.

Example 7

Production of Transgenic Corn Plants and Effect of Modulation of Ethylene Sensitivity on Corn Plant Growth Corn plants were transformed using the plasmids for Example 1 by microparticle bombardment. Putative transformants were selected using either actinonin or bialaphos and confirmed by PCR analysis. Positive transformants were backcrossed to inbred B73 to increase vigor. Transgenic corn plants produced as described above were tested for modulation of ethylene sensitivity. Modulation of ethylene sensitivity was determined at the molecular level by exposing plants to ethylene and measuring the change in induction of ethylene-induced genes. The transgenic plants containing the activation and target cassettes for expression of etr1-1 in the presence of inducing compound for expression of mutant etr 1-1 demonstrated ethylene insensitivity, based on decreased expression of ethylene inducible genes.

Transgenic corn plants produced as described above were tested for modulation of ethylene sensitivity. Modulation of ethylene sensitivity was determined at the molecular level by exposing plants to ACC, the precursor of ethylene and measuring the change in induction of ethylene-induced genes. Stalk sheath tissue was excised from transgenic T0 corn plants growing in a green house and used in an in vitro bioassay. Excised tissue was treated with either water or 20 μM inducer for 2 days to induce expression of the ethylene insensitive etr1-1 transgene. Following the 2 day induction period, the tissue was treated for one day with 0, 1 or 10 μM ACC to produce ethylene and then harvested. Harvested tissue was immediately placed in RNAlater (Ambion). Total RNA was prepared from the tissue using MagMAX-96 Total RNA Isolation Kit (Ambion). Induction of an ethylene inducible gene (ACC oxidase) was measured using quantitative PCR on an Applied Biosystems 7900 HT Fast Real-Time PCR system (ABI). TaqMan Assay Kit (ABI) was used for reverse transcriptase (RT) and PCR using manufacturer recommended protocols. Corn 18s was used as an internal control to normalize expression for each sample.

Sequences for the primers and probes were as follows:

```
18s
Forward Primer   CGTCCCTGCCCTTTGTACAC   SEQ ID NO: 11
Reverse Primer   ACACTTCACCGGACCATTCAA  SEQ ID NO: 12
Probe            CCGCCCGTCGCTCCTACCG    SEQ ID NO: 13
ACC Oxidase(aco):
Forward Primer   GTTGTAGAAGGACGCGATGGA  SEQ ID NO: 14
Reverse Primer   CAGGTACAAGAGCGTCATGCA  SEQ ID NO: 15
Probe            TCCTGTTCCCGCTGGGCTGC   SEQ ID NO: 16
```

In order to determine gene expression, ACC oxidase expression in the 0 μM inducer plus 0 μM ACC control treatment was normalized for each respective corn line. Relative expression for each corn line and average expression per treatment is shown in Table IV.

TABLE IV

ACC Oxidase Expression in Induced Corn

| Corn Line | 0 inducer/ 0 ACC | 0 inducer/ 1 μM ACC | 0 inducer/ 10 μM ACC | 20 μM inducer/0 ACC | 20 μM inducer/1 μM ACC | 20 μM inducer/ 10 μM ACC |
|---|---|---|---|---|---|---|
| B73 | 1 | 0.189902 | 0.600869 | 1.963743 | 0.095059 | 0.25889 |
| 4.5 | 1 | 0.486376 | 0.542974 | 1.350714 | 1.081217 | 0.418362 |
| 4.6 | 1 | 1.071547 | 1.098976 | 1.148245 | 0.758144 | 0.33477 |
| 4.7 | 1 | 2.465694 | 1.526099 | 0.74521 | 1.388455 | 0.255725 |
| 10.2 | 1 | 1.864168 | 0.846999 | 1.378451 | 0.492793 | 0.676117 |
| 10.4 | 1 | 0.665926 | 1.198439 | 0.343681 | 0.359115 | 1.82099 |
| 10.5 | 1 | 1.316937 | 1.366966 | 0.680428 | 0.068126 | 0.198294 |
| AVG ACO Expression | 1 | 1.151507 | 1.025903 | 1.08721 | 0.606129 | 0.566164 |
| SEM | 0 | 0.304275 | 0.142362 | 0.205243 | 0.188466 | 0.218046 |

As expected, the average expression of ACC oxidase in the transgenic corn lines was repressed in the presence of inducer plus ACC, the precursor of ethylene. The transgenic plants containing the activation and target cassettes for expression of etr1-1 in the presence of inducing compound for expression of mutant etr 1-1 demonstrated ethylene insensitivity, based on decreased expression of ethylene inducible genes.

Example 8

Effect of ACC Concentration on Ethylene Insensitivity

Homozygous tomato seed from one p1002 line and one p1003 line were germinated on medium containing 20 μM inducer and various levels of the ethylene precursor, ACC (i.e., 1.0-20 μM) As shown in Table V, induction of ethylene insensitivity occurred across the range of ACC concentrations tested. There was some decrease in the level of insensitivity achieved at higher ACC concentrations as seen by slightly less hypocotyl and root elongation, however, the values were still substantially increased relative to the wild-type control.

TABLE V

Ethylene insensitivity is induced over a range of ACC concentrations

| ACC (μM) | WT Hypocotyl (mm) | WT Root (mm) | p1002-18 Hypocotyl (mm) | p1002-18 Root (mm) | p1003-16 Hypocotyl (mm) | p1003-16 Root (mm) |
|---|---|---|---|---|---|---|
| 5 μM Ag | 41.4 ± 8.20 | 22.3 ± 5.66 | 38.2 ± 6.85 | 31.6 ± 5.68 | 36.3 ± 9.08 | 23.8 ± 4.92 |
| 0 | 36.4 ± 9.44 | 28.8 ± 6.26 | 40.7 ± 9.50 | 30.9 ± 7.14 | 39.8 ± 17.1 | 18.7 ± 3.94 |
| 1 | 25.9 ± 12.7 | 14.4 ± 9.42 | 28.4 ± 18.0 | 24.7 ± 7.53 | 39.3 ± 11.0 | 18.2 ± 716 |
| 2.5 | 11.3 ± 6.25 | 12.3 ± 9.41 | 29.4 ± 15.0 | 25.8 ± 8.50 | 38.9 ± 18.2 | 12.9 ± 8.61 |
| 5 | 8.50 ± 4.35 | 10.4 ± 8.73 | 27.3 ± 9.03 | 24.0 ± 7.77 | 33.0 ± 15.2 | 12.9 ± 9.36 |
| 10 | 7.71 ± 1.20 | 13.1 ± 10.8 | 28.0 ± 14.1 | 24.8 ± 6.03 | 29.7 ± 18.8 | 12.7 ± 12.1 |
| 20 | 3.21 ± 1.19 | 11.2 ± 9.40 | 26.5 ± 15.1 | 24.1 ± 3.98 | 24.3 ± 15.2 | 13.0 ± 7.92 |

Measurements were taken from 14 day old seedlings grown in the presence of inducer.

Example 9

The Degree of Ethylene Insensitivity in Plants as a Function of Inducer Concentration Homozygous tomato seeds from one p1002 containing and one p1003 containing line were germinated on medium containing 20 μM ACC and various levels of inducer (i.e., 0.5-20 μM). As shown in Table VI, the concentration of inducer was directly related to the level of ethylene insensitivity obtained for each line. These data demonstrate that different levels of ethylene insensitivity in plants can be achieved simply by adjusting the level of induction.

TABLE VI

The Level of Inducer Applied Modulates the Level of Ethylene Insensitivity

| Inducer (μM) | WT Hypocotyl (mm) | WT Root (mm) | p1002-18 Hypocotyl (mm) | p1002-18 Root (mm) | p1003-16 Hypocotyl (mm) | p1003-16 Root (mm) |
|---|---|---|---|---|---|---|
| 0 | 6.41 ± 2.83 | 8.58 ± 14.5 | 5.44 ± 2.92 | 9.63 ± 13.0 | 6.79 ± 2.26 | 12.1 ± 13.5 |
| 0.5 | — | — | 8.40 ± 6.29 | 12.0 ± 13.3 | 17.0 ± 6.46 | 14.4 ± 15.3 |
| 1 | — | — | 11.1 ± 7.41 | 16.5 ± 16.6 | 20.9 ± 10.7 | 10.3 ± 12.7 |
| 2.5 | — | — | 13.5 ± 8.97 | 16.0 ± 16.6 | 20.1 ± 8.77 | 9.19 ± 8.98 |
| 5 | — | — | 14.5 ± 7.75 | 15.2 ± 8.39 | 23.6 ± 11.4 | 20.2 ± 14.9 |
| 10 | — | — | 19.8 ± 10.8 | 22.7 ± 13.5 | 25.9 ± 8.77 | 29.1 ± 12.4 |
| 20 | 6.24 ± 2.75 | 9.06 ± 14.8 | 26.3 ± 11.9 | 33.3 ± 12.8 | 27.5 ± 9.10 | 25.6 ± 11.4 |

Measurements were taken from 10 day old seedlings.

Example 10

Transient Induction of Ethylene Insensitivity in Plants

To demonstrate that induced ethylene insensitive plants return to ethylene sensitive when the inducer is no longer provided, homozygous tomato seeds from one p1002 line were germinated on medium containing 20 μM ACC and 10 μM inducer for 2, 4, 6, 8 or 14 days. After 14 days growth in the dark, hypocotyls and roots were measured to assess ethylene insensitivity. Ethylene insensitive seedlings would be expected to have longer hypocotyls and roots. In the absence of inducer, the seedlings will become sensitive to ethylene and exhibit stunted growth in the dark. Thus, root and hypocotyl growth of the reversed seedlings should be intermediate between the sensitive and insensitive seedlings. As shown in Table VII, seedlings induced for 2, or 4 days and then removed from inducer for 10 or 6 days respectively showed return to a state of ethylene sensitivity when compared to the non-induced control seedling. Six days was sufficient to induce a full state of ethylene insensitivity in this p1002 containing tomato line.

TABLE VII

Removal of inducer results in restoration of ethylene sensitivity p1002-18-3

| Days with Inducer | Days without inducer | Hypocotyl (mm) | Percent (%) | Root (mm) | Percent (%) |
|---|---|---|---|---|---|
| 0 | 14 | 9.56 ± 3.74 | 36 | 11.9 ± 10.8 | 31.7 |
| 2 | 12 | 16.9 ± 4.30 | 63.8 | 26.2 ± 15.3 | 69.9 |
| 4 | 10 | 19.5 ± 7.52 | 73.6 | 28.7 ± 14.7 | 76.5 |
| 6 | 8 | 26.8 ± 6.27 | 101 | 29.8 ± 9.61 | 79.5 |
| 8 | 6 | 26.0 ± 10.3 | 98.1 | 38.3 ± 9.15 | 102 |
| 14 | 0 | 26.5 ± 7.51 | 100 | 37.5 ± 13.2 | 100 |

Measurements were taken from 14 day old seedlings grown in the dark on 20 μM ACC.

While the above examples show the use of the nucleotide sequence for etr1-1, the specification clearly provides one of skill in the art with the ability to modulate expression of many other genes in the ethylene biosynthesis pathways and other plant pathways in the same manner.

Numerous modifications and variations of the embodiments illustrated above are included in this specification and are expected to be obvious to one of skill in the art. Such modifications and alterations to the compositions and processes described herein are believed to be encompassed in the scope of the claims appended hereto.

All documents, including patents, patent applications and publications, and non-patent publications listed or referred to above, as well as the attached figures and/or Sequence Listing, are incorporated herein by reference in their entireties to the extent they are not inconsistent with the explicit teachings of this specification. However, the citation of any reference herein should not be construed as an admission that such reference is available as "Prior Art" to the instant application.

What is claimed is:

1. A method for producing a transgenic plant comprising:
   (a) transforming at least one cell in the plant with a gene expression system comprising:
      i. an activation cassette comprising, under control of a suitable promoter and in operative association therewith, (a) a GAL 4 DNA-binding domain (DBD) that recognizes a selected response element comprising five copies of GAL4 response element; (b) an ecdysone receptor ligand binding domain (EcRLBD); and (c) a VP16 activation domain (AD) which is activated in the presence of an inducing composition; and
      ii. a target cassette comprising (d) an inducible promoter comprising, in operative association, the response element to which the DBD of (a) binds and a minimal promoter responsive to the AD of (c), the inducible promoter controlling expression of (e) a nucleic acid sequence that encodes a selected protein that modifies sensitivity to ethylene in the plant, said protein selected from the group consisting of ethylene biosynthesis genes ACS and ACO, ACC deaminase, ethylene receptor genes, ETR1, ETR2, ERS1, ERS2 and EIN4, ethylene signaling pathway genes, RTE1, CTR1, EIN2, EIN3 and EIN3-like (EIL1-5), ethylene response factors, ERF1, EDF1, EDF2, EDF3 and EDF4, and EIN3 binding F-box proteins, EBF1 and EBF2, and mutants thereof;
      wherein interaction among the components of the activation cassette and the target cassette, when in a plant cell, with an inducing composition, modulates expression of the selected protein and selectively modulates ethylene sensitivity in the plant cell;
   (b) generating a plant from the transformed plant cell; and
   (c) selecting a plant comprising the transformed plant cell, which plant demonstrates selective modulation of ethylene insensitivity when the plant is contacted with the inducing composition, the modulation in protein expression controlled by the timing, the concentration, and the duration of the application of the inducing composition.

2. The method according to claim 1, wherein the activation cassette and the targeting cassette are present on the same plasmid.

3. The method according to claim 1, wherein the activation cassette and the targeting cassette are present on separate plasmids.

4. The method according to claim 1, wherein the promoter of the activation cassette is selected from the group consisting of a constitutive promoter, a plant cell-specific promoter, a plant tissue-specific promoter, a plant organ-specific promoter, an inducible promoter, a developmentally-specific promoter, and a cell differentiation-specific promoter.

5. The method according to claim 4, wherein the promoter is a constitutive promoter.

6. The method according to claim 1, wherein the ecdysone receptor LBD comprises all or a portion of an invertebrate ecdysone receptor or mutant thereof.

7. The method according to claim 6, wherein the ecdysone LBD contains a mutation of Thr to Val at amino acid position 335 in the full-length Cf EcR.

8. The method according to claim 1, wherein the inducible promoter comprises, in operative association, a minimal promoter sequence and one or more copies of a response element corresponding to the DNA binding domain in the activation cassette.

9. A method for modulating ethylene sensitivity in a plant comprising:
   applying an effective amount of an inducing composition to the cells of a transgenic plant, the plant comprising cells that stably express a gene expression system comprising:

i. an activation cassette comprising, under control of a suitable promoter and in operative association therewith, (a) a GAL 4 DNA-binding domain (DBD) that recognizes a selected response element comprising five copies of GAL4 response element; (b) an ecdysone receptor ligand binding domain (EcRLBD); and (c) a VP16 activation domain (AD) which is activated in the presence of an inducing composition; and ii. a target cassette comprising (d) an inducible promoter comprising, in operative association the response element to which the DBD of a binds and a minimal promoter responsive to the AD of (c), the inducible promoter controlling expression of (e) a nucleic acid sequence that encodes a selected protein that modifies sensitivity to ethylene in the plant, said protein selected from the group consisting of ethylene biosynthesis genes ACS and ACO, ACC deaminase, ethylene receptor genes, ETR1, ETR2, ERS1, ERS2 and EIN4, ethylene signaling pathway genes, RTE1, CTR1, EIN2, EIN3 and EIN3-like (EIL1-5), ethylene response factors, ERF1, EDF1, EDF2, EDF3 and EDF4, and EIN3 binding F-box proteins, EBF1 and EBF2, and mutants thereof;

wherein interaction among the components of the activation cassette and the target cassette, when in a plant cell, with the inducing composition, modulates expression of the selected protein and selectively modulates ethylene sensitivity in the plant cell, wherein in the presence of the inducing composition, the sensitivity of the plant cells to ethylene is decreased and in the absence of the inducing composition, the sensitivity of the plant cells to ethylene is increased; and wherein modulation of ethylene sensitivity is controlled by the timing, the concentration and the duration of the application of the inducing composition.

10. The method according to claim 9, wherein the inducing composition is a diacylhydrazine compound.

11. The method according to claim 9, wherein the ethylene sensitivity that is controlled is selected from the group consisting of senescence, fruit ripening, stress response, germination, pathogen resistance, leaf abscission, flower abscission, bud abscission, boll abscission, fruit abscission, flowering, and responses to drought, heat, population density and salinity.

12. A method for producing a transgenic plant comprising:
(a) transforming at least one cell in the plant with a gene expression system comprising:
i. an activation cassette comprising, under control of a constitutive G10-90 promoter and in operative association therewith, (a) a GAL 4 DBD that recognizes a response element comprising five copies of GAL4 response element; (b) an ecdysone receptor LBD; and (c) a VP16 AD which is activated in the presence of an inducing composition; and
ii. a target cassette comprising (d) an inducible promoter comprising, in operative association, the five copies of the GAL 4 response element and the minimal 35S promoter responsive to activation of the VP16 AD, the inducible promoter controlling expression of (e) a nucleic acid sequence of the etr1-1 gene that encodes a mutant ETR1 protein;

wherein interaction among the components of the activation cassette and the targeting cassette, when in a plant cell, with an inducing composition, modulates expression of the mutant ETR1 protein and selectively decreases ethylene sensitivity in the plant cell;

(b) generating a plant from the transformed plant cell; and
(c) selecting a plant comprising the transformed plant cell, which plant demonstrates selective modulation of ethylene sensitivity when the plant is contacted with the inducing composition, wherein a decrease in the mutant ETR1 protein expression is controlled by the timing, the concentration, and the duration of the application of the inducing composition.

13. A method for modulating ethylene sensitivity in a plant comprising:
applying an effective amount of an inducing composition to the cells of a transgenic plant, the plant comprising cells that stably express a gene expression system comprising:
i. an activation cassette comprising, under control of a constitutive G10-90 promoter and in operative association therewith, (a) a GAL 4 DBD that recognizes a response element comprising five copies of GAL4 response element; (b) an ecdysone receptor LBD; and (c) a VP16 AD which is activated in the presence of an inducing composition; and
ii. a target cassette comprising (d) an inducible promoter comprising, in operative association, the five copies of the GAL 4 response element and the minimal 35S promoter responsive to activation of the VP16 AD, the inducible promoter controlling expression of (e) a nucleic acid sequence of the etr1-1 gene that encodes a mutant ETR1 protein;

wherein interaction among the components of the activation cassette and the targeting cassette, when in a plant cell, with an inducing composition, modulates expression of the mutant ETR1 protein and selectively decreases ethylene sensitivity in the plant cell;

wherein in the presence of the inducing composition, the sensitivity of the plant cells to ethylene is decreased and in the absence of the inducing composition, the sensitivity of the plant cells to ethylene is increased; and wherein modulation of ethylene sensitivity is controlled by the timing, the concentration and the duration of the application of the inducing composition.

14. The method according to claim 12, wherein the inducing composition is a diacylhydrazine compound.

15. The method according to claim 13, wherein the inducing composition is a diacylhydrazine compound.

* * * * *